United States Patent
Saboulard et al.

(10) Patent No.: US 8,623,824 B2
(45) Date of Patent: Jan. 7, 2014

(54) VIII FACTORS FOR THE TREATMENT OF TYPE A HEMOPHILIA

(75) Inventors: Didier Saboulard, Saint Gaudens (FR); Jean-Luc Plantier, Gringy (FR); Marc Delcourt, Paris (FR); Claude Negrier, Irigny (FR); Thierry Menguy, Gif sur Yvette (FR); Stephane Blesa, Grisy-suisnes (FR); Sylvie Marin, Communay (FR)

(73) Assignees: Biomethodes, Evry (FR); Hospices Civils de Lyon, Lyon Cedex (FR)

( * ) Notice: Subject to any disclaimer, the term of this patent is extended or adjusted under 35 U.S.C. 154(b) by 753 days.

(21) Appl. No.: 12/528,379

(22) PCT Filed: Feb. 22, 2008

(86) PCT No.: PCT/FR2008/050301
§ 371 (c)(1),
(2), (4) Date: Dec. 30, 2009

(87) PCT Pub. No.: WO2008/129180
PCT Pub. Date: Oct. 30, 2008

(65) Prior Publication Data
US 2010/0311659 A1   Dec. 9, 2010

(30) Foreign Application Priority Data
Feb. 23, 2007   (FR) .................................. 07 53450

(51) Int. Cl.
*A61K 38/37* (2006.01)
*C12Q 1/56* (2006.01)

(52) U.S. Cl.
USPC ........................................... 514/14.1; 435/13

(58) Field of Classification Search
None
See application file for complete search history.

(56) References Cited

U.S. PATENT DOCUMENTS

| | | | |
|---|---|---|---|
| 4,868,112 A | 9/1989 | Toole, Jr. | |
| 5,364,771 A | 11/1994 | Lollar et al. | |
| 5,583,209 A | 12/1996 | Lollar et al. | |
| 5,663,060 A | 9/1997 | Lollar et al. | |
| 5,744,446 A | 4/1998 | Lollar et al. | |
| 5,859,204 A | 1/1999 | Lollar | |
| 5,888,974 A | 3/1999 | Lollar et al. | |
| 6,060,447 A | 5/2000 | Chapman et al. | |
| 6,180,371 B1 | 1/2001 | Lollar | |
| 6,228,620 B1 | 5/2001 | Chapman et al. | |
| 6,376,463 B1 | 4/2002 | Lollar | |
| 6,458,563 B1 | 10/2002 | Lollar | |
| 6,759,216 B1 | 7/2004 | Lollar | |

(Continued)

FOREIGN PATENT DOCUMENTS

| | | |
|---|---|---|
| EP | 1048726 | 11/2000 |
| EP | 1283263 | 2/2003 |

(Continued)

OTHER PUBLICATIONS

FVIII *Callicebus moloch* (last viewed on May 25, 2012).*
Human coagulation factor VIII precursor isoform 2 (last viewed on Sep. 6, 2012).*
Human coagulation factor VIII precursor isoform 1 (last viewed on May 25, 2012).*

(Continued)

*Primary Examiner* — Alexander Kim
(74) *Attorney, Agent, or Firm* — Saliwanchik, Lloyd & Eisenschenk

(57) ABSTRACT

The present invention relates to improved human FVIII variants having at least one substitution in the A2 and/or C2 domain. The present invention also relates to their uses in the treatment of hemophilia A, particularly in patients with inhibitors.

16 Claims, 27 Drawing Sheets

(56) References Cited

U.S. PATENT DOCUMENTS

Figure 1:
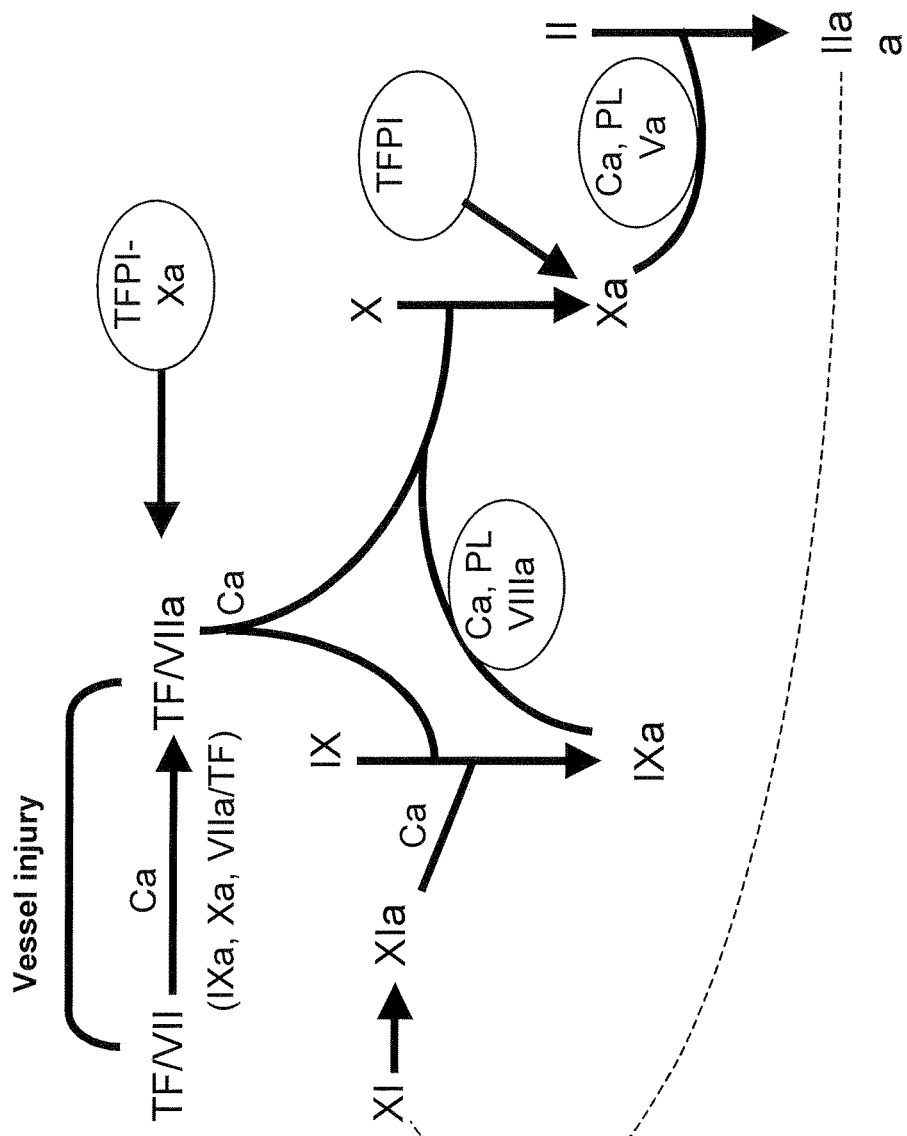
Figure 2A:
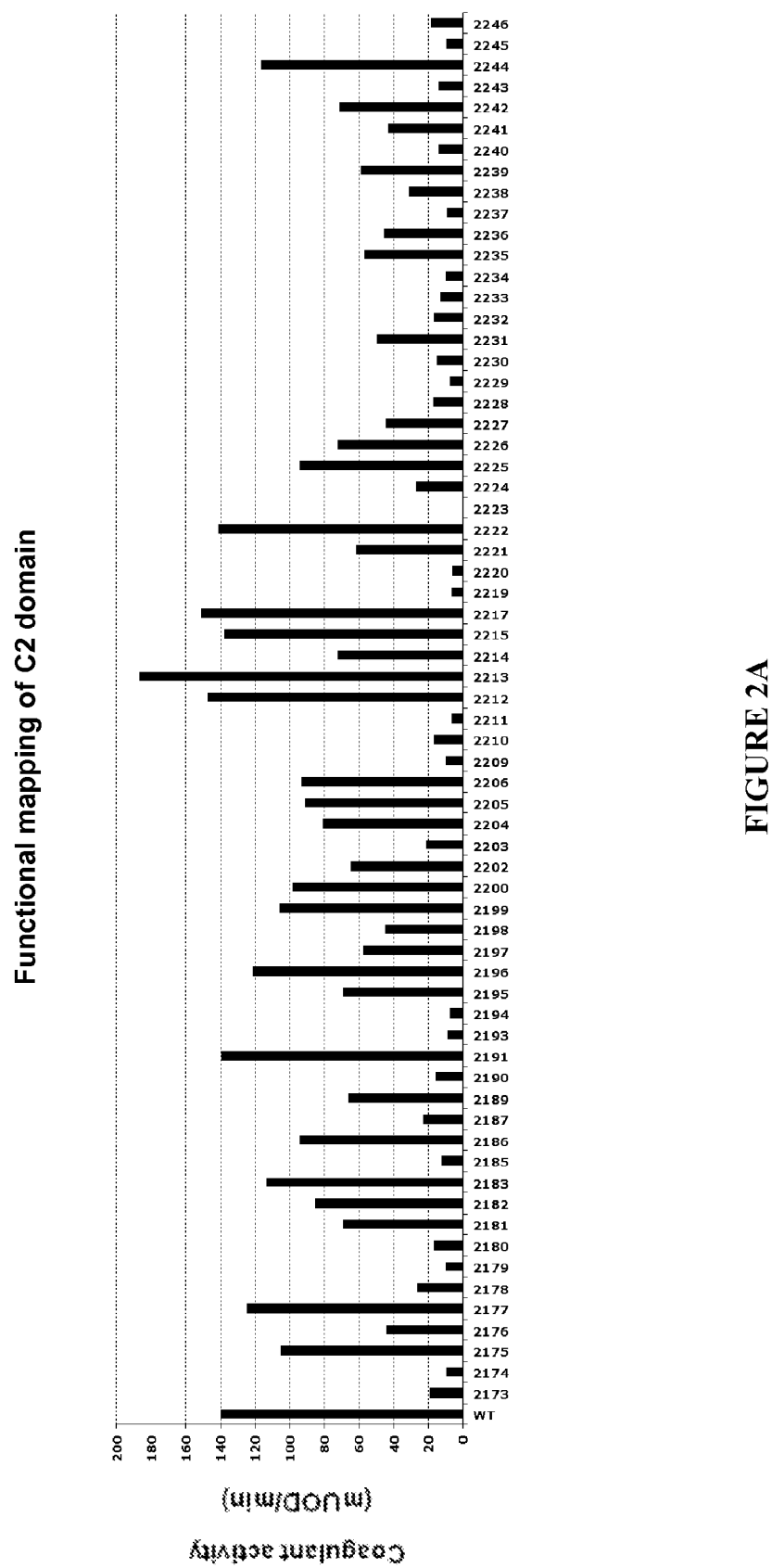
Figure 2B:
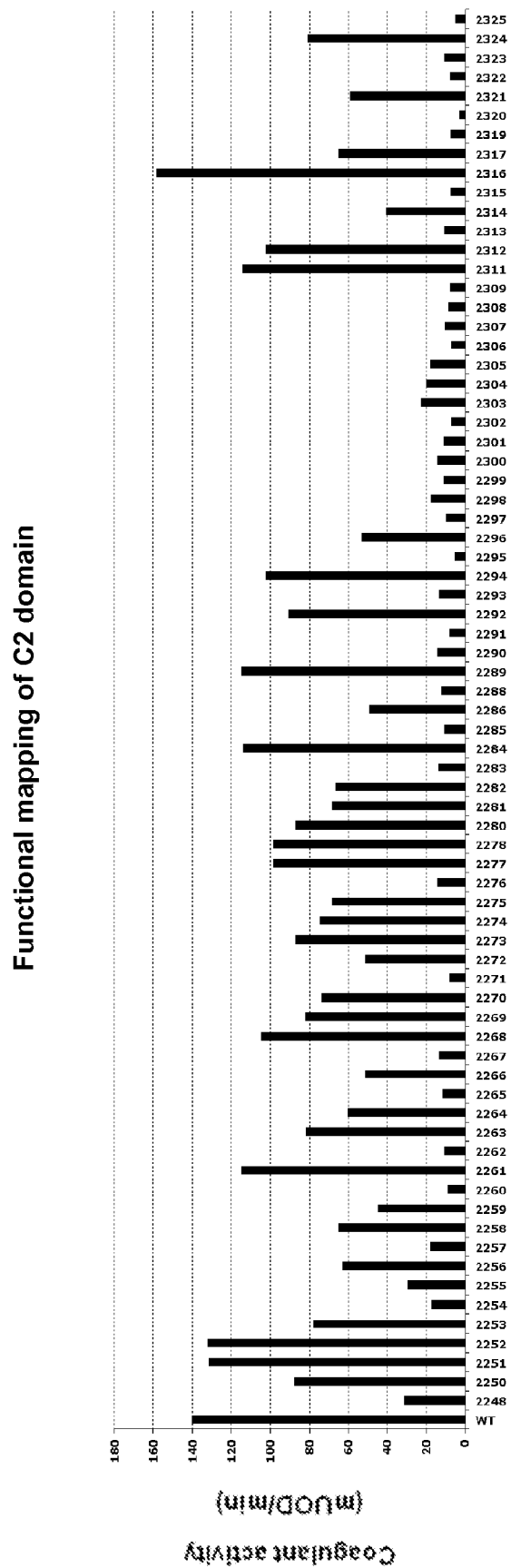
Figure 2C:
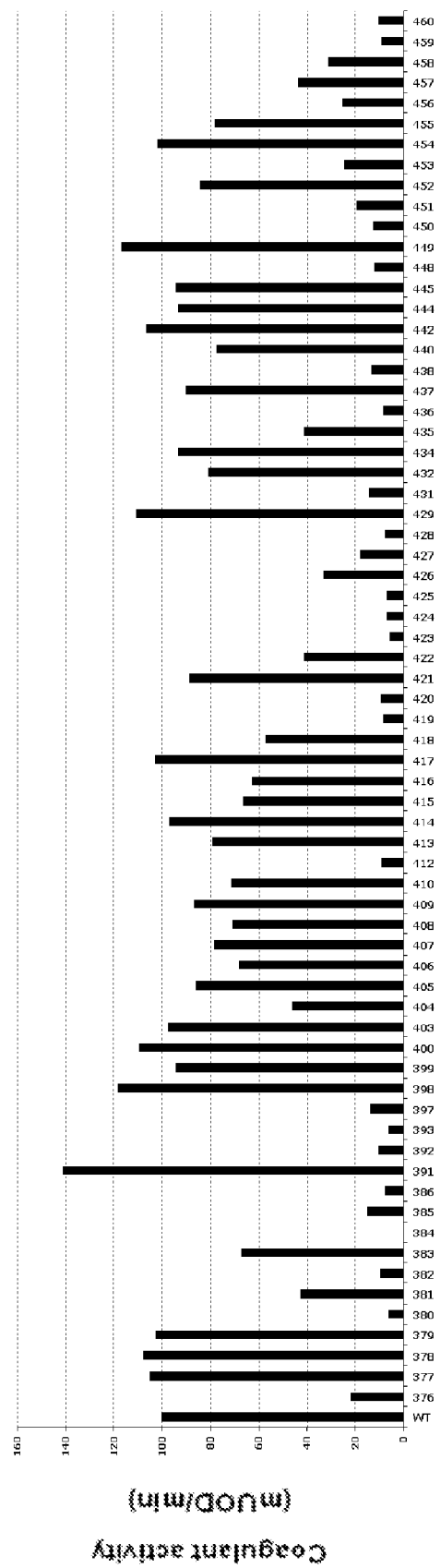
Figure 2D:
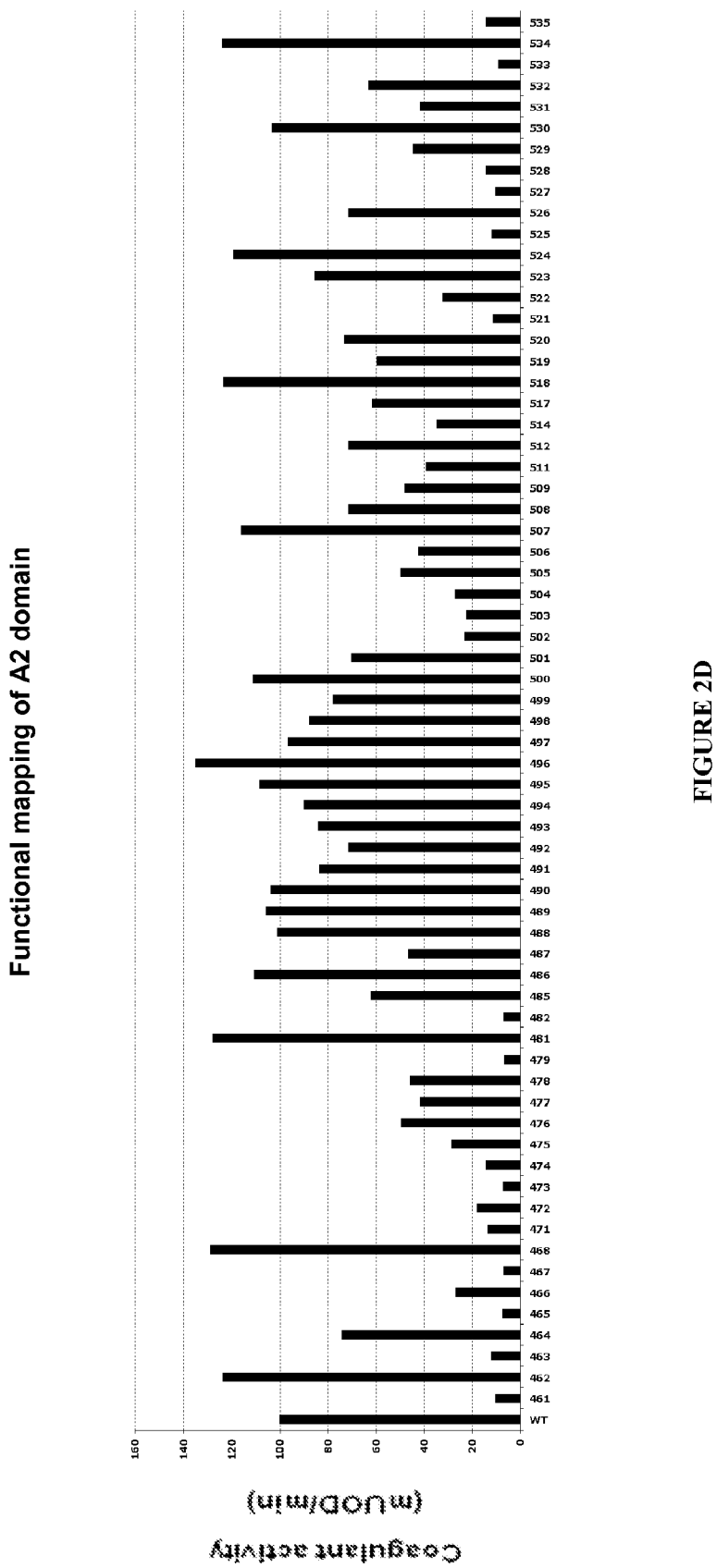
Figure 2E:
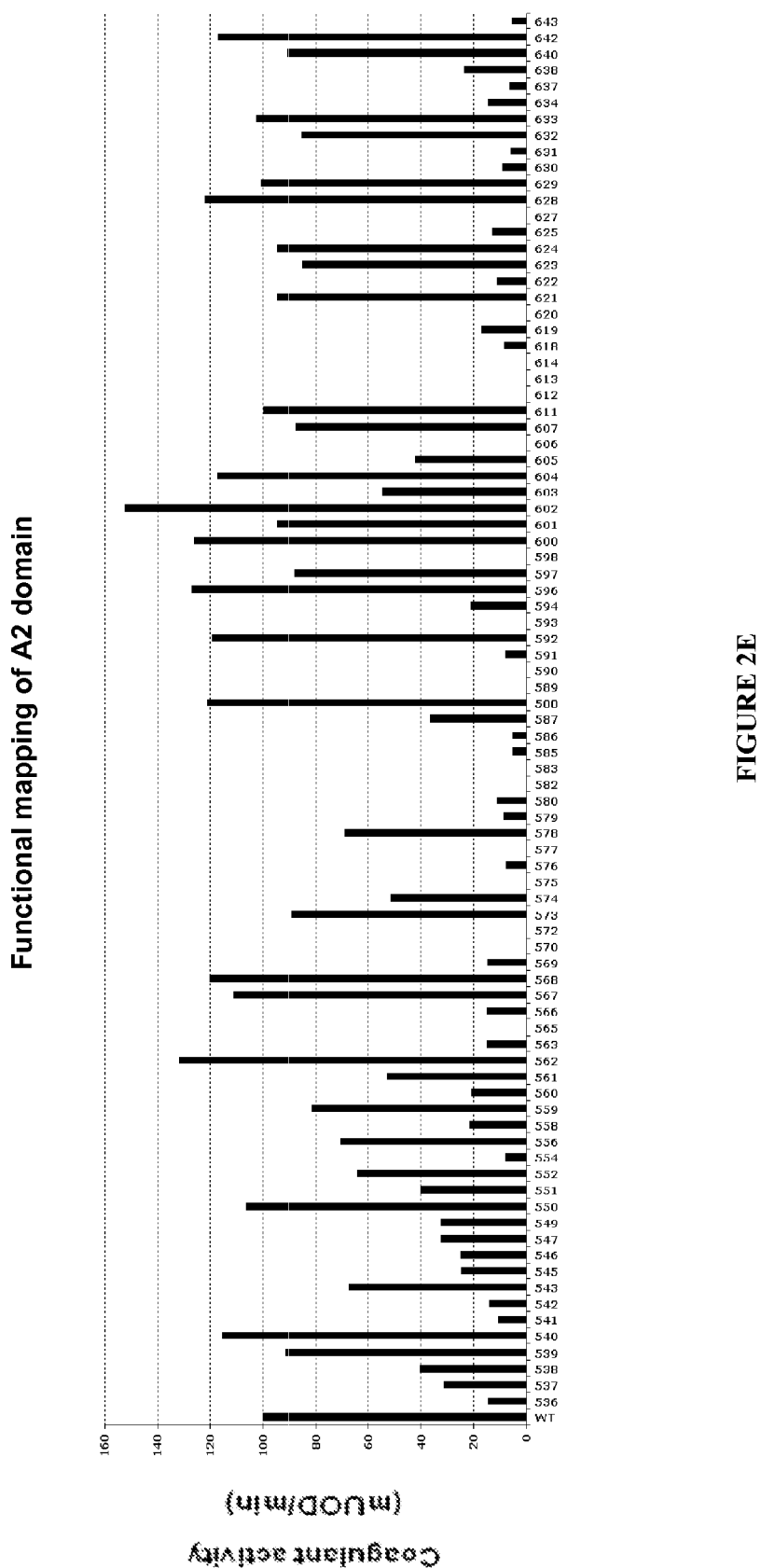

| | | |
|---|---|---|
| 6,770,744 B2 | 8/2004 | Lollar |
| 6,780,614 B2 | 8/2004 | Negrier et al. |
| 6,919,311 B2 | 7/2005 | Lenting et al. |
| 7,012,132 B2 | 3/2006 | Lollar |
| 2002/0165177 A1 | 11/2002 | Negrier et al. |
| 2002/0182670 A1 | 12/2002 | Lollar |
| 2002/0182684 A1 | 12/2002 | Negrier et al. |
| 2003/0068785 A1* | 4/2003 | Lollar ............ 435/69.6 |
| 2003/0083257 A1 | 5/2003 | Negrier et al. |
| 2003/0147900 A1 | 8/2003 | Laub et al. |
| 2003/0166536 A1 | 9/2003 | Lollar |
| 2004/0197875 A1 | 10/2004 | Hauser et al. |
| 2004/0249134 A1 | 12/2004 | Lollar |
| 2005/0079584 A1 | 4/2005 | Lollar |
| 2005/0256304 A1 | 11/2005 | Jones et al. |
| 2006/0241039 A1* | 10/2006 | Pryzdial et al. ........... 514/12 |

FOREIGN PATENT DOCUMENTS

| | | |
|---|---|---|
| EP | 1359222 | 11/2003 |
| EP | 1454916 | 9/2004 |
| EP | 1502921 | 2/2005 |
| EP | 1 200 105 | 3/2005 |
| EP | 1561757 | 8/2005 |
| JP | 2004-141173 | 5/2004 |
| WO | WO 93-20093 | 10/1993 |
| WO | WO 95-24427 | 9/1995 |
| WO | WO 97-49725 | 12/1997 |
| WO | WO 99-46274 | 9/1999 |
| WO | WO 00-48635 | 8/2000 |
| WO | WO 00-71141 | 11/2000 |
| WO | WO 01-68109 | 9/2001 |
| WO | WO 02-24723 | 3/2002 |
| WO | WO 03-047507 | 6/2003 |
| WO | WO 2005-040213 | 5/2005 |
| WO | WO 2005/046583 | 5/2005 |
| WO | WO 2005/046583 | 5/2005 |
| WO | WO 2005-107776 | 11/2005 |
| WO | WO 2005-111074 | 11/2005 |
| WO | WO /2006/103298 * | 10/2006 |

OTHER PUBLICATIONS

Doering et al., Decreased factor VIII levels during acetaminophen-induced murine fulminant hepatic failure, Blood, (2003), vol. 102, pp. 1743-1744.*

Rowland et al., Crystal structure of human cytochrome P450 2D6, J Biol Chem. (Epub Dec. 13, 2005), vol. 281(11), pp. 7614-7622.*

Stoilova-McPhie et al., 3-Dimensional structure of membrane-bound coagulation factor VIII: modeling of the factor VIII heterodimer within a 3-dimensional density map derived by electron crystallography, Blood (2002), vol. 99,No. 4, pp. 1215-1223.*

Human cytochrome 450 2D6 (last viewed on Sep. 7, 2012).*

Eaton, D.L. et al., "Construction and Characterization of an Active Factor VIII Variant Lacking the Central One-Third of the Molecule," *Biochemistry*, Dec. 30, 1986, pp. 8343-8347, vol. 25, No. 26.

Healey, J.F. et al., "Residues 484-508 Contain a Major Determinant of the Inhibitory Epitope in the A2 Domain of Human Factor VIII," *The Journal of Biological Chemistry*, Jun. 16, 1995, pp. 14505-14509, vol. 270, No. 24.

Koshihara, K. et al., "Immunoblot cross-reactivity of factor VIII inhibitors with porcine factor VIII," *Blood*, 1995, pp. 2183-2190, vol. 86.

Lollar, P. et al., "Inhibition of Human Factor VIIIa by Anti-A2 Subunit Antibodies," *J. Clin. Invest.*, Jun. 1994, pp. 2497-2504, vol. 93.

Lubin, I.M. et al., "Elimination of a Major Inhibitor Epitope in Factor VIII," *The Journal of Biological Chemistry*, Mar. 25, 1994, pp. 8639-8641, vol. 269, No. 12.

Pratt, K.P. et al., "Structure of the C2 domain of human factor VIII at 1.5 Å resolution," *Nature*, Nov. 25, 1999, pp. 439-442, vol. 402.

Prescott, R. et al., "The Inhibitor Antibody Response is More Complex in Hemophilia A Patients Than in Most Nonhemophilliacs With Factor VIII Autoantibodies," *Blood*, May 15, 1997, pp. 3663-3671, vol. 89, No. 10.

Toole, J.J. et al., "A large region (≈95 kDa) of human factor VIII is dispensable for in vitro procoagulant activity," *Proc. Natl. Acad. Sci. USA*, Aug. 1986, pp. 5939-5942, vol. 83.

Barrow, R. T. et al. "Reduction of the antigenicity of factor VIII toward complex inhibitory antibody plasmas using multiply-substituted hybrid human/porcine factor VIII molecules" Blood, Jan. 15, 2000, pp. 564-568, vol. 95, No. 2.

* cited by examiner

| C2 mutants | Concentration higher than 10 ng/ml | Specific activity higher than 4 (mUOD/min/ng/ml) |
|---|---|---|
| 2177 | 18,40 | 6,77 |
| 2183 | 11,80 | 9,57 |
| 2186 | 17,62 | 5,33 |
| 2191 | 27,27 | 5,11 |
| 2196 | 28,59 | 4,24 |
| 2204 | 14,36 | 5,62 |
| 2205 | 11,39 | 7,99 |
| 2206 | 14,62 | 6,36 |
| 2213 | 25,49 | 7,34 |
| 2217 | 24,75 | 6,11 |
| 2235 | 13,35 | 4,27 |
| 2258 | 11,61 | 5,60 |
| 2264 | 11,23 | 5,37 |
| 2268 | 11,29 | 9,24 |
| 2269 | 16,38 | 5,01 |

FIGURE 4

Example of abolition to inhibition of mutant
518 on serum of patient TD a = % residual activity (WT)
b = % residual activity (mutant)
% abolition to inhibition = -[(b-a) / a] x 100

| mutant | Activity (mUOD/min) | mutant | Activity (mUOD/min) | mutant | Activity (mUOD/min) | mutant | Activity (mUOD/min) |
|---|---|---|---|---|---|---|---|
| 2175 | 103,5 | 2215 | 215 | 2269 | 98 | 2324 | 85 |
| 2177 | 125,5 | 2217 | 162,5 | 2270 | 123,5 | | |
| 2181 | 81,6 | 2221 | 71,5 | 2273 | 126,5 | WT | 100 |
| 2182 | 85,3 | 2222 | 149,5 | 2274 | 88 | | |
| 2183 | 120,5 | 2225 | 85,5 | 2275 | 81,5 | | |
| 2186 | 80,5 | 2226 | 81 | 2277 | 151,5 | | |
| 2189 | 74,8 | 2235 | 72,5 | 2278 | 133 | | |
| 2191 | 175,6 | 2239 | 76 | 2280 | 116,5 | | |
| 2195 | 86,8 | 2242 | 90,5 | 2281 | 88,2 | | |
| 2196 | 152,5 | 2244 | 124,5 | 2282 | 75,5 | | |
| 2197 | 71 | 2250 | 126,5 | 2284 | 114 | | |
| 2199 | 114,5 | 2251 | 131 | 2289 | 162 | | |
| 2200 | 131,4 | 2252 | 136,5 | 2292 | 136 | | |
| 2202 | 75,3 | 2253 | 86,5 | 2294 | 113 | | |
| 2204 | 92 | 2256 | 76 | 2296 | 52,8 | | |
| 2205 | 78 | 2258 | 97,5 | 2311 | 137 | | |
| 2206 | 105,5 | 2261 | 174,5 | 2312 | 129,5 | | |
| 2212 | 134 | 2263 | 126,5 | 2316 | 162,5 | | |
| 2213 | 141 | 2264 | 115 | 2317 | 64 | | |
| 2214 | 121 | 2268 | 116,5 | 2321 | 58 | | |

FIGURE 12

| mutant | Activity (mUOD/min) | mutant | Activity (mUOD/min) | mutant | Activity (mUOD/min) | mutant | Activity (mUOD/min) |
|---|---|---|---|---|---|---|---|
| 377 | 110,5 | 421 | 128 | 489 | 142,5 | 523 | 92 |
| 378 | 147,5 | 429 | 113 | 490 | 121,5 | 524 | 131,5 |
| 379 | 114,5 | 432 | 100,5 | 491 | 100,5 | 526 | 73 |
| 383 | 67 | 434 | 82 | 492 | 113,5 | 530 | 109 |
| 391 | 153 | 437 | 82 | 493 | 78,5 | 532 | 63 |
| 398 | 88,5 | 440 | 72,5 | 494 | 101 | 534 | 138,5 |
| 399 | 94,5 | 442 | 96 | 495 | 131,5 | 539 | 91 |
| 400 | 132,5 | 444 | 91,5 | 496 | 143 | 540 | 137,5 |
| 403 | 101,5 | 445 | 96 | 497 | 121 | 543 | 67,2 |
| 405 | 86 | 449 | 128,5 | 498 | 133 | 550 | 114 |
| 406 | 148 | 452 | 99 | 499 | 78 | 552 | 64,2 |
| 407 | 78,5 | 454 | 140 | 500 | 126 | 556 | 85 |
| 408 | 78 | 455 | 87 | 501 | 125,5 | 559 | 145 |
| 409 | 138 | 462 | 128,5 | 507 | 117,5 | 562 | 157 |
| 410 | 71 | 464 | 81 | 508 | 86 | 567 | 115,5 |
| 413 | 104,5 | 468 | 178 | 512 | 71,5 | 568 | 136,5 |
| 414 | 113,5 | 481 | 172,5 | 517 | 61,5 | 573 | 93 |
| 415 | 66,5 | 485 | 62 | 518 | 152,5 | 578 | 83 |
| 416 | 62 | 486 | 147 | 519 | 60 | 588 | 145 |
| 417 | 118 | 488 | 148,5 | 520 | 80,5 | 592 | 165 |

FIGURE 13

| mutant | Activity (mUOD/min) |
|---|---|
| 596 | 147,5 |
| 597 | 87 |
| 600 | 132 |
| 601 | 99,5 |
| 602 | 157,5 |
| 604 | 146,5 |
| 607 | 106 |
| 611 | 125,5 |
| 621 | 108,5 |
| 623 | 128,5 |
| 624 | 128,5 |
| 628 | 123,5 |
| 629 | 107,5 |
| 632 | 110 |
| 633 | 113 |
| 640 | 146 |
| 642 | 134,5 |
| | |
| | |
| | |

FIGURE 14

|  |  | FS | TD | GC | PR | SL |
|---|---|---|---|---|---|---|
| Mutants | 400 | 23 | 17 | - | - | - |
|  | 486 | 14 | 24 | 10 | 14 | - |
|  | 493 | - | 20 | 28 | - | - |
|  | 403 | 34 | - | 10 | - | 16 |
|  | 562 | 10 | 9 | 15 | - | 29 |
|  | 414 | 33 | 9 | - | - | - |
|  | 437 | 16 | ND | - | - | - |

FIGURE 15

|  |  | FS | TD | GC | PR | SL |
|---|---|---|---|---|---|---|
| Mutants | 518 | - | 22 | - | - | - |
|  | 2280 | - | 34 | 12 | 6 | 21 |
|  | 2275 | - | - | 10 | 19 | 24 |
|  | 2244 | - | 38 | - | - | 25 |
|  | 2212 | 25 | 16 | - | - | - |
|  | 2202 | - | 18 | - | - | - |

FIGURE 16

|  |  | FS | TD | GC | PR | SL |
|---|---|---|---|---|---|---|
| Mutants | 421 | 33 | 9 | 5 | - | - |
|  | 494 | - | 17 | 28 | 5 | - |
|  | 496 | - | - | 24 | 15 | 16 |
|  | 2206 | 21 | 30 | - | - | 5 |
|  | 2226 | - | 32 | 3 | - | - |
|  | 2261 | 17 | - | - | - | 5 |
|  | 2281 | - | 22 | - | 3 | 6 |
|  | 2282 | - | 30 | - | 3 | - |
|  | 2311 | - | 35 | 13 | - | - |

FIGURE 17

|  | | FS | TD | GC | PR | SL |
|---|---|---|---|---|---|---|
| Mutants | 409 | 31 | 12 | 5 | - | 15 |
|  | 462 | 25 | 12 | 5 | - | 28 |
|  | 507 | - | 27 | 5 | 5 | - |
|  | 629 | - | 40 | - | 12 | 15 |
|  | 2312 | - | 36 | - | - | - |
|  | 2289 | - | 30 | 12 | - | 13 |
|  | 2316 | - | 46 | 10 | - | 36 |
|  | 2294 | - | 28 | 36 | - | 20 |

FIGURE 18

| mutant | Activité muDO/min | Activité Spécifique muDO/min/ng/ml | mutant | Activité muDO/min | Activité Spécifique muDO/min/ng/ml |
|---|---|---|---|---|---|
| 2202 | 75,3 | 7,52 | 400 | 132,5 | 13,6 |
| 2206 | 105,5 | 7,25 | 403 | 101,5 | 7,05 |
| 2212 | 134 | 6,89 | 409 | 138 | 12,35 |
| 2226 | 81 | 12,6 | 414 | 113,5 | 14,34 |
| 2244 | 124,5 | 10,02 | 421 | 128 | 19,21 |
| 2261 | 174,5 | 55,84 | 437 | 82 | 7,34 |
| 2275 | 81,5 | 11,54 | 462 | 128,5 | 16,8 |
| 2280 | 116,5 | 12,12 | 486 | 147 | 16,6 |
| 2281 | 88,2 | 17,37 | 493 | 78,5 | 18,06 |
| 2282 | 75,5 | 15,1 | 494 | 101 | 10,1 |
| 2289 | 162 | 8,67 | 496 | 143 | 15,03 |
| 2294 | 113 | 10,21 | 507 | 117,5 | 13,6 |
| 2311 | 137 | 24,4 | 518 | 152,5 | 11,5 |
| 2312 | 129,5 | 12,12 | 629 | 107,5 | 20,4 |
| 2316 | 162,5 | 10,67 |  |  |  |
| 562 | 157 | 14,37 | WT | 100 | 3,2 |

FIGURE 19

| 409/462 | 409/2289 | 507/2312 | 2289/629 |
| --- | --- | --- | --- |
| 409/507 | 409/2316 | 507/2289 | 2312/2289 |
| 409/629 | 409/2294 | 507/2316 | 2312/2316 |
| 462/507 | 462/2312 | 507/2294 | 2312/2294 |
| 462/629 | 462/2289 | 2312/629 | 2289/2316 |
| 507/629 | 462/2316 | 2316/629 | 2289/2294 |
| 409/2312 | 462/2294 | 2294/629 | 2316/2294 |

FIGURE 20

| | TD antibody Abolition to inhibition (%) | GC antibody Abolition to inhibition (%) | SL antibody Abolition to inhibition (%) | PR antibody Abolition to inhibition (%) | Specific activity (mUOD/ng/ml) |
|---|---|---|---|---|---|
| 409/462 | 49 | 93 | 0 | 19 | 19,7 |
| 409/507 | 57 | 71 | 28 | 51 | 9,4 |
| 409/629 | 19 | ND | ND | ND | 6,14 |
| 462/507 | 57 | 57 | 6 | 49 | 12,1 |
| 462/629 | 33 | 93 | 94 | 43 | 7,1 |
| 507/629 | 12 | 12 | 0 | 10 | 7,04 |

FIGURE 21

```
                        SEQUENCE LISTING

<160> NUMBER OF SEQ ID NOS: 5

<210> SEQ ID NO 1
<211> LENGTH: 9028
<212> TYPE: DNA
<213> ORGANISM: Homo sapiens
<220> FEATURE:
<221> NAME/KEY: CDS
<222> LOCATION: (172)..(7227)
<223> OTHER INFORMATION:
<220> FEATURE:
<221> NAME/KEY: sig_peptide
<222> LOCATION: (172)..(228)
<223> OTHER INFORMATION:

<400> SEQUENCE: 1
gcttagtgct gagcacatcc agtgggtaaa gttccttaaa atgctctgca aagaaattgg      60
gacttttcat taaatcagaa attttacttt ttccccctcc tgggagctaa agatatttta     120
gagaagaatt aaccttttgc ttctccagtt gaacatttgt agcaataagt c atg caa     177
                                                        Met Gln
                                                          1 ata gag ctc tcc acc tgc ttc ttt ctg tgc ctt ttg cga ttc tgc ttt     225
Ile Glu Leu Ser Thr Cys Phe Phe Leu Cys Leu Leu Arg Phe Cys Phe
         5                  10                  15 agt gcc acc aga aga tac tac ctg ggt gca gtg gaa ctg tca tgg gac     273
Ser Ala Thr Arg Arg Tyr Tyr Leu Gly Ala Val Glu Leu Ser Trp Asp
     20                  25                  30 tat atg caa agt gat ctc ggt gag ctg cct gtg gac gca aga ttt cct     321
Tyr Met Gln Ser Asp Leu Gly Glu Leu Pro Val Asp Ala Arg Phe Pro
 35                  40                  45                  50 cct aga gtg cca aaa tct ttt cca ttc aac acc tca gtc gtg tac aaa     369
Pro Arg Val Pro Lys Ser Phe Pro Phe Asn Thr Ser Val Val Tyr Lys
                 55                  60                  65 aag act ctg ttt gta gaa ttc acg gat cac ctt ttc aac atc gct aag     417
Lys Thr Leu Phe Val Glu Phe Thr Asp His Leu Phe Asn Ile Ala Lys
             70                  75                  80 cca agg cca ccc tgg atg ggt ctg cta ggt cct acc atc cag gct gag     465
Pro Arg Pro Pro Trp Met Gly Leu Leu Gly Pro Thr Ile Gln Ala Glu
         85                  90                  95 gtt tat gat aca gtg gtc att aca ctt aag aac atg gct tcc cat cct     513
Val Tyr Asp Thr Val Val Ile Thr Leu Lys Asn Met Ala Ser His Pro
    100                 105                 110 gtc agt ctt cat gct gtt ggt gta tcc tac tgg aaa gct tct gag gga     561
Val Ser Leu His Ala Val Gly Val Ser Tyr Trp Lys Ala Ser Glu Gly
115                 120                 125                 130 gct gaa tat gat gat cag acc agt caa agg gag aaa gaa gat gat aaa     609
Ala Glu Tyr Asp Asp Gln Thr Ser Gln Arg Glu Lys Glu Asp Asp Lys
```

-continued

```
                135                  140                  145
gtc ttc cct ggt gga agc cat aca tat gtc tgg cag gtc ctg aaa gag      657
Val Phe Pro Gly Gly Ser His Thr Tyr Val Trp Gln Val Leu Lys Glu
        150                  155                  160 aat ggt cca atg gcc tct gac cca ctg tgc ctt acc tac tca tat ctt      705
Asn Gly Pro Met Ala Ser Asp Pro Leu Cys Leu Thr Tyr Ser Tyr Leu
        165                  170                  175 tct cat gtg gac ctg gta aaa gac ttg aat tca ggc ctc att gga gcc      753
Ser His Val Asp Leu Val Lys Asp Leu Asn Ser Gly Leu Ile Gly Ala
        180                  185                  190 cta cta gta tgt aga gaa ggg agt ctg gcc aag gaa aag aca cag acc      801
Leu Leu Val Cys Arg Glu Gly Ser Leu Ala Lys Glu Lys Thr Gln Thr
195                  200                  205                  210 ttg cac aaa ttt ata cta ctt ttt gct gta ttt gat gaa ggg aaa agt      849
Leu His Lys Phe Ile Leu Leu Phe Ala Val Phe Asp Glu Gly Lys Ser
                215                  220                  225 tgg cac tca gaa aca aag aac tcc ttg atg cag gat agg gat gct gca      897
Trp His Ser Glu Thr Lys Asn Ser Leu Met Gln Asp Arg Asp Ala Ala
        230                  235                  240 tct gct cgg gcc tgg cct aaa atg cac aca gtc aat ggt tat gta aac      945
Ser Ala Arg Ala Trp Pro Lys Met His Thr Val Asn Gly Tyr Val Asn
        245                  250                  255 agg tct ctg cca ggt ctg att gga tgc cac agg aaa tca gtc tat tgg      993
Arg Ser Leu Pro Gly Leu Ile Gly Cys His Arg Lys Ser Val Tyr Trp
        260                  265                  270 cat gtg att gga atg ggc acc act cct gaa gtg cac tca ata ttc ctc     1041
His Val Ile Gly Met Gly Thr Thr Pro Glu Val His Ser Ile Phe Leu
275                  280                  285                  290 gaa ggt cac aca ttt ctt gtg agg aac cat cgc cag gcg tcc ttg gaa     1089
Glu Gly His Thr Phe Leu Val Arg Asn His Arg Gln Ala Ser Leu Glu
                295                  300                  305 atc tcg cca ata act ttc ctt act gct caa aca ctc ttg atg gac ctt     1137
Ile Ser Pro Ile Thr Phe Leu Thr Ala Gln Thr Leu Leu Met Asp Leu
        310                  315                  320 gga cag ttt cta ctg ttt tgt cat atc tct tcc cac caa cat gat ggc     1185
Gly Gln Phe Leu Leu Phe Cys His Ile Ser Ser His Gln His Asp Gly
        325                  330                  335 atg gaa gct tat gtc aaa gta gac agc tgt cca gag gaa ccc caa cta     1233
Met Glu Ala Tyr Val Lys Val Asp Ser Cys Pro Glu Glu Pro Gln Leu
        340                  345                  350 cga atg aaa aat aat gaa gaa gcg gaa gac tat gat gat gat ctt act     1281
Arg Met Lys Asn Asn Glu Glu Ala Glu Asp Tyr Asp Asp Asp Leu Thr
355                  360                  365                  370 gat tct gaa atg gat gtg gtc agg ttt gat gat gac aac tct cct tcc     1329
Asp Ser Glu Met Asp Val Val Arg Phe Asp Asp Asp Asn Ser Pro Ser
                375                  380                  385 ttt atc caa att cgc tca gtt gcc aag aag cat cct aaa act tgg gta     1377
Phe Ile Gln Ile Arg Ser Val Ala Lys Lys His Pro Lys Thr Trp Val
        390                  395                  400 cat tac att gct gct gaa gag gag gac tgg gac tat gct ccc tta gtc     1425
His Tyr Ile Ala Ala Glu Glu Glu Asp Trp Asp Tyr Ala Pro Leu Val
        405                  410                  415 ctc gcc ccc gat gac aga agt tat aaa agt caa tat ttg aac aat ggc     1473
Leu Ala Pro Asp Asp Arg Ser Tyr Lys Ser Gln Tyr Leu Asn Asn Gly
        420                  425                  430 cct cag cgg att ggt agg aag tac aaa aaa gtc cga ttt atg gca tac     1521
Pro Gln Arg Ile Gly Arg Lys Tyr Lys Lys Val Arg Phe Met Ala Tyr
435                  440                  445                  450 aca gat gaa acc ttt aag act cgt gaa gct att cag cat gaa tca gga     1569
Thr Asp Glu Thr Phe Lys Thr Arg Glu Ala Ile Gln His Glu Ser Gly
```

-continued

| | | | | | | | | | | | | | | | | |
|---|---|---|---|---|---|---|---|---|---|---|---|---|---|---|---|---|
| | | | 455 | | | | | 460 | | | | | 465 | | | |
| atc | ttg | gga | cct | tta | ctt | tat | ggg | gaa | gtt | gga | gac | aca | ctg | ttg | att | 1617 |
| Ile | Leu | Gly | Pro | Leu | Leu | Tyr | Gly | Glu | Val | Gly | Asp | Thr | Leu | Leu | Ile | |
| | | | 470 | | | | | 475 | | | | | 480 | | | |
| ata | ttt | aag | aat | caa | gca | agc | aga | cca | tat | aac | atc | tac | cct | cac | gga | 1665 |
| Ile | Phe | Lys | Asn | Gln | Ala | Ser | Arg | Pro | Tyr | Asn | Ile | Tyr | Pro | His | Gly | |
| | | 485 | | | | | 490 | | | | | 495 | | | | |
| atc | act | gat | gtc | cgt | cct | ttg | tat | tca | agg | aga | tta | cca | aaa | ggt | gta | 1713 |
| Ile | Thr | Asp | Val | Arg | Pro | Leu | Tyr | Ser | Arg | Arg | Leu | Pro | Lys | Gly | Val | |
| | 500 | | | | | 505 | | | | | 510 | | | | | |
| aaa | cat | ttg | aag | gat | ttt | cca | att | ctg | cca | gga | gaa | ata | ttc | aaa | tat | 1761 |
| Lys | His | Leu | Lys | Asp | Phe | Pro | Ile | Leu | Pro | Gly | Glu | Ile | Phe | Lys | Tyr | |
| 515 | | | | | 520 | | | | | 525 | | | | | 530 | |
| aaa | tgg | aca | gtg | act | gta | gaa | gat | ggg | cca | act | aaa | tca | gat | cct | cgg | 1809 |
| Lys | Trp | Thr | Val | Thr | Val | Glu | Asp | Gly | Pro | Thr | Lys | Ser | Asp | Pro | Arg | |
| | | | 535 | | | | | 540 | | | | | 545 | | | |
| tgc | ctg | acc | cgc | tat | tac | tct | agt | ttc | gtt | aat | atg | gag | aga | gat | cta | 1857 |
| Cys | Leu | Thr | Arg | Tyr | Tyr | Ser | Ser | Phe | Val | Asn | Met | Glu | Arg | Asp | Leu | |
| | | | 550 | | | | | 555 | | | | | 560 | | | |
| gct | tca | gga | ctc | att | ggc | cct | ctc | ctc | atc | tgc | tac | aaa | gaa | tct | gta | 1905 |
| Ala | Ser | Gly | Leu | Ile | Gly | Pro | Leu | Leu | Ile | Cys | Tyr | Lys | Glu | Ser | Val | |
| | | 565 | | | | | 570 | | | | | 575 | | | | |
| gat | caa | aga | gga | aac | cag | ata | atg | tca | gac | aag | agg | aat | gtc | atc | ctg | 1953 |
| Asp | Gln | Arg | Gly | Asn | Gln | Ile | Met | Ser | Asp | Lys | Arg | Asn | Val | Ile | Leu | |
| | 580 | | | | | 585 | | | | | 590 | | | | | |
| ttt | tct | gta | ttt | gat | gag | aac | cga | agc | tgg | tac | ctc | aca | gag | aat | ata | 2001 |
| Phe | Ser | Val | Phe | Asp | Glu | Asn | Arg | Ser | Trp | Tyr | Leu | Thr | Glu | Asn | Ile | |
| 595 | | | | | 600 | | | | | 605 | | | | | 610 | |
| caa | cgc | ttt | ctc | ccc | aat | cca | gct | gga | gtg | cag | ctt | gag | gat | cca | gag | 2049 |
| Gln | Arg | Phe | Leu | Pro | Asn | Pro | Ala | Gly | Val | Gln | Leu | Glu | Asp | Pro | Glu | |
| | | | 615 | | | | | 620 | | | | | 625 | | | |
| ttc | caa | gcc | tcc | aac | atc | atg | cac | agc | atc | aat | ggc | tat | gtt | ttt | gat | 2097 |
| Phe | Gln | Ala | Ser | Asn | Ile | Met | His | Ser | Ile | Asn | Gly | Tyr | Val | Phe | Asp | |
| | | | 630 | | | | | 635 | | | | | 640 | | | |
| agt | ttg | cag | ttg | tca | gtt | tgt | ttg | cat | gag | gtg | gca | tac | tgg | tac | att | 2145 |
| Ser | Leu | Gln | Leu | Ser | Val | Cys | Leu | His | Glu | Val | Ala | Tyr | Trp | Tyr | Ile | |
| | | 645 | | | | | 650 | | | | | 655 | | | | |
| cta | agc | att | gga | gca | cag | act | gac | ttc | ctt | tct | gtc | ttc | ttc | tct | gga | 2193 |
| Leu | Ser | Ile | Gly | Ala | Gln | Thr | Asp | Phe | Leu | Ser | Val | Phe | Phe | Ser | Gly | |
| | 660 | | | | | 665 | | | | | 670 | | | | | |
| tat | acc | ttc | aaa | cac | aaa | atg | gtc | tat | gaa | gac | aca | ctc | acc | cta | ttc | 2241 |
| Tyr | Thr | Phe | Lys | His | Lys | Met | Val | Tyr | Glu | Asp | Thr | Leu | Thr | Leu | Phe | |
| 675 | | | | | 680 | | | | | 685 | | | | | 690 | |
| cca | ttc | tca | gga | gaa | act | gtc | ttc | atg | tcg | atg | gaa | aac | cca | ggt | cta | 2289 |
| Pro | Phe | Ser | Gly | Glu | Thr | Val | Phe | Met | Ser | Met | Glu | Asn | Pro | Gly | Leu | |
| | | | 695 | | | | | 700 | | | | | 705 | | | |
| tgg | att | ctg | ggg | tgc | cac | aac | tca | gac | ttt | cgg | aac | aga | ggc | atg | acc | 2337 |
| Trp | Ile | Leu | Gly | Cys | His | Asn | Ser | Asp | Phe | Arg | Asn | Arg | Gly | Met | Thr | |
| | | | 710 | | | | | 715 | | | | | 720 | | | |
| gcc | tta | ctg | aag | gtt | tct | agt | tgt | gac | aag | aac | act | ggt | gat | tat | tac | 2385 |
| Ala | Leu | Leu | Lys | Val | Ser | Ser | Cys | Asp | Lys | Asn | Thr | Gly | Asp | Tyr | Tyr | |
| | | 725 | | | | | 730 | | | | | 735 | | | | |
| gag | gac | agt | tat | gaa | gat | att | tca | gca | tac | ttg | ctg | agt | aaa | aac | aat | 2433 |
| Glu | Asp | Ser | Tyr | Glu | Asp | Ile | Ser | Ala | Tyr | Leu | Leu | Ser | Lys | Asn | Asn | |
| | 740 | | | | | 745 | | | | | 750 | | | | | |
| gcc | att | gaa | cca | aga | agc | ttc | tcc | cag | aat | tca | aga | cac | cct | agc | act | 2481 |
| Ala | Ile | Glu | Pro | Arg | Ser | Phe | Ser | Gln | Asn | Ser | Arg | His | Pro | Ser | Thr | |
| 755 | | | | | 760 | | | | | 765 | | | | | 770 | |
| agg | caa | aag | caa | ttt | aat | gcc | acc | aca | att | cca | gaa | aat | gac | ata | gag | 2529 |
| Arg | Gln | Lys | Gln | Phe | Asn | Ala | Thr | Thr | Ile | Pro | Glu | Asn | Asp | Ile | Glu | |

```
                775                 780                 785
aag act gac cct tgg ttt gca cac aga aca cct atg cct aaa ata caa         2577
Lys Thr Asp Pro Trp Phe Ala His Arg Thr Pro Met Pro Lys Ile Gln
            790                 795                 800 aat gtc tcc tct agt gat ttg ttg atg ctc ttg cga cag agt cct act         2625
Asn Val Ser Ser Ser Asp Leu Leu Met Leu Leu Arg Gln Ser Pro Thr
            805                 810                 815 cca cat ggg cta tcc tta tct gat ctc caa gaa gcc aaa tat gag act         2673
Pro His Gly Leu Ser Leu Ser Asp Leu Gln Glu Ala Lys Tyr Glu Thr
            820                 825                 830 ttt tct gat gat cca tca cct gga gca ata gac agt aat aac agc ctg         2721
Phe Ser Asp Asp Pro Ser Pro Gly Ala Ile Asp Ser Asn Asn Ser Leu
835                 840                 845                 850 tct gaa atg aca cac ttc agg cca cag ctc cat cac agt ggg gac atg         2769
Ser Glu Met Thr His Phe Arg Pro Gln Leu His His Ser Gly Asp Met
            855                 860                 865 gta ttt acc cct gag tca ggc ctc caa tta aga tta aat gag aaa ctg         2817
Val Phe Thr Pro Glu Ser Gly Leu Gln Leu Arg Leu Asn Glu Lys Leu
            870                 875                 880 ggg aca act gca gca aca gag ttg aag aaa ctt gat ttc aaa gtt tct         2865
Gly Thr Thr Ala Ala Thr Glu Leu Lys Lys Leu Asp Phe Lys Val Ser
            885                 890                 895 agt aca tca aat aat ctg att tca aca att cca tca gac aat ttg gca         2913
Ser Thr Ser Asn Asn Leu Ile Ser Thr Ile Pro Ser Asp Asn Leu Ala
900                 905                 910 gca ggt act gat aat aca agt tcc tta gga ccc cca agt atg cca gtt         2961
Ala Gly Thr Asp Asn Thr Ser Ser Leu Gly Pro Pro Ser Met Pro Val
915                 920                 925                 930 cat tat gat agt caa tta gat acc act cta ttt ggc aaa aag tca tct         3009
His Tyr Asp Ser Gln Leu Asp Thr Thr Leu Phe Gly Lys Lys Ser Ser
            935                 940                 945 ccc ctt act gag tct ggt gga cct ctg agc ttg agt gaa gaa aat aat         3057
Pro Leu Thr Glu Ser Gly Gly Pro Leu Ser Leu Ser Glu Glu Asn Asn
            950                 955                 960 gat tca aag ttg tta gaa tca ggt tta atg aat agc caa gaa agt tca         3105
Asp Ser Lys Leu Leu Glu Ser Gly Leu Met Asn Ser Gln Glu Ser Ser
            965                 970                 975 tgg gga aaa aat gta tcg tca aca gag agt ggt agg tta ttt aaa ggg         3153
Trp Gly Lys Asn Val Ser Ser Thr Glu Ser Gly Arg Leu Phe Lys Gly
            980                 985                 990 aaa aga gct cat gga cct gct ttg ttg act aaa gat aat gcc tta             3198
Lys Arg Ala His Gly Pro Ala Leu Leu Thr Lys Asp Asn Ala Leu
995                 1000                1005 ttc aaa gtt agc atc tct ttg tta aag aca aac aaa act tcc aat             3243
Phe Lys Val Ser Ile Ser Leu Leu Lys Thr Asn Lys Thr Ser Asn
1010                1015                1020 aat tca gca act aat aga aag act cac att gat ggc cca tca tta             3288
Asn Ser Ala Thr Asn Arg Lys Thr His Ile Asp Gly Pro Ser Leu
1025                1030                1035 tta att gag aat agt cca tca gtc tgg caa aat ata tta gaa agt             3333
Leu Ile Glu Asn Ser Pro Ser Val Trp Gln Asn Ile Leu Glu Ser
1040                1045                1050 gac act gag ttt aaa aaa gtg aca cct ttg att cat gac aga atg             3378
Asp Thr Glu Phe Lys Lys Val Thr Pro Leu Ile His Asp Arg Met
1055                1060                1065 ctt atg gac aaa aat gct aca gct ttg agg cta aat cat atg tca             3423
Leu Met Asp Lys Asn Ala Thr Ala Leu Arg Leu Asn His Met Ser
1070                1075                1080 aat aaa act act tca tca aaa aac atg gaa atg gtc caa cag aaa             3468
Asn Lys Thr Thr Ser Ser Lys Asn Met Glu Met Val Gln Gln Lys
```

|     |     |     |     |     |     |     |     |     |     |     |     |     |     |     |      |
|-----|-----|-----|-----|-----|-----|-----|-----|-----|-----|-----|-----|-----|-----|-----|------|
|     |     |     |     | 1085 |     |     |     |     | 1090 |     |     |     |     | 1095 |      |
| aaa | gag | ggc | ccc | att | cca | cca | gat | gca | caa | aat | cca | gat | atg | tcg | 3513 |
| Lys | Glu | Gly | Pro | Ile | Pro | Pro | Asp | Ala | Gln | Asn | Pro | Asp | Met | Ser |      |
| 1100 |     |     |     |     | 1105 |     |     |     |     | 1110 |     |     |     |     |      |
| ttc | ttt | aag | atg | cta | ttc | ttg | cca | gaa | tca | gca | agg | tgg | ata | caa | 3558 |
| Phe | Phe | Lys | Met | Leu | Phe | Leu | Pro | Glu | Ser | Ala | Arg | Trp | Ile | Gln |      |
| 1115 |     |     |     |     | 1120 |     |     |     |     | 1125 |     |     |     |     |      |
| agg | act | cat | gga | aag | aac | tct | ctg | aac | tct | ggg | caa | ggc | ccc | agt | 3603 |
| Arg | Thr | His | Gly | Lys | Asn | Ser | Leu | Asn | Ser | Gly | Gln | Gly | Pro | Ser |      |
| 1130 |     |     |     |     | 1135 |     |     |     |     | 1140 |     |     |     |     |      |
| cca | aag | caa | tta | gta | tcc | tta | gga | cca | gaa | aaa | tct | gtg | gaa | ggt | 3648 |
| Pro | Lys | Gln | Leu | Val | Ser | Leu | Gly | Pro | Glu | Lys | Ser | Val | Glu | Gly |      |
| 1145 |     |     |     |     | 1150 |     |     |     |     | 1155 |     |     |     |     |      |
| cag | aat | ttc | ttg | tct | gag | aaa | aac | aaa | gtg | gta | gta | gga | aag | ggt | 3693 |
| Gln | Asn | Phe | Leu | Ser | Glu | Lys | Asn | Lys | Val | Val | Val | Gly | Lys | Gly |      |
| 1160 |     |     |     |     | 1165 |     |     |     |     | 1170 |     |     |     |     |      |
| gaa | ttt | aca | aag | gac | gta | gga | ctc | aaa | gag | atg | gtt | ttt | cca | agc | 3738 |
| Glu | Phe | Thr | Lys | Asp | Val | Gly | Leu | Lys | Glu | Met | Val | Phe | Pro | Ser |      |
| 1175 |     |     |     |     | 1180 |     |     |     |     | 1185 |     |     |     |     |      |
| agc | aga | aac | cta | ttt | ctt | act | aac | ttg | gat | aat | tta | cat | gaa | aat | 3783 |
| Ser | Arg | Asn | Leu | Phe | Leu | Thr | Asn | Leu | Asp | Asn | Leu | His | Glu | Asn |      |
| 1190 |     |     |     |     | 1195 |     |     |     |     | 1200 |     |     |     |     |      |
| aat | aca | cac | aat | caa | gaa | aaa | aaa | att | cag | gaa | gaa | ata | gaa | aag | 3828 |
| Asn | Thr | His | Asn | Gln | Glu | Lys | Lys | Ile | Gln | Glu | Glu | Ile | Glu | Lys |      |
| 1205 |     |     |     |     | 1210 |     |     |     |     | 1215 |     |     |     |     |      |
| aag | gaa | aca | tta | atc | caa | gag | aat | gta | gtt | ttg | cct | cag | ata | cat | 3873 |
| Lys | Glu | Thr | Leu | Ile | Gln | Glu | Asn | Val | Val | Leu | Pro | Gln | Ile | His |      |
| 1220 |     |     |     |     | 1225 |     |     |     |     | 1230 |     |     |     |     |      |
| aca | gtg | act | ggc | act | aag | aat | ttc | atg | aag | aac | ctt | ttc | tta | ctg | 3918 |
| Thr | Val | Thr | Gly | Thr | Lys | Asn | Phe | Met | Lys | Asn | Leu | Phe | Leu | Leu |      |
| 1235 |     |     |     |     | 1240 |     |     |     |     | 1245 |     |     |     |     |      |
| agc | act | agg | caa | aat | gta | gaa | ggt | tca | tat | gac | ggg | gca | tat | gct | 3963 |
| Ser | Thr | Arg | Gln | Asn | Val | Glu | Gly | Ser | Tyr | Asp | Gly | Ala | Tyr | Ala |      |
| 1250 |     |     |     |     | 1255 |     |     |     |     | 1260 |     |     |     |     |      |
| cca | gta | ctt | caa | gat | ttt | agg | tca | tta | aat | gat | tca | aca | aat | aga | 4008 |
| Pro | Val | Leu | Gln | Asp | Phe | Arg | Ser | Leu | Asn | Asp | Ser | Thr | Asn | Arg |      |
| 1265 |     |     |     |     | 1270 |     |     |     |     | 1275 |     |     |     |     |      |
| aca | aag | aaa | cac | aca | gct | cat | ttc | tca | aaa | aaa | ggg | gag | gaa | gaa | 4053 |
| Thr | Lys | Lys | His | Thr | Ala | His | Phe | Ser | Lys | Lys | Gly | Glu | Glu | Glu |      |
| 1280 |     |     |     |     | 1285 |     |     |     |     | 1290 |     |     |     |     |      |
| aac | ttg | gaa | ggc | ttg | gga | aat | caa | acc | aag | caa | att | gta | gag | aaa | 4098 |
| Asn | Leu | Glu | Gly | Leu | Gly | Asn | Gln | Thr | Lys | Gln | Ile | Val | Glu | Lys |      |
| 1295 |     |     |     |     | 1300 |     |     |     |     | 1305 |     |     |     |     |      |
| tat | gca | tgc | acc | aca | agg | ata | tct | cct | aat | aca | agc | cag | cag | aat | 4143 |
| Tyr | Ala | Cys | Thr | Thr | Arg | Ile | Ser | Pro | Asn | Thr | Ser | Gln | Gln | Asn |      |
| 1310 |     |     |     |     | 1315 |     |     |     |     | 1320 |     |     |     |     |      |
| ttt | gtc | acg | caa | cgt | agt | aag | aga | gct | ttg | aaa | caa | ttc | aga | ctc | 4188 |
| Phe | Val | Thr | Gln | Arg | Ser | Lys | Arg | Ala | Leu | Lys | Gln | Phe | Arg | Leu |      |
| 1325 |     |     |     |     | 1330 |     |     |     |     | 1335 |     |     |     |     |      |
| cca | cta | gaa | gaa | aca | gaa | ctt | gaa | aaa | agg | ata | att | gtg | gat | gac | 4233 |
| Pro | Leu | Glu | Glu | Thr | Glu | Leu | Glu | Lys | Arg | Ile | Ile | Val | Asp | Asp |      |
| 1340 |     |     |     |     | 1345 |     |     |     |     | 1350 |     |     |     |     |      |
| acc | tca | acc | cag | tgg | tcc | aaa | aac | atg | aaa | cat | ttg | acc | ccg | agc | 4278 |
| Thr | Ser | Thr | Gln | Trp | Ser | Lys | Asn | Met | Lys | His | Leu | Thr | Pro | Ser |      |
| 1355 |     |     |     |     | 1360 |     |     |     |     | 1365 |     |     |     |     |      |
| acc | ctc | aca | cag | ata | gac | tac | aat | gag | aag | gag | aaa | ggg | gcc | att | 4323 |
| Thr | Leu | Thr | Gln | Ile | Asp | Tyr | Asn | Glu | Lys | Glu | Lys | Gly | Ala | Ile |      |
| 1370 |     |     |     |     | 1375 |     |     |     |     | 1380 |     |     |     |     |      |
| act | cag | tct | ccc | tta | tca | gat | tgc | ctt | acg | agg | agt | cat | agc | atc | 4368 |
| Thr | Gln | Ser | Pro | Leu | Ser | Asp | Cys | Leu | Thr | Arg | Ser | His | Ser | Ile |      |

```
                                1385                    1390                    1395
cct   caa   gca   aat   aga   tct   cca   tta   ccc   att   gca   aag   gta   tca   tca        4413
Pro   Gln   Ala   Asn   Arg   Ser   Pro   Leu   Pro   Ile   Ala   Lys   Val   Ser   Ser
1400                    1405                    1410 ttt   cca   tct   att   aga   cct   ata   tat   ctg   acc   agg   gtc   cta   ttc   caa        4458
Phe   Pro   Ser   Ile   Arg   Pro   Ile   Tyr   Leu   Thr   Arg   Val   Leu   Phe   Gln
1415                    1420                    1425 gac   aac   tct   tct   cat   ctt   cca   gca   gca   tct   tat   aga   aag   aaa   gat        4503
Asp   Asn   Ser   Ser   His   Leu   Pro   Ala   Ala   Ser   Tyr   Arg   Lys   Lys   Asp
1430                    1435                    1440 tct   ggg   gtc   caa   gaa   agc   agt   cat   ttc   tta   caa   gga   gcc   aaa   aaa        4548
Ser   Gly   Val   Gln   Glu   Ser   Ser   His   Phe   Leu   Gln   Gly   Ala   Lys   Lys
1445                    1450                    1455 aat   aac   ctt   tct   tta   gcc   att   cta   acc   ttg   gag   atg   act   ggt   gat        4593
Asn   Asn   Leu   Ser   Leu   Ala   Ile   Leu   Thr   Leu   Glu   Met   Thr   Gly   Asp
1460                    1465                    1470 caa   aga   gag   gtt   ggc   tcc   ctg   ggg   aca   agt   gcc   aca   aat   tca   gtc        4638
Gln   Arg   Glu   Val   Gly   Ser   Leu   Gly   Thr   Ser   Ala   Thr   Asn   Ser   Val
1475                    1480                    1485 aca   tac   aag   aaa   gtt   gag   aac   act   gtt   ctc   ccg   aaa   cca   gac   ttg        4683
Thr   Tyr   Lys   Lys   Val   Glu   Asn   Thr   Val   Leu   Pro   Lys   Pro   Asp   Leu
1490                    1495                    1500 ccc   aaa   aca   tct   ggc   aaa   gtt   gaa   ttg   ctt   cca   aaa   gtt   cac   att        4728
Pro   Lys   Thr   Ser   Gly   Lys   Val   Glu   Leu   Leu   Pro   Lys   Val   His   Ile
1505                    1510                    1515 tat   cag   aag   gac   cta   ttc   cct   acg   gaa   act   agc   aat   ggg   tct   cct        4773
Tyr   Gln   Lys   Asp   Leu   Phe   Pro   Thr   Glu   Thr   Ser   Asn   Gly   Ser   Pro
1520                    1525                    1530 ggc   cat   ctg   gat   ctc   gtg   gaa   ggg   agc   ctt   ctt   cag   gga   aca   gag        4818
Gly   His   Leu   Asp   Leu   Val   Glu   Gly   Ser   Leu   Leu   Gln   Gly   Thr   Glu
1535                    1540                    1545 gga   gcg   att   aag   tgg   aat   gaa   gca   aac   aga   cct   gga   aaa   gtt   ccc        4863
Gly   Ala   Ile   Lys   Trp   Asn   Glu   Ala   Asn   Arg   Pro   Gly   Lys   Val   Pro
1550                    1555                    1560 ttt   ctg   aga   gta   gca   aca   gaa   agc   tct   gca   aag   act   ccc   tcc   aag        4908
Phe   Leu   Arg   Val   Ala   Thr   Glu   Ser   Ser   Ala   Lys   Thr   Pro   Ser   Lys
1565                    1570                    1575 cta   ttg   gat   cct   ctt   gct   tgg   gat   aac   cac   tat   ggt   act   cag   ata        4953
Leu   Leu   Asp   Pro   Leu   Ala   Trp   Asp   Asn   His   Tyr   Gly   Thr   Gln   Ile
1580                    1585                    1590 cca   aaa   gaa   gag   tgg   aaa   tcc   caa   gag   aag   tca   cca   gaa   aaa   aca        4998
Pro   Lys   Glu   Glu   Trp   Lys   Ser   Gln   Glu   Lys   Ser   Pro   Glu   Lys   Thr
1595                    1600                    1605 gct   ttt   aag   aaa   aag   gat   acc   att   ttg   tcc   ctg   aac   gct   tgt   gaa        5043
Ala   Phe   Lys   Lys   Lys   Asp   Thr   Ile   Leu   Ser   Leu   Asn   Ala   Cys   Glu
1610                    1615                    1620 agc   aat   cat   gca   ata   gca   gca   ata   aat   gag   gga   caa   aat   aag   ccc        5088
Ser   Asn   His   Ala   Ile   Ala   Ala   Ile   Asn   Glu   Gly   Gln   Asn   Lys   Pro
1625                    1630                    1635 gaa   ata   gaa   gtc   acc   tgg   gca   aag   caa   ggt   agg   act   gaa   agg   ctg        5133
Glu   Ile   Glu   Val   Thr   Trp   Ala   Lys   Gln   Gly   Arg   Thr   Glu   Arg   Leu
1640                    1645                    1650 tgc   tct   caa   aac   cca   cca   gtc   ttg   aaa   cgc   cat   caa   cgg   gaa   ata        5178
Cys   Ser   Gln   Asn   Pro   Pro   Val   Leu   Lys   Arg   His   Gln   Arg   Glu   Ile
1655                    1660                    1665 act   cgt   act   act   ctt   cag   tca   gat   caa   gag   gaa   att   gac   tat   gat        5223
Thr   Arg   Thr   Thr   Leu   Gln   Ser   Asp   Gln   Glu   Glu   Ile   Asp   Tyr   Asp
1670                    1675                    1680 gat   acc   ata   tca   gtt   gaa   atg   aag   aag   gaa   gat   ttt   gac   att   tat        5268
Asp   Thr   Ile   Ser   Val   Glu   Met   Lys   Lys   Glu   Asp   Phe   Asp   Ile   Tyr
```

-continued

|  |  |  |  |  |
|---|---|---|---|---|
| | 1685 | 1690 | 1695 | |
| gat gag gat gaa aat cag agc ccc cgc agc ttt caa aag aaa aca<br>Asp Glu Asp Glu Asn Gln Ser Pro Arg Ser Phe Gln Lys Lys Thr<br>1700 1705 1710 | | | | 5313 |
| cga cac tat ttt att gct gca gtg gag agg ctc tgg gat tat ggg<br>Arg His Tyr Phe Ile Ala Ala Val Glu Arg Leu Trp Asp Tyr Gly<br>1715 1720 1725 | | | | 5358 |
| atg agt agc tcc cca cat gtt cta aga aac agg gct cag agt ggc<br>Met Ser Ser Ser Pro His Val Leu Arg Asn Arg Ala Gln Ser Gly<br>1730 1735 1740 | | | | 5403 |
| agt gtc cct cag ttc aag aaa gtt gtt ttc cag gaa ttt act gat<br>Ser Val Pro Gln Phe Lys Lys Val Val Phe Gln Glu Phe Thr Asp<br>1745 1750 1755 | | | | 5448 |
| ggc tcc ttt act cag ccc tta tac cgt gga gaa cta aat gaa cat<br>Gly Ser Phe Thr Gln Pro Leu Tyr Arg Gly Glu Leu Asn Glu His<br>1760 1765 1770 | | | | 5493 |
| ttg gga ctc ctg ggg cca tat ata aga gca gaa gtt gaa gat aat<br>Leu Gly Leu Leu Gly Pro Tyr Ile Arg Ala Glu Val Glu Asp Asn<br>1775 1780 1785 | | | | 5538 |
| atc atg gta act ttc aga aat cag gcc tct cgt ccc tat tcc ttc<br>Ile Met Val Thr Phe Arg Asn Gln Ala Ser Arg Pro Tyr Ser Phe<br>1790 1795 1800 | | | | 5583 |
| tat tct agc ctt att tct tat gag gaa gat cag agg caa gga gca<br>Tyr Ser Ser Leu Ile Ser Tyr Glu Glu Asp Gln Arg Gln Gly Ala<br>1805 1810 1815 | | | | 5628 |
| gaa cct aga aaa aac ttt gtc aag cct aat gaa acc aaa act tac<br>Glu Pro Arg Lys Asn Phe Val Lys Pro Asn Glu Thr Lys Thr Tyr<br>1820 1825 1830 | | | | 5673 |
| ttt tgg aaa gtg caa cat cat atg gca ccc act aaa gat gag ttt<br>Phe Trp Lys Val Gln His His Met Ala Pro Thr Lys Asp Glu Phe<br>1835 1840 1845 | | | | 5718 |
| gac tgc aaa gcc tgg gct tat ttc tct gat gtt gac ctg gaa aaa<br>Asp Cys Lys Ala Trp Ala Tyr Phe Ser Asp Val Asp Leu Glu Lys<br>1850 1855 1860 | | | | 5763 |
| gat gtg cac tca ggc ctg att gga ccc ctt ctg gtc tgc cac act<br>Asp Val His Ser Gly Leu Ile Gly Pro Leu Leu Val Cys His Thr<br>1865 1870 1875 | | | | 5808 |
| aac aca ctg aac cct gct cat ggg aga caa gtg aca gta cag gaa<br>Asn Thr Leu Asn Pro Ala His Gly Arg Gln Val Thr Val Gln Glu<br>1880 1885 1890 | | | | 5853 |
| ttt gct ctg ttt ttc acc atc ttt gat gag acc aaa agc tgg tac<br>Phe Ala Leu Phe Phe Thr Ile Phe Asp Glu Thr Lys Ser Trp Tyr<br>1895 1900 1905 | | | | 5898 |
| ttc act gaa aat atg gaa aga aac tgc agg gct ccc tgc aat atc<br>Phe Thr Glu Asn Met Glu Arg Asn Cys Arg Ala Pro Cys Asn Ile<br>1910 1915 1920 | | | | 5943 |
| cag atg gaa gat ccc act ttt aaa gag aat tat cgc ttc cat gca<br>Gln Met Glu Asp Pro Thr Phe Lys Glu Asn Tyr Arg Phe His Ala<br>1925 1930 1935 | | | | 5988 |
| atc aat ggc tac ata atg gat aca cta cct ggc tta gta atg gct<br>Ile Asn Gly Tyr Ile Met Asp Thr Leu Pro Gly Leu Val Met Ala<br>1940 1945 1950 | | | | 6033 |
| cag gat caa agg att cga tgg tat ctg ctc agc atg ggc agc aat<br>Gln Asp Gln Arg Ile Arg Trp Tyr Leu Leu Ser Met Gly Ser Asn<br>1955 1960 1965 | | | | 6078 |
| gaa aac atc cat tct att cat ttc agt gga cat gtg ttc act gta<br>Glu Asn Ile His Ser Ile His Phe Ser Gly His Val Phe Thr Val<br>1970 1975 1980 | | | | 6123 |
| cga aaa aaa gag gag tat aaa atg gca ctg tac aat ctc tat cca<br>Arg Lys Lys Glu Glu Tyr Lys Met Ala Leu Tyr Asn Leu Tyr Pro | | | | 6168 |

| | | | | | | | | | | |
|---|---|---|---|---|---|---|---|---|---|---|
| | | 1985 | | | 1990 | | | 1995 | | |
| ggt | gtt | ttt | gag | aca | gtg | gaa | atg | tta | cca | tcc | aaa | gct | gga | att | 6213 |
| Gly | Val | Phe | Glu | Thr | Val | Glu | Met | Leu | Pro | Ser | Lys | Ala | Gly | Ile | |
| 2000 | | | | | 2005 | | | | | 2010 | | | | | |
| tgg | cgg | gtg | gaa | tgc | ctt | att | ggc | gag | cat | cta | cat | gct | ggg | atg | 6258 |
| Trp | Arg | Val | Glu | Cys | Leu | Ile | Gly | Glu | His | Leu | His | Ala | Gly | Met | |
| 2015 | | | | | 2020 | | | | | 2025 | | | | | |
| agc | aca | ctt | ttt | ctg | gtg | tac | agc | aat | aag | tgt | cag | act | ccc | ctg | 6303 |
| Ser | Thr | Leu | Phe | Leu | Val | Tyr | Ser | Asn | Lys | Cys | Gln | Thr | Pro | Leu | |
| 2030 | | | | | 2035 | | | | | 2040 | | | | | |
| gga | atg | gct | tct | gga | cac | att | aga | gat | ttt | cag | att | aca | gct | tca | 6348 |
| Gly | Met | Ala | Ser | Gly | His | Ile | Arg | Asp | Phe | Gln | Ile | Thr | Ala | Ser | |
| 2045 | | | | | 2050 | | | | | 2055 | | | | | |
| gga | caa | tat | gga | cag | tgg | gcc | cca | aag | ctg | gcc | aga | ctt | cat | tat | 6393 |
| Gly | Gln | Tyr | Gly | Gln | Trp | Ala | Pro | Lys | Leu | Ala | Arg | Leu | His | Tyr | |
| 2060 | | | | | 2065 | | | | | 2070 | | | | | |
| tcc | gga | tca | atc | aat | gcc | tgg | agc | acc | aag | gag | ccc | ttt | tct | tgg | 6438 |
| Ser | Gly | Ser | Ile | Asn | Ala | Trp | Ser | Thr | Lys | Glu | Pro | Phe | Ser | Trp | |
| 2075 | | | | | 2080 | | | | | 2085 | | | | | |
| atc | aag | gtg | gat | ctg | ttg | gca | cca | atg | att | att | cac | ggc | atc | aag | 6483 |
| Ile | Lys | Val | Asp | Leu | Leu | Ala | Pro | Met | Ile | Ile | His | Gly | Ile | Lys | |
| 2090 | | | | | 2095 | | | | | 2100 | | | | | |
| acc | cag | ggt | gcc | cgt | cag | aag | ttc | tcc | agc | ctc | tac | atc | tct | cag | 6528 |
| Thr | Gln | Gly | Ala | Arg | Gln | Lys | Phe | Ser | Ser | Leu | Tyr | Ile | Ser | Gln | |
| 2105 | | | | | 2110 | | | | | 2115 | | | | | |
| ttt | atc | atc | atg | tat | agt | ctt | gat | ggg | aag | aag | tgg | cag | act | tat | 6573 |
| Phe | Ile | Ile | Met | Tyr | Ser | Leu | Asp | Gly | Lys | Lys | Trp | Gln | Thr | Tyr | |
| 2120 | | | | | 2125 | | | | | 2130 | | | | | |
| cga | gga | aat | tcc | act | gga | acc | tta | atg | gtc | ttc | ttt | ggc | aat | gtg | 6618 |
| Arg | Gly | Asn | Ser | Thr | Gly | Thr | Leu | Met | Val | Phe | Phe | Gly | Asn | Val | |
| 2135 | | | | | 2140 | | | | | 2145 | | | | | |
| gat | tca | tct | ggg | ata | aaa | cac | aat | att | ttt | aac | cct | cca | att | att | 6663 |
| Asp | Ser | Ser | Gly | Ile | Lys | His | Asn | Ile | Phe | Asn | Pro | Pro | Ile | Ile | |
| 2150 | | | | | 2155 | | | | | 2160 | | | | | |
| gct | cga | tac | atc | cgt | ttg | cac | cca | act | cat | tat | agc | att | cgc | agc | 6708 |
| Ala | Arg | Tyr | Ile | Arg | Leu | His | Pro | Thr | His | Tyr | Ser | Ile | Arg | Ser | |
| 2165 | | | | | 2170 | | | | | 2175 | | | | | |
| act | ctt | cgc | atg | gag | ttg | atg | ggc | tgt | gat | tta | aat | agt | tgc | agc | 6753 |
| Thr | Leu | Arg | Met | Glu | Leu | Met | Gly | Cys | Asp | Leu | Asn | Ser | Cys | Ser | |
| 2180 | | | | | 2185 | | | | | 2190 | | | | | |
| atg | cca | ttg | gga | atg | gag | agt | aaa | gca | ata | tca | gat | gca | cag | att | 6798 |
| Met | Pro | Leu | Gly | Met | Glu | Ser | Lys | Ala | Ile | Ser | Asp | Ala | Gln | Ile | |
| 2195 | | | | | 2200 | | | | | 2205 | | | | | |
| act | gct | tca | tcc | tac | ttt | acc | aat | atg | ttt | gcc | acc | tgg | tct | cct | 6843 |
| Thr | Ala | Ser | Ser | Tyr | Phe | Thr | Asn | Met | Phe | Ala | Thr | Trp | Ser | Pro | |
| 2210 | | | | | 2215 | | | | | 2220 | | | | | |
| tca | aaa | gct | cga | ctt | cac | ctc | caa | ggg | agg | agt | aat | gcc | tgg | aga | 6888 |
| Ser | Lys | Ala | Arg | Leu | His | Leu | Gln | Gly | Arg | Ser | Asn | Ala | Trp | Arg | |
| 2225 | | | | | 2230 | | | | | 2235 | | | | | |
| cct | cag | gtg | aat | aat | cca | aaa | gag | tgg | ctg | caa | gtg | gac | ttc | cag | 6933 |
| Pro | Gln | Val | Asn | Asn | Pro | Lys | Glu | Trp | Leu | Gln | Val | Asp | Phe | Gln | |
| 2240 | | | | | 2245 | | | | | 2250 | | | | | |
| aag | aca | atg | aaa | gtc | aca | gga | gta | act | act | cag | gga | gta | aaa | tct | 6978 |
| Lys | Thr | Met | Lys | Val | Thr | Gly | Val | Thr | Thr | Gln | Gly | Val | Lys | Ser | |
| 2255 | | | | | 2260 | | | | | 2265 | | | | | |
| ctg | ctt | acc | agc | atg | tat | gtg | aag | gag | ttc | ctc | atc | tcc | agc | agt | 7023 |
| Leu | Leu | Thr | Ser | Met | Tyr | Val | Lys | Glu | Phe | Leu | Ile | Ser | Ser | Ser | |
| 2270 | | | | | 2275 | | | | | 2280 | | | | | |
| caa | gat | ggc | cat | cag | tgg | act | ctc | ttt | ttt | cag | aat | ggc | aaa | gta | 7068 |
| Gln | Asp | Gly | His | Gln | Trp | Thr | Leu | Phe | Phe | Gln | Asn | Gly | Lys | Val | |

|  |  |  |  |  |  |  |  |  |  |  |
|---|---|---|---|---|---|---|---|---|---|---|
| 2285 | | | | 2290 | | | | 2295 | | |
| aag | gtt | ttt | cag | gga | aat | caa | gac | tcc | ttc | aca | cct | gtg | gtg | aac | 7113 |
| Lys | Val | Phe | Gln | Gly | Asn | Gln | Asp | Ser | Phe | Thr | Pro | Val | Val | Asn | |
| 2300 | | | | 2305 | | | | 2310 | | | | | | | |
| tct | cta | gac | cca | ccg | tta | ctg | act | cgc | tac | ctt | cga | att | cac | ccc | 7158 |
| Ser | Leu | Asp | Pro | Pro | Leu | Leu | Thr | Arg | Tyr | Leu | Arg | Ile | His | Pro | |
| 2315 | | | | 2320 | | | | 2325 | | | | | | | |
| cag | agt | tgg | gtg | cac | cag | att | gcc | ctg | agg | atg | gag | gtt | ctg | ggc | 7203 |
| Gln | Ser | Trp | Val | His | Gln | Ile | Ala | Leu | Arg | Met | Glu | Val | Leu | Gly | |
| 2330 | | | | 2335 | | | | 2340 | | | | | | | |
| tgc | gag | gca | cag | gac | ctc | tac | tga gggtggccac tgcagcacct | | | | | | | | 7247 |
| Cys | Glu | Ala | Gln | Asp | Leu | Tyr | | | | | | | | | |
| 2345 | | | | 2350 | | | | | | | | | | | | gccactgccg tcacctctcc ctcctcagct ccagggcagt gtccctccct ggcttgcctt  7307 ctacctttgt gctaaatcct agcagacact gccttgaagc ctcctgaatt aactatcatc  7367 agtcctgcat ttctttggtg gggggccagg agggtgcatc caatttaact taactcttac  7427 ctattttctg cagctgctcc cagattactc cttccttcca atataactag gcaaaaagaa  7487 gtgaggagaa acctgcatga aagcattctt ccctgaaaag ttaggcctct cagagtcacc  7547 acttcctctg ttgtagaaaa actatgtgat gaaactttga aaagatatt tatgatgtta  7607 acatttcagg ttaagcctca tacgtttaaa ataaaactct cagttgttta ttatcctgat  7667 caagcatgga acaaagcatg tttcaggatc agatcaatac aatcttggag tcaaaaggca  7727 aatcatttgg acaatctgca aaatggagag aatacaataa ctactacagt aaagtctgtt  7787 tctgcttcct tacacataga tataattatg ttatttagtc attatgaggg gcacattctt  7847 atctccaaaa ctagcattct taaactgaga attatagatg gggttcaaga atccctaagt  7907 cccctgaaat tatataaggc attctgtata aatgcaaatg tgcattttc tgacgagtgt  7967 ccatagatat aaagccattt ggtcttaatt ctgaccaata aaaaaataag tcaggaggat  8027 gcaattgttg aaagctttga aataaaataa caatgtcttc ttgaaatttg tgatggccaa  8087 gaaagaaaat gatgatgaca ttaggcttct aaaggacata catttaatat ttctgtggaa  8147 atatgaggaa atccatggt tatctgagat aggagataca aactttgtaa ttctaataat  8207 gcactcagtt tactctctcc ctctactaat ttcctgctga aaataacaca acaaaaatgt  8267 aacaggggaa attatatacc gtgactgaaa actagagtcc tacttacata gttgaaatat  8327 caaggaggtc agaagaaaat tggactggtg aaaacagaaa aaacactcca gtctgccata  8387 tcaccacaca ataggatccc ccttcttgcc ctccacccc ataagattgt gaagggttta  8447 ctgctccttc catctgcctg accccttcac tatgactaca cagaatctcc tgatagtaaa  8507 gggggctgga ggcaaggata agttatagag cagttggagg aagcatccaa agattgcaac  8567 ccagggcaaa tggaaaacag gagatcctaa tatgaaagaa aaatggatcc caatctgaga  8627 aaaggcaaaa gaatggctac tttttttctat gctggagtat tttctaataa tcctgcttga  8687 cccttatctg acctctttgg aaactataac atagctgtca cagtatagtc acaatccaca  8747 aatgatgcag gtgcaaatgg tttatagccc tgtgaagttc ttaaagttta gaggctaact  8807 tacagaaatg aataagttgt tttgttttat agcccggtag aggagttaac cccaaaggtg  8867 atatggtttt atttcctgtt atgtttaact tgataatctt attttggcat tcttttccca  8927 ttgactatat acatctctat ttctcaaatg ttcatggaac tagctctttt attttcctgc  8987 tggtttcttc agtaatgagt taaataaaac attgacacat a  9028

<210> SEQ ID NO 2

-continued

```
<211> LENGTH: 2351
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Met | Gln | Ile | Glu | Leu | Ser | Thr | Cys | Phe | Phe | Leu | Cys | Leu | Leu | Arg | Phe |
| 1 | | | | 5 | | | | | 10 | | | | | 15 | |
| Cys | Phe | Ser | Ala | Thr | Arg | Arg | Tyr | Tyr | Leu | Gly | Ala | Val | Glu | Leu | Ser |
| | | | 20 | | | | | 25 | | | | | 30 | | |
| Trp | Asp | Tyr | Met | Gln | Ser | Asp | Leu | Gly | Glu | Leu | Pro | Val | Asp | Ala | Arg |
| | | | 35 | | | | | 40 | | | | | 45 | | |
| Phe | Pro | Pro | Arg | Val | Pro | Lys | Ser | Phe | Pro | Phe | Asn | Thr | Ser | Val | Val |
| | 50 | | | | | 55 | | | | | 60 | | | | |
| Tyr | Lys | Lys | Thr | Leu | Phe | Val | Glu | Phe | Thr | Asp | His | Leu | Phe | Asn | Ile |
| 65 | | | | | 70 | | | | | 75 | | | | | 80 |
| Ala | Lys | Pro | Arg | Pro | Pro | Trp | Met | Gly | Leu | Leu | Gly | Pro | Thr | Ile | Gln |
| | | | | 85 | | | | | 90 | | | | | 95 | |
| Ala | Glu | Val | Tyr | Asp | Thr | Val | Val | Ile | Thr | Leu | Lys | Asn | Met | Ala | Ser |
| | | | 100 | | | | | 105 | | | | | 110 | | |
| His | Pro | Val | Ser | Leu | His | Ala | Val | Gly | Val | Ser | Tyr | Trp | Lys | Ala | Ser |
| | | | | 115 | | | | | 120 | | | | | 125 | |
| Glu | Gly | Ala | Glu | Tyr | Asp | Asp | Gln | Thr | Ser | Gln | Arg | Glu | Lys | Glu | Asp |
| | 130 | | | | | 135 | | | | | 140 | | | | |
| Asp | Lys | Val | Phe | Pro | Gly | Gly | Ser | His | Thr | Tyr | Val | Trp | Gln | Val | Leu |
| 145 | | | | | 150 | | | | | 155 | | | | | 160 |
| Lys | Glu | Asn | Gly | Pro | Met | Ala | Ser | Asp | Pro | Leu | Cys | Leu | Thr | Tyr | Ser |
| | | | | 165 | | | | | 170 | | | | | 175 | |
| Tyr | Leu | Ser | His | Val | Asp | Leu | Val | Lys | Asp | Leu | Asn | Ser | Gly | Leu | Ile |
| | | | 180 | | | | | 185 | | | | | 190 | | |
| Gly | Ala | Leu | Leu | Val | Cys | Arg | Glu | Gly | Ser | Leu | Ala | Lys | Glu | Lys | Thr |
| | | | | 195 | | | | | 200 | | | | | 205 | |
| Gln | Thr | Leu | His | Lys | Phe | Ile | Leu | Leu | Phe | Ala | Val | Phe | Asp | Glu | Gly |
| | 210 | | | | | 215 | | | | | 220 | | | | |
| Lys | Ser | Trp | His | Ser | Glu | Thr | Lys | Asn | Ser | Leu | Met | Gln | Asp | Arg | Asp |
| 225 | | | | | 230 | | | | | 235 | | | | | 240 |
| Ala | Ala | Ser | Ala | Arg | Ala | Trp | Pro | Lys | Met | His | Thr | Val | Asn | Gly | Tyr |
| | | | | 245 | | | | | 250 | | | | | 255 | |
| Val | Asn | Arg | Ser | Leu | Pro | Gly | Leu | Ile | Gly | Cys | His | Arg | Lys | Ser | Val |
| | | | 260 | | | | | 265 | | | | | 270 | | |
| Tyr | Trp | His | Val | Ile | Gly | Met | Gly | Thr | Thr | Pro | Glu | Val | His | Ser | Ile |
| | | | | 275 | | | | | 280 | | | | | 285 | |
| Phe | Leu | Glu | Gly | His | Thr | Phe | Leu | Val | Arg | Asn | His | Arg | Gln | Ala | Ser |
| | 290 | | | | | 295 | | | | | 300 | | | | |
| Leu | Glu | Ile | Ser | Pro | Ile | Thr | Phe | Leu | Thr | Ala | Gln | Thr | Leu | Leu | Met |
| 305 | | | | | 310 | | | | | 315 | | | | | 320 |
| Asp | Leu | Gly | Gln | Phe | Leu | Leu | Phe | Cys | His | Ile | Ser | Ser | His | Gln | His |
| | | | | 325 | | | | | 330 | | | | | 335 | |
| Asp | Gly | Met | Glu | Ala | Tyr | Val | Lys | Val | Asp | Ser | Cys | Pro | Glu | Glu | Pro |
| | | | 340 | | | | | 345 | | | | | 350 | | |
| Gln | Leu | Arg | Met | Lys | Asn | Asn | Glu | Glu | Ala | Glu | Asp | Tyr | Asp | Asp | Asp |
| | | | | 355 | | | | | 360 | | | | | 365 | |
| Leu | Thr | Asp | Ser | Glu | Met | Asp | Val | Val | Arg | Phe | Asp | Asp | Asp | Asn | Ser |
| | 370 | | | | | 375 | | | | | 380 | | | | |
| Pro | Ser | Phe | Ile | Gln | Ile | Arg | Ser | Val | Ala | Lys | Lys | His | Pro | Lys | Thr |
| 385 | | | | | 390 | | | | | 395 | | | | | 400 |

```
Trp Val His Tyr Ile Ala Ala Glu Glu Asp Trp Asp Tyr Ala Pro
            405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Val Arg Phe Met
            435                 440                 445

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
            770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
```

-continued

```
            820                 825                 830
Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
            850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
            885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
            930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
            965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
            995                 1000                1005

Leu Phe Lys Val Ser Ile Ser Leu Leu Lys Thr Asn Lys Thr Ser
        1010                1015                1020

Asn Asn Ser Ala Thr Asn Arg Lys Thr His Ile Asp Gly Pro Ser
        1025                1030                1035

Leu Leu Ile Glu Asn Ser Pro Ser Val Trp Gln Asn Ile Leu Glu
        1040                1045                1050

Ser Asp Thr Glu Phe Lys Lys Val Thr Pro Leu Ile His Asp Arg
        1055                1060                1065

Met Leu Met Asp Lys Asn Ala Thr Ala Leu Arg Leu Asn His Met
        1070                1075                1080

Ser Asn Lys Thr Thr Ser Ser Lys Asn Met Glu Met Val Gln Gln
        1085                1090                1095

Lys Lys Glu Gly Pro Ile Pro Pro Asp Ala Gln Asn Pro Asp Met
        1100                1105                1110

Ser Phe Phe Lys Met Leu Phe Leu Pro Glu Ser Ala Arg Trp Ile
        1115                1120                1125

Gln Arg Thr His Gly Lys Asn Ser Leu Asn Ser Gly Gln Gly Pro
        1130                1135                1140

Ser Pro Lys Gln Leu Val Ser Leu Gly Pro Glu Lys Ser Val Glu
        1145                1150                1155

Gly Gln Asn Phe Leu Ser Glu Lys Asn Lys Val Val Val Gly Lys
        1160                1165                1170

Gly Glu Phe Thr Lys Asp Val Gly Leu Lys Glu Met Val Phe Pro
        1175                1180                1185

Ser Ser Arg Asn Leu Phe Leu Thr Asn Leu Asp Asn Leu His Glu
        1190                1195                1200

Asn Asn Thr His Asn Gln Glu Lys Lys Ile Gln Glu Glu Ile Glu
        1205                1210                1215

Lys Lys Glu Thr Leu Ile Gln Glu Asn Val Val Leu Pro Gln Ile
        1220                1225                1230
```

-continued

His Thr Val Thr Gly Thr Lys Asn Phe Met Lys Asn Leu Phe Leu
1235                1240                1245

Leu Ser Thr Arg Gln Asn Val Glu Gly Ser Tyr Asp Gly Ala Tyr
1250                1255                1260

Ala Pro Val Leu Gln Asp Phe Arg Ser Leu Asn Asp Ser Thr Asn
1265                1270                1275

Arg Thr Lys Lys His Thr Ala His Phe Ser Lys Lys Gly Glu Glu
1280                1285                1290

Glu Asn Leu Glu Gly Leu Gly Asn Gln Thr Lys Gln Ile Val Glu
1295                1300                1305

Lys Tyr Ala Cys Thr Thr Arg Ile Ser Pro Asn Thr Ser Gln Gln
1310                1315                1320

Asn Phe Val Thr Gln Arg Ser Lys Arg Ala Leu Lys Gln Phe Arg
1325                1330                1335

Leu Pro Leu Glu Glu Thr Glu Leu Glu Lys Arg Ile Ile Val Asp
1340                1345                1350

Asp Thr Ser Thr Gln Trp Ser Lys Asn Met Lys His Leu Thr Pro
1355                1360                1365

Ser Thr Leu Thr Gln Ile Asp Tyr Asn Glu Lys Glu Lys Gly Ala
1370                1375                1380

Ile Thr Gln Ser Pro Leu Ser Asp Cys Leu Thr Arg Ser His Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425

Gln Asp Asn Ser Ser His Leu Pro Ala Ala Ser Tyr Arg Lys Lys
1430                1435                1440

Asp Ser Gly Val Gln Glu Ser Ser His Phe Leu Gln Gly Ala Lys
1445                1450                1455

Lys Asn Asn Leu Ser Leu Ala Ile Leu Thr Leu Glu Met Thr Gly
1460                1465                1470

Asp Gln Arg Glu Val Gly Ser Leu Gly Thr Ser Ala Thr Asn Ser
1475                1480                1485

Val Thr Tyr Lys Lys Val Glu Asn Thr Val Leu Pro Lys Pro Asp
1490                1495                1500

Leu Pro Lys Thr Ser Gly Lys Val Glu Leu Leu Pro Lys Val His
1505                1510                1515

Ile Tyr Gln Lys Asp Leu Phe Pro Thr Glu Thr Ser Asn Gly Ser
1520                1525                1530

Pro Gly His Leu Asp Leu Val Glu Gly Ser Leu Leu Gln Gly Thr
1535                1540                1545

Glu Gly Ala Ile Lys Trp Asn Glu Ala Asn Arg Pro Gly Lys Val
1550                1555                1560

Pro Phe Leu Arg Val Ala Thr Glu Ser Ser Ala Lys Thr Pro Ser
1565                1570                1575

Lys Leu Leu Asp Pro Leu Ala Trp Asp Asn His Tyr Gly Thr Gln
1580                1585                1590

Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ala Ile Asn Glu Gly Gln Asn Lys
1625                1630                1635

```
Pro Glu Ile Glu Val Thr Trp Ala Lys Gln Gly Arg Thr Glu Arg
    1640            1645            1650

Leu Cys Ser Gln Asn Pro Pro Val Leu Lys Arg His Gln Arg Glu
    1655            1660            1665

Ile Thr Arg Thr Thr Leu Gln Ser Asp Gln Glu Glu Ile Asp Tyr
    1670            1675            1680

Asp Asp Thr Ile Ser Val Glu Met Lys Lys Glu Asp Phe Asp Ile
    1685            1690            1695

Tyr Asp Glu Asp Glu Asn Gln Ser Pro Arg Ser Phe Gln Lys Lys
    1700            1705            1710

Thr Arg His Tyr Phe Ile Ala Ala Val Glu Arg Leu Trp Asp Tyr
    1715            1720            1725

Gly Met Ser Ser Ser Pro His Val Leu Arg Asn Arg Ala Gln Ser
    1730            1735            1740

Gly Ser Val Pro Gln Phe Lys Lys Val Val Phe Gln Glu Phe Thr
    1745            1750            1755

Asp Gly Ser Phe Thr Gln Pro Leu Tyr Arg Gly Glu Leu Asn Glu
    1760            1765            1770

His Leu Gly Leu Leu Gly Pro Tyr Ile Arg Ala Glu Val Glu Asp
    1775            1780            1785

Asn Ile Met Val Thr Phe Arg Asn Gln Ala Ser Arg Pro Tyr Ser
    1790            1795            1800

Phe Tyr Ser Ser Leu Ile Ser Tyr Glu Glu Asp Gln Arg Gln Gly
    1805            1810            1815

Ala Glu Pro Arg Lys Asn Phe Val Lys Pro Asn Glu Thr Lys Thr
    1820            1825            1830

Tyr Phe Trp Lys Val Gln His His Met Ala Pro Thr Lys Asp Glu
    1835            1840            1845

Phe Asp Cys Lys Ala Trp Ala Tyr Phe Ser Asp Val Asp Leu Glu
    1850            1855            1860

Lys Asp Val His Ser Gly Leu Ile Gly Pro Leu Leu Val Cys His
    1865            1870            1875

Thr Asn Thr Leu Asn Pro Ala His Gly Arg Gln Val Thr Val Gln
    1880            1885            1890

Glu Phe Ala Leu Phe Phe Thr Ile Phe Asp Glu Thr Lys Ser Trp
    1895            1900            1905

Tyr Phe Thr Glu Asn Met Glu Arg Asn Cys Arg Ala Pro Cys Asn
    1910            1915            1920

Ile Gln Met Glu Asp Pro Thr Phe Lys Glu Asn Tyr Arg Phe His
    1925            1930            1935

Ala Ile Asn Gly Tyr Ile Met Asp Thr Leu Pro Gly Leu Val Met
    1940            1945            1950

Ala Gln Asp Gln Arg Ile Arg Trp Tyr Leu Leu Ser Met Gly Ser
    1955            1960            1965

Asn Glu Asn Ile His Ser Ile His Phe Ser Gly His Val Phe Thr
    1970            1975            1980

Val Arg Lys Lys Glu Glu Tyr Lys Met Ala Leu Tyr Asn Leu Tyr
    1985            1990            1995

Pro Gly Val Phe Glu Thr Val Glu Met Leu Pro Ser Lys Ala Gly
    2000            2005            2010

Ile Trp Arg Val Glu Cys Leu Ile Gly Glu His Leu His Ala Gly
    2015            2020            2025

Met Ser Thr Leu Phe Leu Val Tyr Ser Asn Lys Cys Gln Thr Pro
```

```
                       2030                 2035                 2040
Leu Gly Met Ala Ser Gly His Ile Arg Asp Phe Gln Ile Thr Ala
    2045                 2050                 2055
Ser Gly Gln Tyr Gly Gln Trp Ala Pro Lys Leu Ala Arg Leu His
    2060                 2065                 2070
Tyr Ser Gly Ser Ile Asn Ala Trp Ser Thr Lys Glu Pro Phe Ser
    2075                 2080                 2085
Trp Ile Lys Val Asp Leu Leu Ala Pro Met Ile Ile His Gly Ile
    2090                 2095                 2100
Lys Thr Gln Gly Ala Arg Gln Lys Phe Ser Ser Leu Tyr Ile Ser
    2105                 2110                 2115
Gln Phe Ile Ile Met Tyr Ser Leu Asp Gly Lys Lys Trp Gln Thr
    2120                 2125                 2130
Tyr Arg Gly Asn Ser Thr Gly Thr Leu Met Val Phe Phe Gly Asn
    2135                 2140                 2145
Val Asp Ser Ser Gly Ile Lys His Asn Ile Phe Asn Pro Pro Ile
    2150                 2155                 2160
Ile Ala Arg Tyr Ile Arg Leu His Pro Thr His Tyr Ser Ile Arg
    2165                 2170                 2175
Ser Thr Leu Arg Met Glu Leu Met Gly Cys Asp Leu Asn Ser Cys
    2180                 2185                 2190
Ser Met Pro Leu Gly Met Glu Ser Lys Ala Ile Ser Asp Ala Gln
    2195                 2200                 2205
Ile Thr Ala Ser Ser Tyr Phe Thr Asn Met Phe Ala Thr Trp Ser
    2210                 2215                 2220
Pro Ser Lys Ala Arg Leu His Leu Gln Gly Arg Ser Asn Ala Trp
    2225                 2230                 2235
Arg Pro Gln Val Asn Asn Pro Lys Glu Trp Leu Gln Val Asp Phe
    2240                 2245                 2250
Gln Lys Thr Met Lys Val Thr Gly Val Thr Thr Gln Gly Val Lys
    2255                 2260                 2265
Ser Leu Leu Thr Ser Met Tyr Val Lys Glu Phe Leu Ile Ser Ser
    2270                 2275                 2280
Ser Gln Asp Gly His Gln Trp Thr Leu Phe Phe Gln Asn Gly Lys
    2285                 2290                 2295
Val Lys Val Phe Gln Gly Asn Gln Asp Ser Phe Thr Pro Val Val
    2300                 2305                 2310
Asn Ser Leu Asp Pro Pro Leu Leu Thr Arg Tyr Leu Arg Ile His
    2315                 2320                 2325
Pro Gln Ser Trp Val His Gln Ile Ala Leu Arg Met Glu Val Leu
    2330                 2335                 2340
Gly Cys Glu Ala Gln Asp Leu Tyr
    2345                 2350

<210> SEQ ID NO 3
<211> LENGTH: 2332
<212> TYPE: PRT
<213> ORGANISM: Homo sapiens

<400> SEQUENCE: 3

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
```

```
                35                  40                  45
Thr Leu Phe Val Glu Phe Thr Asp His Leu Phe Asn Ile Ala Lys Pro
 50                  55                  60
Arg Pro Pro Trp Met Gly Leu Leu Gly Pro Thr Ile Gln Ala Glu Val
 65                  70                  75                  80
Tyr Asp Thr Val Val Ile Thr Leu Lys Asn Met Ala Ser His Pro Val
                     85                  90                  95
Ser Leu His Ala Val Gly Val Ser Tyr Trp Lys Ala Ser Glu Gly Ala
                100                 105                 110
Glu Tyr Asp Asp Gln Thr Ser Gln Arg Glu Lys Glu Asp Asp Lys Val
                115                 120                 125
Phe Pro Gly Gly Ser His Thr Tyr Val Trp Gln Val Leu Lys Glu Asn
130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Glu Lys Thr Gln Thr Leu
                180                 185                 190
His Lys Phe Ile Leu Leu Phe Ala Val Phe Asp Glu Gly Lys Ser Trp
                195                 200                 205
His Ser Glu Thr Lys Asn Ser Leu Met Gln Asp Arg Asp Ala Ala Ser
                210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
                260                 265                 270
Gly His Thr Phe Leu Val Arg Asn His Arg Gln Ala Ser Leu Glu Ile
                275                 280                 285
Ser Pro Ile Thr Phe Leu Thr Ala Gln Thr Leu Leu Met Asp Leu Gly
290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
                340                 345                 350
Ser Glu Met Asp Val Val Arg Phe Asp Asp Asp Asn Ser Pro Ser Phe
                355                 360                 365
Ile Gln Ile Arg Ser Val Ala Lys Lys His Pro Lys Thr Trp Val His
                370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
                420                 425                 430
Asp Glu Thr Phe Lys Thr Arg Glu Ala Ile Gln His Glu Ser Gly Ile
                435                 440                 445
Leu Gly Pro Leu Leu Tyr Gly Glu Val Gly Asp Thr Leu Leu Ile Ile
                450                 455                 460
```

-continued

```
Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895
```

```
Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
                915                 920                 925

Leu Thr Glu Ser Gly Gly Pro Leu Ser Leu Ser Glu Asn Asn Asp
        930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
                980                 985                 990

Val Ser Ile Ser Leu Leu Lys Thr Asn Lys Thr Ser Asn Asn Ser Ala
                995                 1000                1005

Thr Asn Arg Lys Thr His Ile Asp Gly Pro Ser Leu Leu Ile Glu
        1010                1015                1020

Asn Ser Pro Ser Val Trp Gln Asn Ile Leu Glu Ser Asp Thr Glu
        1025                1030                1035

Phe Lys Lys Val Thr Pro Leu Ile His Asp Arg Met Leu Met Asp
        1040                1045                1050

Lys Asn Ala Thr Ala Leu Arg Leu Asn His Met Ser Asn Lys Thr
        1055                1060                1065

Thr Ser Ser Lys Asn Met Glu Met Val Gln Gln Lys Lys Glu Gly
        1070                1075                1080

Pro Ile Pro Pro Asp Ala Gln Asn Pro Asp Met Ser Phe Phe Lys
        1085                1090                1095

Met Leu Phe Leu Pro Glu Ser Ala Arg Trp Ile Gln Arg Thr His
        1100                1105                1110

Gly Lys Asn Ser Leu Asn Ser Gly Gln Gly Pro Ser Pro Lys Gln
        1115                1120                1125

Leu Val Ser Leu Gly Pro Glu Lys Ser Val Glu Gly Gln Asn Phe
        1130                1135                1140

Leu Ser Glu Lys Asn Lys Val Val Val Gly Lys Gly Glu Phe Thr
        1145                1150                1155

Lys Asp Val Gly Leu Lys Glu Met Val Phe Pro Ser Ser Arg Asn
        1160                1165                1170

Leu Phe Leu Thr Asn Leu Asp Asn Leu His Glu Asn Asn Thr His
        1175                1180                1185

Asn Gln Glu Lys Lys Ile Gln Glu Glu Ile Glu Lys Lys Glu Thr
        1190                1195                1200

Leu Ile Gln Glu Asn Val Val Leu Pro Gln Ile His Thr Val Thr
        1205                1210                1215

Gly Thr Lys Asn Phe Met Lys Asn Leu Phe Leu Leu Ser Thr Arg
        1220                1225                1230

Gln Asn Val Glu Gly Ser Tyr Asp Gly Ala Tyr Ala Pro Val Leu
        1235                1240                1245

Gln Asp Phe Arg Ser Leu Asn Asp Ser Thr Asn Arg Thr Lys Lys
        1250                1255                1260

His Thr Ala His Phe Ser Lys Lys Gly Glu Glu Glu Asn Leu Glu
        1265                1270                1275

Gly Leu Gly Asn Gln Thr Lys Gln Ile Val Glu Lys Tyr Ala Cys
        1280                1285                1290

Thr Thr Arg Ile Ser Pro Asn Thr Ser Gln Gln Asn Phe Val Thr
```

```
                1295                1300               1305

Gln Arg Ser Lys Arg Ala Leu Lys Gln Phe Arg Leu Pro Leu Glu
    1310                1315               1320

Glu Thr Glu Leu Glu Lys Arg Ile Ile Val Asp Asp Thr Ser Thr
    1325                1330               1335

Gln Trp Ser Lys Asn Met Lys His Leu Thr Pro Ser Thr Leu Thr
    1340                1345               1350

Gln Ile Asp Tyr Asn Glu Lys Glu Lys Gly Ala Ile Thr Gln Ser
    1355                1360               1365

Pro Leu Ser Asp Cys Leu Thr Arg Ser His Ser Ile Pro Gln Ala
    1370                1375               1380

Asn Arg Ser Pro Leu Pro Ile Ala Lys Val Ser Ser Phe Pro Ser
    1385                1390               1395

Ile Arg Pro Ile Tyr Leu Thr Arg Val Leu Phe Gln Asp Asn Ser
    1400                1405               1410

Ser His Leu Pro Ala Ala Ser Tyr Arg Lys Lys Asp Ser Gly Val
    1415                1420               1425

Gln Glu Ser Ser His Phe Leu Gln Gly Ala Lys Lys Asn Asn Leu
    1430                1435               1440

Ser Leu Ala Ile Leu Thr Leu Glu Met Thr Gly Asp Gln Arg Glu
    1445                1450               1455

Val Gly Ser Leu Gly Thr Ser Ala Thr Asn Ser Val Thr Tyr Lys
    1460                1465               1470

Lys Val Glu Asn Thr Val Leu Pro Lys Pro Asp Leu Pro Lys Thr
    1475                1480               1485

Ser Gly Lys Val Glu Leu Leu Pro Lys Val His Ile Tyr Gln Lys
    1490                1495               1500

Asp Leu Phe Pro Thr Glu Thr Ser Asn Gly Ser Pro Gly His Leu
    1505                1510               1515

Asp Leu Val Glu Gly Ser Leu Leu Gln Gly Thr Glu Gly Ala Ile
    1520                1525               1530

Lys Trp Asn Glu Ala Asn Arg Pro Gly Lys Val Pro Phe Leu Arg
    1535                1540               1545

Val Ala Thr Glu Ser Ser Ala Lys Thr Pro Ser Lys Leu Leu Asp
    1550                1555               1560

Pro Leu Ala Trp Asp Asn His Tyr Gly Thr Gln Ile Pro Lys Glu
    1565                1570               1575

Glu Trp Lys Ser Gln Glu Lys Ser Pro Glu Lys Thr Ala Phe Lys
    1580                1585               1590

Lys Lys Asp Thr Ile Leu Ser Leu Asn Ala Cys Glu Ser Asn His
    1595                1600               1605

Ala Ile Ala Ala Ile Asn Glu Gly Gln Asn Lys Pro Glu Ile Glu
    1610                1615               1620

Val Thr Trp Ala Lys Gln Gly Arg Thr Glu Arg Leu Cys Ser Gln
    1625                1630               1635

Asn Pro Pro Val Leu Lys Arg His Gln Arg Glu Ile Thr Arg Thr
    1640                1645               1650

Thr Leu Gln Ser Asp Gln Glu Glu Ile Asp Tyr Asp Asp Thr Ile
    1655                1660               1665

Ser Val Glu Met Lys Lys Glu Asp Phe Asp Ile Tyr Asp Glu Asp
    1670                1675               1680

Glu Asn Gln Ser Pro Arg Ser Phe Gln Lys Lys Thr Arg His Tyr
    1685                1690               1695
```

```
Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860

Asn Pro Ala His Gly Arg Gln Val Thr Val Gln Glu Phe Ala Leu
1865                1870                1875

Phe Phe Thr Ile Phe Asp Glu Thr Lys Ser Trp Tyr Phe Thr Glu
1880                1885                1890

Asn Met Glu Arg Asn Cys Arg Ala Pro Cys Asn Ile Gln Met Glu
1895                1900                1905

Asp Pro Thr Phe Lys Glu Asn Tyr Arg Phe His Ala Ile Asn Gly
1910                1915                1920

Tyr Ile Met Asp Thr Leu Pro Gly Leu Val Met Ala Gln Asp Gln
1925                1930                1935

Arg Ile Arg Trp Tyr Leu Leu Ser Met Gly Ser Asn Glu Asn Ile
1940                1945                1950

His Ser Ile His Phe Ser Gly His Val Phe Thr Val Arg Lys Lys
1955                1960                1965

Glu Glu Tyr Lys Met Ala Leu Tyr Asn Leu Tyr Pro Gly Val Phe
1970                1975                1980

Glu Thr Val Glu Met Leu Pro Ser Lys Ala Gly Ile Trp Arg Val
1985                1990                1995

Glu Cys Leu Ile Gly Glu His Leu His Ala Gly Met Ser Thr Leu
2000                2005                2010

Phe Leu Val Tyr Ser Asn Lys Cys Gln Thr Pro Leu Gly Met Ala
2015                2020                2025

Ser Gly His Ile Arg Asp Phe Gln Ile Thr Ala Ser Gly Gln Tyr
2030                2035                2040

Gly Gln Trp Ala Pro Lys Leu Ala Arg Leu His Tyr Ser Gly Ser
2045                2050                2055

Ile Asn Ala Trp Ser Thr Lys Glu Pro Phe Ser Trp Ile Lys Val
2060                2065                2070

Asp Leu Leu Ala Pro Met Ile Ile His Gly Ile Lys Thr Gln Gly
2075                2080                2085

Ala Arg Gln Lys Phe Ser Ser Leu Tyr Ile Ser Gln Phe Ile Ile
2090                2095                2100
```

```
Met Tyr Ser Leu Asp Gly Lys Lys Trp Gln Thr Tyr Arg Gly Asn
    2105            2110                2115
Ser Thr Gly Thr Leu Met Val Phe Phe Gly Asn Val Asp Ser Ser
    2120            2125                2130
Gly Ile Lys His Asn Ile Phe Asn Pro Pro Ile Ile Ala Arg Tyr
    2135            2140                2145
Ile Arg Leu His Pro Thr His Tyr Ser Ile Arg Ser Thr Leu Arg
    2150            2155                2160
Met Glu Leu Met Gly Cys Asp Leu Asn Ser Cys Ser Met Pro Leu
    2165            2170                2175
Gly Met Glu Ser Lys Ala Ile Ser Asp Ala Gln Ile Thr Ala Ser
    2180            2185                2190
Ser Tyr Phe Thr Asn Met Phe Ala Thr Trp Ser Pro Ser Lys Ala
    2195            2200                2205
Arg Leu His Leu Gln Gly Arg Ser Asn Ala Trp Arg Pro Gln Val
    2210            2215                2220
Asn Asn Pro Lys Glu Trp Leu Gln Val Asp Phe Gln Lys Thr Met
    2225            2230                2235
Lys Val Thr Gly Val Thr Thr Gln Gly Val Lys Ser Leu Leu Thr
    2240            2245                2250
Ser Met Tyr Val Lys Glu Phe Leu Ile Ser Ser Ser Gln Asp Gly
    2255            2260                2265
His Gln Trp Thr Leu Phe Phe Gln Asn Gly Lys Val Lys Val Phe
    2270            2275                2280
Gln Gly Asn Gln Asp Ser Phe Thr Pro Val Val Asn Ser Leu Asp
    2285            2290                2295
Pro Pro Leu Leu Thr Arg Tyr Leu Arg Ile His Pro Gln Ser Trp
    2300            2305                2310
Val His Gln Ile Ala Leu Arg Met Glu Val Leu Gly Cys Glu Ala
    2315            2320                2325
Gln Asp Leu Tyr
    2330

<210> SEQ ID NO 4
<211> LENGTH: 5012
<212> TYPE: DNA
<213> ORGANISM: artificial sequence
<220> FEATURE:
<223> OTHER INFORMATION: FVIII without domain B

<400> SEQUENCE: 4
ccgccagtgt gatggatatc tgcagaattc ggcttacacc catggaaata gagctctcca      60
cctgcttctt tctgtgcctt ttgcgattct gctttagtgc caccagaaga tactacctgg     120
gtgcagtgga actgtcatgg gactatatgc aaagtgatct cggtgagctg cctgtggacg     180
caaggtttgt ttatgcatcc ttttttaaaa tacattgagt atgcttgcct tttagatata     240
gaaatatctg atgctgtctt cttcactaaa ttttgattac atgatttgac agcaatattg     300
aagagtctaa cagccagcac gcaggttggt aagtactgtg ggaacatcac agattttggc     360
tccatgccct aaagagaaat tggctttcag attatttgga ttaaaaacaa agactttctt     420
aagagatgta aaattttcat gatgttttct ttttgctaa aactaaagaa ttaacgcgta     480
ttcttttaca tttcagattt cctcctagag tgccaaaatc ttttccattc aacacctcag     540
tcgtgtacaa aaagactctg tttgtagaat tcacggatca ccttttcaac atcgctaagc     600
caaggccacc ctggatgggt ctgctaggtc ctaccatcca ggctgaggtt tatgatacag     660
```

```
tggtcattac acttaagaac atggcttccc atcctgtcag tcttcatgct gttggtgtat    720
cctactggaa agcttctgag ggagctgaat atgatgatca gaccagtcaa agggagaaag    780
aagatgataa agtcttccct ggtggaagcc atacatatgt ctggcaggtc ctgaaagaga    840
atggtccaat ggcctctgac ccactgtgcc ttacctactc atatctttct catgtggacc    900
tggtaaaaga cttgaattca ggcctcattg gagccctact agtatgtaga aagggagtc    960 tggccaagga aaagacacag accttgcaca aatttatact acttttttgct gtatttgatg   1020 aagggaaaag ttggcactca gaaacaaaga actccttgat gcaggatagg gatgctgcat   1080
ctgctcgggc ctggcctaaa atgcacacag tcaatggtta tgtaaacagg tctctgccag   1140
gtctgattgg atgccacagg aaatcagtct attggcatgt gattggaatg ggcaccactc   1200
ctgaagtgca ctcaatattc ctcgaaggtc acacatttct tgtgaggaac catcgccagg   1260
cgtccttgga aatctcgcca ataactttcc ttactgctca aacactcttg atggaccttg   1320
gacagtttct actgttttgt catatctctt cccaccaaca tgatggcatg gaagcttatg   1380
tcaaagtaga cagctgtcca gaggaacccc aactacgaat gaaaaataat gaagaagcgg   1440
aagactatga tgatgatctt actgattctg aaatggatgg ggtcaggttt gatgatgaca   1500
actctccttc ctttatccaa attcgctcag ttgccaagaa gcatcctaaa acttgggtac   1560
attacattgc tgctgaagag gaggactggg actatgctcc cttagtcctc gcccccgatg   1620
acagaagtta taaaagtcaa tatttgaaca atggccctca gcggattggt aggaagtaca   1680
aaaaagtccg atttatggca tacacagatg aaacctttaa gactcgtgaa gctattcagc   1740
atgaatcagg aatcttggga cctttacttt atggggaagt tggagacaca ctgttgatta   1800
tatttaagaa tcaagcaagc agaccatata acatctaccc tcacggaatc actgatgtcc   1860
gtcctttgta ttcaaggaga ttaccaaaag gtgtaaaaca tttgaaggat tttccaattc   1920
tgccaggaga aatattcaaa tataaatgga cagtgactgt agaagatggg ccaactaaat   1980
cagatcctcg gtgcctgacc cgctattact ctagtttcgt taatatggag agagatctag   2040
cttcaggact cattggccct ctcctcatct gctacaaaga atctgtagat caaagaggaa   2100
accagataat gtcagacaag aggaatgtca tcctgttttc tgtatttgat gagaaccgaa   2160
gctggtacct cacagagaat atacaacgct ttctccccaa tccagctgga gtgcagcttg   2220
aggatccaga gttccaagcc tccaacatca tgcacagcat caatggctat gttttttgata   2280 gtttgcagtt gtcagtttgt ttgcatgagg tggcatactg gtacattcta agcattggag   2340
cacagactga cttcctttct gtcttcttct ctggatatac cttcaaacac aaaatggtct   2400
atgaagacac actcacccta ttcccattct caggagaaac tgtcttcatg tcgatggaaa   2460
acccaggttt gtttatgcat cctttttttaa aatacattga gtatgcttgc cttttagata   2520
tagaaatatc tgatgctgtc ttcttcacta aattttgatt acatgatttg acagcaatat   2580
tgaagagtct aacagccagc acgcaggttg gtaagtactg tgggaacatc acagattttg   2640
gctccatgcc ctaaagagaa attggctttc agattatttg gattaaaaac aaagactttc   2700
ttaagagatg taaaattttc atgatgtttt ctttttttgct aaaactaaag aattaacgcg   2760
tattctttta catttcaggt ctatggattc tggggtgcca caactcagac tttcggaaca   2820
gaggcatgac cgccttactg aaggtttcta gttgtgacaa gaacactggt gattattacg   2880
aggacagtta tgaagatatt tcagcatact tgctgagtaa aaacaatgcc attgaaccaa   2940
gaagacgtcg acgagaaata actcgtacta ctcttcagtc agatcaagag gaaattgact   3000
atgatgatac catatcagtt gaaatgaaga aggaagattt tgacatttat gatgaggatg   3060
```

```
aaaatcagag ccccccgcagc tttcaaaaga aaacacgaca ctattttatt gctgcagtgg    3120
agaggctctg ggattatggg atgagtagct ccccacatgt tctaagaaac agggctcaga    3180
gtggcagtgt ccctcagttc aagaaagttg ttttccagga atttactgat ggctccttta    3240
ctcagcccct taccgtgga gaactaaatg aacatttggg actcctgggg ccatatataa    3300
gagcagaagt tgaagataat atcatggtaa cttttcagaaa tcaggcctct cgtccctatt    3360
ccttctattc tagccttatt tcttatgagg aagatcagag gcaaggagca gaacctagaa    3420
aaaactttgt caagcctaat gaaaccaaaa cttacttttg gaaagtgcaa catcatatgg    3480
cacccactaa agatgagttt gactgcaaag cctgggctta tttctctgat gttgacctgg    3540
aaaaagatgt gcactcaggc ctgattggac cccttctggt ctgccacact aacacactga    3600
accctgctca tgggagacaa gtgacagtac aggaatttgc tctgttttc accatctttg    3660 atgagaccaa aagctggtac ttcactgaaa atatggaaag aaactgcagg gctccctgca    3720
atatccagat ggaagatccc acttttaaag agaattatcg cttccatgca atcaatggct    3780
acataatgga tacactacct ggcttagtaa tggctcagga tcaaaggatt cgatggtatc    3840
tgctcagcat gggcagcaat gaaaacatcc attctattca tttcagtgga catgtgttca    3900
ctgtacgaaa aaaagaggag tataaaatgg cactgtacaa tctctatcca ggtgttttg    3960 agacagtgga aatgttacca tccaaagctg aatttggcg ggtggaatgc cttattggcg    4020
agcatctaca tgctgggatg agcacacttt ttctggtgta cagcaataag tgtcagactc    4080
ccctgggaat ggcttctgga cacattagag atttccagat tacagcttca ggacaatatg    4140
gacagtgggc cccaaagctg gccagacttc attattccgg atcaatcaat gcctggagca    4200
ccaaggagcc ttttcttgg atcaaggtgg atctgttggc accaatgatt attcacggca    4260
tcaagaccca gggtgcccgt cagaagttct ccagcctcta catctctcag tttatcatca    4320
tgtatagtct tgatgggaag aagtggcaga cttatcgagg aaattccact ggaaccttaa    4380
tggtcttctt tggcaatgtg gattcatctg ggataaaaca caatatttttt aaccctccaa    4440 ttattgctcg atacatccgt ttgcacccaa ctcattatag cattcgcagc actcttcgca    4500
tggagttgat gggctgtgat ttaaatagtt gcagcatgcc attgggaatg gagagtaaag    4560
caatatcaga tgcacagatt actgcttcat cctactttac caatatgttt gccacctggt    4620
ctccttcaaa agctcgactt cacctccaag ggaggagtaa tgcctggaga cctcaggtga    4680
ataatccaaa agagtggctg caagtggact tccagaagac aatgaaagtc acaggagtaa    4740
ctactcaggg agtaaaatct ctgcttacca gcatgtatgt gaaggagttc ctcatctcca    4800
gcagtcaaga tggccatcag tggactctct ttttttcagaa tggcaaagta aaggtttttc    4860
agggaaatca agactccttc acacctgtgg tgaactctct agacccaccg ttactgactc    4920
gctaccttcg aattcacccc cagagttggg tgcaccagat tgccctgagg atggaggttc    4980
tgggctgcga ggcacaggac ctctactgac tc                                   5012
```

<210> SEQ ID NO 5
<211> LENGTH: 1412
<212> TYPE: PRT
<213> ORGANISM: artificial sequence
<220> FEATURE:
<223> OTHER INFORMATION: FVIII without domain B

<400> SEQUENCE: 5

Met Gln Ser Asp Leu Gly Glu Leu Pro Val Asp Ala Arg Phe Pro Pro
1               5                   10                  15

-continued

```
Arg Val Pro Lys Ser Phe Pro Phe Asn Thr Ser Val Val Tyr Lys Lys
         20                  25                  30

Thr Leu Phe Val Glu Phe Thr Asp His Leu Phe Asn Ile Ala Lys Pro
             35                  40                  45

Arg Pro Pro Trp Met Gly Leu Leu Gly Pro Thr Ile Gln Ala Glu Val
 50                  55                  60

Tyr Asp Thr Val Val Ile Thr Leu Lys Asn Met Ala Ser His Pro Val
 65                  70                  75                  80

Ser Leu His Ala Val Gly Val Ser Tyr Trp Lys Ala Ser Glu Gly Ala
                 85                  90                  95

Glu Tyr Asp Asp Gln Thr Ser Gln Arg Glu Lys Glu Asp Lys Val
                100                 105                 110

Phe Pro Gly Gly Ser His Thr Tyr Val Trp Gln Val Leu Lys Glu Asn
             115                 120                 125

Gly Pro Met Ala Ser Asp Pro Leu Cys Leu Thr Tyr Ser Tyr Leu Ser
         130                 135                 140

His Val Asp Leu Val Lys Asp Leu Asn Ser Gly Leu Ile Gly Ala Leu
145                 150                 155                 160

Leu Val Cys Arg Glu Gly Ser Leu Ala Lys Glu Lys Thr Gln Thr Leu
                 165                 170                 175

His Lys Phe Ile Leu Leu Phe Ala Val Phe Asp Glu Gly Lys Ser Trp
             180                 185                 190

His Ser Glu Thr Lys Asn Ser Leu Met Gln Asp Arg Asp Ala Ala Ser
         195                 200                 205

Ala Arg Ala Trp Pro Lys Met His Thr Val Asn Gly Tyr Val Asn Arg
     210                 215                 220

Ser Leu Pro Gly Leu Ile Gly Cys His Arg Lys Ser Val Tyr Trp His
225                 230                 235                 240

Val Ile Gly Met Gly Thr Thr Pro Glu Val His Ser Ile Phe Leu Glu
                 245                 250                 255

Gly His Thr Phe Leu Val Arg Asn His Arg Gln Ala Ser Leu Glu Ile
             260                 265                 270

Ser Pro Ile Thr Phe Leu Thr Ala Gln Thr Leu Leu Met Asp Leu Gly
         275                 280                 285

Gln Phe Leu Leu Phe Cys His Ile Ser Ser His Gln His Asp Gly Met
     290                 295                 300

Glu Ala Tyr Val Lys Val Asp Ser Cys Pro Glu Glu Pro Gln Leu Arg
305                 310                 315                 320

Met Lys Asn Asn Glu Glu Ala Glu Asp Tyr Asp Asp Leu Thr Asp
                 325                 330                 335

Ser Glu Met Asp Val Val Arg Phe Asp Asp Asp Asn Ser Pro Ser Phe
             340                 345                 350

Ile Gln Ile Arg Ser Val Ala Lys Lys His Pro Lys Thr Trp Val His
         355                 360                 365

Tyr Ile Ala Ala Glu Glu Asp Trp Asp Tyr Ala Pro Leu Val Leu
     370                 375                 380

Ala Pro Asp Asp Arg Ser Tyr Lys Ser Gln Tyr Leu Asn Asn Gly Pro
385                 390                 395                 400

Gln Arg Ile Gly Arg Lys Tyr Lys Lys Val Arg Phe Met Ala Tyr Thr
                 405                 410                 415

Asp Glu Thr Phe Lys Thr Arg Glu Ala Ile Gln His Glu Ser Gly Ile
             420                 425                 430

Leu Gly Pro Leu Leu Tyr Gly Glu Val Gly Asp Thr Leu Leu Ile Ile
         435                 440                 445
```

```
Phe Lys Asn Gln Ala Ser Arg Pro Tyr Asn Ile Tyr Pro His Gly Ile
    450                 455                 460

Thr Asp Val Arg Pro Leu Tyr Ser Arg Arg Leu Pro Lys Gly Val Lys
465                 470                 475                 480

His Leu Lys Asp Phe Pro Ile Leu Pro Gly Glu Ile Phe Lys Tyr Lys
                485                 490                 495

Trp Thr Val Thr Val Glu Asp Gly Pro Thr Lys Ser Asp Pro Arg Cys
                500                 505                 510

Leu Thr Arg Tyr Tyr Ser Ser Phe Val Asn Met Glu Arg Asp Leu Ala
                515                 520                 525

Ser Gly Leu Ile Gly Pro Leu Leu Ile Cys Tyr Lys Glu Ser Val Asp
                535                 540

Gln Arg Gly Asn Gln Ile Met Ser Asp Lys Arg Asn Val Ile Leu Phe
545                 550                 555                 560

Ser Val Phe Asp Glu Asn Arg Ser Trp Tyr Leu Thr Glu Asn Ile Gln
                565                 570                 575

Arg Phe Leu Pro Asn Pro Ala Gly Val Gln Leu Glu Asp Pro Glu Phe
                580                 585                 590

Gln Ala Ser Asn Ile Met His Ser Ile Asn Gly Tyr Val Phe Asp Ser
                595                 600                 605

Leu Gln Leu Ser Val Cys Leu His Glu Val Ala Tyr Trp Tyr Ile Leu
    610                 615                 620

Ser Ile Gly Ala Gln Thr Asp Phe Leu Ser Val Phe Phe Ser Gly Tyr
625                 630                 635                 640

Thr Phe Lys His Lys Met Val Tyr Glu Asp Thr Leu Thr Leu Phe Pro
                645                 650                 655

Phe Ser Gly Glu Thr Val Phe Met Ser Met Glu Asn Pro Gly Leu Trp
                660                 665                 670

Ile Leu Gly Cys His Asn Ser Asp Phe Arg Asn Arg Gly Met Thr Ala
                675                 680                 685

Leu Leu Lys Val Ser Ser Cys Asp Lys Asn Thr Gly Asp Tyr Tyr Glu
    690                 695                 700

Asp Ser Tyr Glu Asp Ile Ser Ala Tyr Leu Leu Ser Lys Asn Asn Ala
705                 710                 715                 720

Ile Glu Pro Arg Arg Arg Arg Glu Ile Thr Arg Thr Thr Leu Gln
                725                 730                 735

Ser Asp Gln Glu Glu Ile Asp Tyr Asp Asp Thr Ile Ser Val Glu Met
                740                 745                 750

Lys Lys Glu Asp Phe Asp Ile Tyr Asp Glu Asp Glu Asn Gln Ser Pro
    755                 760                 765

Arg Ser Phe Gln Lys Lys Thr Arg His Tyr Phe Ile Ala Ala Val Glu
    770                 775                 780

Arg Leu Trp Asp Tyr Gly Met Ser Ser Ser Pro His Val Leu Arg Asn
785                 790                 795                 800

Arg Ala Gln Ser Gly Ser Val Pro Gln Phe Lys Lys Val Val Phe Gln
                805                 810                 815

Glu Phe Thr Asp Gly Ser Phe Thr Gln Pro Leu Tyr Arg Gly Glu Leu
                820                 825                 830

Asn Glu His Leu Gly Leu Leu Gly Pro Tyr Ile Arg Ala Glu Val Glu
                835                 840                 845

Asp Asn Ile Met Val Thr Phe Arg Asn Gln Ala Ser Arg Pro Tyr Ser
850                 855                 860

Phe Tyr Ser Ser Leu Ile Ser Tyr Glu Glu Asp Gln Arg Gln Gly Ala
```

-continued

```
            865                 870                 875                 880
Glu Pro Arg Lys Asn Phe Val Lys Pro Asn Glu Thr Lys Thr Tyr Phe
                    885                 890                 895
Trp Lys Val Gln His His Met Ala Pro Thr Lys Asp Glu Phe Asp Cys
                900                 905                 910
Lys Ala Trp Ala Tyr Phe Ser Asp Val Asp Leu Glu Lys Asp Val His
                915                 920                 925
Ser Gly Leu Ile Gly Pro Leu Leu Val Cys His Thr Asn Thr Leu Asn
        930                 935                 940
Pro Ala His Gly Arg Gln Val Thr Val Gln Glu Phe Ala Leu Phe Phe
945                 950                 955                 960
Thr Ile Phe Asp Glu Thr Lys Ser Trp Tyr Phe Thr Glu Asn Met Glu
                965                 970                 975
Arg Asn Cys Arg Ala Pro Cys Asn Ile Gln Met Glu Asp Pro Thr Phe
                980                 985                 990
Lys Glu Asn Tyr Arg Phe His Ala Ile Asn Gly Tyr Ile Met Asp Thr
                995                 1000                1005
Leu Pro Gly Leu Val Met Ala Gln Asp Gln Arg Ile Arg Trp Tyr
        1010                1015                1020
Leu Leu Ser Met Gly Ser Asn Glu Asn Ile His Ser Ile His Phe
        1025                1030                1035
Ser Gly His Val Phe Thr Val Arg Lys Lys Glu Glu Tyr Lys Met
        1040                1045                1050
Ala Leu Tyr Asn Leu Tyr Pro Gly Val Phe Glu Thr Val Glu Met
        1055                1060                1065
Leu Pro Ser Lys Ala Gly Ile Trp Arg Val Glu Cys Leu Ile Gly
        1070                1075                1080
Glu His Leu His Ala Gly Met Ser Thr Leu Phe Leu Val Tyr Ser
        1085                1090                1095
Asn Lys Cys Gln Thr Pro Leu Gly Met Ala Ser Gly His Ile Arg
        1100                1105                1110
Asp Phe Gln Ile Thr Ala Ser Gly Gln Tyr Gly Gln Trp Ala Pro
        1115                1120                1125
Lys Leu Ala Arg Leu His Tyr Ser Gly Ser Ile Asn Ala Trp Ser
        1130                1135                1140
Thr Lys Glu Pro Phe Ser Trp Ile Lys Val Asp Leu Leu Ala Pro
        1145                1150                1155
Met Ile Ile His Gly Ile Lys Thr Gln Gly Ala Arg Gln Lys Phe
        1160                1165                1170
Ser Ser Leu Tyr Ile Ser Gln Phe Ile Ile Met Tyr Ser Leu Asp
        1175                1180                1185
Gly Lys Lys Trp Gln Thr Tyr Arg Gly Asn Ser Thr Gly Thr Leu
        1190                1195                1200
Met Val Phe Phe Gly Asn Val Asp Ser Ser Gly Ile Lys His Asn
        1205                1210                1215
Ile Phe Asn Pro Pro Ile Ile Ala Arg Tyr Ile Arg Leu His Pro
        1220                1225                1230
Thr His Tyr Ser Ile Arg Ser Thr Leu Arg Met Glu Leu Met Gly
        1235                1240                1245
Cys Asp Leu Asn Ser Cys Ser Met Pro Leu Gly Met Glu Ser Lys
        1250                1255                1260
Ala Ile Ser Asp Ala Gln Ile Thr Ala Ser Ser Tyr Phe Thr Asn
        1265                1270                1275
```

```
Met Phe Ala Thr Trp Ser Pro Ser Lys Ala Arg Leu His Leu Gln
    1280            1285            1290

Gly Arg Ser Asn Ala Trp Arg Pro Gln Val Asn Asn Pro Lys Glu
    1295            1300            1305

Trp Leu Gln Val Asp Phe Gln Lys Thr Met Lys Val Thr Gly Val
    1310            1315            1320

Thr Thr Gln Gly Val Lys Ser Leu Leu Thr Ser Met Tyr Val Lys
    1325            1330            1335

Glu Phe Leu Ile Ser Ser Ser Gln Asp Gly His Gln Trp Thr Leu
    1340            1345            1350

Phe Phe Gln Asn Gly Lys Val Lys Val Phe Gln Gly Asn Gln Asp
    1355            1360            1365

Ser Phe Thr Pro Val Val Asn Ser Leu Asp Pro Pro Leu Leu Thr
    1370            1375            1380

Arg Tyr Leu Arg Ile His Pro Gln Ser Trp Val His Gln Ile Ala
    1385            1390            1395

Leu Arg Met Glu Val Leu Gly Cys Glu Ala Gln Asp Leu Tyr
    1400            1405            1410
```

VIII FACTORS FOR THE TREATMENT OF TYPE A HEMOPHILIA

CROSS-REFERENCE TO RELATED APPLICATION

This application is the U.S. national stage application of International Patent Application No. PCT/FR2008/050301, filed Feb. 22, 2008, the disclosure of which is hereby incorporated by reference in its entirety, including all figures, tables and amino acid or nucleic acid sequences.

FIELD OF THE INVENTION

The present invention relates to the field of hemostasis, more specifically to that of hemophilia A. The invention relates to human factor VIII variants and to the uses thereof.

TECHNICAL BACKGROUND

Factor VIII (FVIII) is mainly synthesized by hepatocytes and sinusoidal endothelial cells. The plasma concentration of FVIII is comprised between 0.1 and 0.2 mg/l; the circulating form is inactive and associates with von Willebrand factor (vWF). FVIII plays a key role in the endogenous (so-called intrinsic) pathway of blood coagulation. When a blood vessel is damaged by trauma, bleeding is triggered. In response, the process of hemostasis is initiated, consisting of a complex chain of events leading to the formation of a blood clot which seals the site of injury. Blood coagulation begins when platelets adhere to injured vessel walls. If the injury is severe, the platelet aggregates at the site of injury are insufficient to form a hemostatic plug to staunch the blood flow. Thus coagulation factors intervene whose purpose is to form the fibrin network, generated from soluble fibrinogen molecules by the action of thrombin. The formation of this network composed of insoluble fibers is crucial to firmly anchor the blood clot. Cascade shall be understood to mean that, sequentially and at each step, a precursor protein is converted to an activated protease which cleaves or acts as cofactor for cleavage of the next precursor protein of the cascade. Thus, FVIII is proteolytically cleaved in FVIIIa by the action of thrombin and factor Xa. In this active procoagulant form (FVIIIa), FVIII strikingly increases the proteolytic efficiency of factor FIXa towards factor FX.

Hemophilia A is a bleeding disorder characterized by a deficiency of activated FVIII due to a mutation in the recessive gene encoding FVIII. In some rare cases, hemophilia A may arise from the spontaneous development of auto-antibodies directed against FVIII; this is known as acquired hemophilia A.

Hemophilia is manifested as a defect of blood clotting in response to a hemorrhage. Untreated type A hemophiliacs exhibit symptoms such as excessive bleeding after trauma and sometimes even spontaneous hemorrhages, particularly into the articulation joints. Hemophilia A is the most common coagulation disorders and occurs in 1 in 5,000-10,000 male births. Not all hemophiliacs are affected in the same manner or to the same extent. For instance, hemophilia A is considered i) severe when FVIII levels are less than or equal to 1% of "normal" circulating levels; ii) moderate when FVIII levels are within the range of 1 to 5% of "normal"; and iii) mild when FVIII levels are between 5 and 30% of normal. These three types of hemophilia A occur at the following frequencies: 50% of hemophiliac patients have the severe form, 10% the moderate form and 40% the mild form.

Many genetic abnormalities have been associated with the gene coding for FVIII. Said gene is located at the tip of the long arm of the X chromosome (locus Xq28). Hemophilia A results from an abnormality in this gene. It is an X-linked recessive disorder: males and females can transmit the disorder but only males are affected. The molecular defects may be gene mutations, deletions or inversions. The majority of patients harboring missense point mutations have mild or moderate disease. Deletions are classified into two types: i) small deletions; ii) large deletions (>1 kb). Most large deletions confer a severe phenotype. With respect to genetic inversions, the intron 22 inversion is the most frequent and is responsible for the majority of cases of severe hemophilia A (45%). Another inversion, the intron 1 one, can cause severe disease while less frequent (3%).

In summary, these mutations result in either a decreased production of functionally normal FVIII molecules, or a quantitatively normal production of functionally defective FVIII molecules.

The FVIII gene codes for a polypeptide chain of 2,351 amino acids (aa) (SEQ ID No. 2) corresponding to a 19 aa signal peptide and a 2332 aa mature protein (330 kDa) (SEQ ID No. 3). The nucleotide sequence of the FVIII precursor is given in SEQ ID No. 1 and the corresponding protein sequence in SEQ ID No. 2. The FVIII precursor consists of a succession of the following seven functional domains: A1, a1, A2, a2, B, a3, A3, C1 and C2, from the N-terminal to the C-terminal (Vehar et al., 1984, Nature, 312:337-342).

FVIII undergoes a first intracellular proteolysis at arginines 1313 and 1648, producing a FVIII heterodimer consisting of: i) an A1-a1-A2-a2-B heavy chain; ii) an a3-A3-C1-C2 light chain. It circulates in plasma as a heterodimer. The interaction between the two chains is ensured among others by the presence of a chelated copper molecule in domains A1 and A3. Immediately after being secreted in plasma, FVIII forms a very high affinity association with von Willebrand factor (vWF) which protects it from proteases. FVIII and vWF form a noncovalent complex in which binding takes place mainly via two regions of FVIII: the N-terminal region and the C-terminal region at 2303-2332 (C2 domain) of the light chain. During coagulation, FVIII is cleaved by thrombin and factor Xa at three sites: i) thrombin cleaves at Arginine 1689 of the light chain and at Arginine 372 and Arginine 740 of the heavy chain; ii) factor XA cleaves FVIII at Arginine 336, Arginine 372 and Arginine 740. Two of these cleavages are common (Arginine 372 and Arginine 740). Cleavages at Arginine 372 and Arginine 1689 are essential for FVIII to participate in the coagulation cascade. These cleavages activate FVIII, also known as FVIIIa ("a" for "active"); in addition to FVIIIa activation, these cleavages result in removal of the 170 kDa B domain and dissociation of FVIIIa from vWF.

The B domain of FVIII, defined by amino acids 741 to 1648, can be totally or partially deleted with no loss of activity of recombinant FVIII (Toole et al., 1986, Proc. Natl. Acad. Sci. USA, 83 (16):5939-5942; Eaton et al., 1986, Biochemistry, 25 (26):8343-8347; Langer et al., 1988, Behring Inst. Mitt, 82:16-25; Meulien et al., 1988, Protein Eng, 2(4):301-6; and U.S. Pat. No. 4,868,112), including for porcine FVIII (U.S. Pat. No. 6,458,563; WO01/68109; U.S. Pat. No. 6,770, 744), which in some cases can be used to replace the human FVIII.

Mutations, most of them point mutations, can be inserted at different sites of FVIII without causing a loss of FVIII procoagulant activity (U.S. Pat. Nos. 5,744,446; 5,859,204; 6,060,447; 6,180,371; 6,228,620; 6,376,463; EP 1561757;

WO02/24723; WO97/49725). EP1502921 and WO2005/111074 describe human FVIIII variants with improved stability.

Other patents (US 2003/0083257; WO2005/040213; and U.S. Pat. No. 6,780,614) may be cited which describe modifications of FVIII cDNA for increasing its production in animal cells. The modifications of the cDNA are disclosed in patents US20021165177; US2002/0182684; EP1048726; EP1283263.

The number of units of FVIII administered is expressed in International Units (IU) with reference to the WHO standard for FVIII. FVIII activity is expressed either as a percentage (relative to normal human plasma) or in International Units (relative to an international standard). One International Unit (IU) of FVIII activity is equivalent to that quantity of FVIII contained in one milliliter of normal human plasma. Plasmatic FVIII assays may be carried out either by a chronometric method or by a chromogenic method.

Hemophilia A (severe and moderate forms) is generally treated by preventive or curative replacement therapy, which is based on repeated injections of the deficient coagulation factor or perfusion thereof. Patients with hemophilia A are treated with different types of plasma-derived or recombinant FVIII: i) recombinant; ii) semipurified plasma products; iii) plasma products purified on conventional or immunoaffinity columns. The first recombinant FVIII concentrates contained albumin as stabilizing agent. These included Kogenate® (Bayer), Helixate® (manufactured by Bayer, distributed by Aventis), and Recombinate® (Baxter). New albumin-free formulations have been developed, such as Kogenate® FS (Bayer), Helixate® FS (Bayer), and ReFacto$^{MC}$ (Wyeth). These nonetheless contain trace amounts of albumin arising from the cell culture medium used during the step of production of these recombinant proteins.

Recombinant human FVIII still needs to be optimized. Indeed, FVIII is relatively unstable in physiologic conditions, has a low activity in blood, is present at very low concentrations (0.1 to 0.2 µg/ml), and has a half-life of 10 to 12 hours.

In about 30% of severe hemophiliac A patients, replacement therapy causes complications specific to FVIII which lead to failure of the treatments usually used. In fact, after replacement therapy, patients may develop antibodies directed against the exogenous recombinant FVIII. These anti-FVIII antibodies inhibit the procoagulant activity of FVIII, hence the name "inhibitory antibodies" or else "inhibitors". Further FVIII perfusion are rendered ineffective by these antibodies, and result in an increase of inhibitory antibody amount through a phenomenon known as "anamnestic reaction".

Rapidly, patients can no longer be treated with FVIII, in which case the inhibitor "titer" is determined. This titer is expressed in international Bethesda units (BU). One BU of inhibitors corresponds to inactivation of half of the amount of FVIII in 1 ml of normal plasma. A titer is "low" when less than 10 BU, and "high" when more than 10 BU.

When the inhibitor titer is relatively low, hemophiliac patients may be given the aforementioned FVIII concentrates such as Kogenate® FS, Helixate® FS, Recombinate®, and ReFacto$^{MC}$, but this carries a significant risk of inducing a rise in inhibitor titers which must therefore be closely monitored.

One of the ways to control inhibitory antibodies is to induce immune tolerance through administration of large doses of FVIII according to "de Bonn" protocol. In some patients, the inhibitory antibody titer is so high that they cannot be treated with large doses of FVIII for toxicity reasons.

A second approach known as the "Bonn-Malmo protocol" is based on one hand on ex vivo immunoadsorption of inhibitors immediately followed by reinjection of the blood, and on the other hand on injection of large doses of FVIII combined with immunosuppressive agents. These treatments are extremely costly in terms of recombinant FVIII and have achieved partial success.

Another approach consists in supplying coagulation factors in order to "bypass" the requirement of FVIII in the intrinsic coagulation pathway by using: i) plasma-derived activated prothrombin complex (FEIBA® VH, Factor Eight Inhibitor Bypassing Activity; Baxter) containing Factors II, VII, IX and X; ii) recombinant activated Factor VIIa (rFVIIa; NovoSeven®/Niastase®; NovoNordisk).

Said approaches have clear-cut success, nevertheless counterbalance by the development of side effects associated with this type of therapy (such as additional bleeding or conversely thrombotic events related to the frequency of administration).

It should be noted that circulating FVIII level increases after injection and then gradually declines related to its half-life. FVIII half-life ranges from 8 to 16 hours, with an average of 12 hours, raising the problem of repeated injections.

Another option consists in using a porcine FVIII with the aim to avoid antibodies directed against human FVIII. Patients who developed inhibitors to human FVIII have been successfully treated with semi-purified porcine FVIII (Hyate:C). Yet, this success has only been partial because after several injections of porcine FVIII, anti-porcine FVIII inhibitors have also developed, as mentioned in US2004/0249134. This phenomenon may necessitate to end treatment. Ipsen and Octagen are now co-developing a recombinant porcine FVIII known as OBI-1 in collaboration with Emory University in the USA, as a replacement for Hyate:C (WO2005107776).

Administration of porcine FVIII is therefore not a definitive solution for the treatment of hemophilia A patients with inhibitors.

As it can be seen, today there is no ideal treatment for individuals with hemophilia A, with or without inhibitors. The various problems encountered with commercial FVIII-based treatments associated with the development of these inhibitory antibodies have driven efforts to rapidly design a novel FVIII which has retained procoagulant specific activity and having lost the epitopes recognized by the inhibitory antibodies.

Few studies have addressed the epitope specificities of "inhibitory" antibodies. Some inhibitory antibodies appear to recognize small regions of the FVIII molecule: i) C2 domain in the light chain (2181-2321); ii) A2 domain in the heavy chain (484-509); iii) A3 domain (1694-2019) (Prescott et al., 1997, Blood, 89:3663-3671; Barrow et al., 2000, Blood, 95:557-561).

The 18 kDa C2 domain, between Serine 2173 and Tyrosine 2332, contains the membrane phospholipid binding domain and a part of the vWF binding domain. Inhibitory antibodies directed against the C2 domain mainly block the binding to phospholipids binding required for procoagulant activity but also the interaction with vWF. Mutations at positions Methionine 2199, Phenylalanine 2200, Valine 2223, Lysine 2227, Leucine 2251 and Leucine 2252 illustrate the importance of these amino acids in FVIIII activity and binding to phospholipids and/or to vWF (Pratt et al., 1999, Nature, 402: 439-442).

Anti-A2 antibodies inhibit the function of FVIIIa as cofactor of Factor X (Lollar et al., 1994, J. Clin. Invest. 93:2497-2504). The main A2 epitope has been located between Arginine 484 and Leucine 508 (Healey et al., 1995, J. Biol. Chem., 270:14505-14509).

Antibodies directed against A3 and/or C2 domain prevent stabilization of the interaction between FVIII and vWF and also interfere with binding of the FVIII light chain to activated FIX.

Inhibitors are very heterogeneous from one patient to another and epitope specificity may change over time. Kinetic study of FVIII inhibition have revealed two types of allo-antibodies: type I antibodies which completely neutralize exogenous FVIII, and type II antibodies which never totally inhibit FVIII activity. Type II antibodies not completely block the procoagulant activity of FVIII because they are not saturable or display decreasing affinity according to their concentration.

Regions which can be recognized by inhibitory antibodies are cited in patents US2003/147900 and WO00/48635. These exposed and antigenic FVIII regions are between positions 1649-2019, 108-355, 403-725 and 2085-2249.

Moreover, US 2005/0256304 describes the following set of positions in human FVIII, where substitutions are likely to decrease antigenicity: 197, 198, 199, 201, 202, 407, 411, 412, 419, 515, 517, 613, 617, 636, 637, 638, 639, 823, 1011, 1013, 1208, 1209, 1210, 1254, 1255, 1257, 1262, 1264, 1268, 1119, 1120, 1121, 1122, and 1123.

The antigenicity of human FVIII can be decreased by glycosylation of recognition sites of inhibitors. Said method is disclosed in U.S. Pat. No. 6,759,216 and JP2004141173.

Another option consists in substituting the human FVIII epitopes usually recognized by inhibitors in domains: i) A2 (484-509); ii) A3 (1694-2019), a3 (1649-1687); iii) C2 (2181-2321). This solution is based on the use of a hybrid recombinant protein: a human/porcine FVIII.

The main targets of inhibitory antibodies are located in the A2 and C2 domains of FVIII (Saenko et al., Haemophilia, 2002). In fact, it is generally thought that 90% of inhibitory antibodies are directed against the human A2 and C2 domains (Barrow et al., 2000, Blood, 95:564-569). Moreover, it has been shown that human inhibitors have weak activity against porcine FVIII (Koshihara et al., Blood, 1995).

It is therefore expected that a substitution of human FVIII epitopes by porcine sequences would lead to a hybrid molecule less reactive towards inhibitory antibodies. Thus, the human A2 and C2 domains were replaced by their corresponding porcine domains (Lubin et al., 1994, J. Biol. Chem., 269:8639-8641). However, once again, anti-porcine FVIII antibodies eventually developed during the treatment of patients with inhibitors.

Many patents describe human/animal FVIII hybrids having retained a procoagulant activity. Human/animal hybrid, as used herein, denotes any combination (substitution) of at least one amino acid between a human FVIII sequence and a FVIII sequence of animal origin. Said hybrids have been produced, on the one hand, by substituting regions (functional subunits or structural domains) by the corresponding animal regions. For instance, U.S. Pat. Nos. 5,888,974; 5,663,060; 5,583,209; EP1359222; U.S. Pat. No. 5,744,446; WO93/20093; and WO95/24427 provide hybrid FVIII molecules derived from combinations of heavy and light chains of human and non-human FVIII, and/or derived from combinations of human/porcine FVIII domains.

U.S. Pat. No. 5,744,446 describes human/porcine FVIII variants wherein sequences of the human A2 domain are substituted by the corresponding murine or porcine sequences. The substituted fragments of the A2 domain are: 373-540; 373-508, 445-508, 484-508, 404-508, 489-508 and 484-489.

U.S. Pat. No. 5,364,771 provides a method for purifying FVIII hybrids derived from combinations of light and heavy chains from human and non-human FVIII: human FVIII in which the A2 domain is replaced by the porcine A2 domain.

On the other hand, in some patents, said hybrids are formed by point substitutions of one or several amino acids of human FVIII by the corresponding amino acid(s) of animal origin (porcine, canine or murine). For example, US2004/0197875 discloses modifications in codon charges at certain positions of human FVIII. Said positions are defined related to porcine FVIII sequence. EP1454916 describes the introduction of porcine codons into the human cDNA.

Among these patents, studies have been addressed to develop human/porcine FVIII hybrids in the region of the A2 domain. EP1359222 describes a study of the porcine A2 domain sequence, with a view to generating such hybrid. US2003/166536; U.S. Pat. No. 6,376,463; WO00/71141 describe amino acid substitutions in human FVIII at key epitopes in the A2 domain, between positions 484 and 508: 486, 490, 491, 493, 494, 496, 498, 499, 500, 502, 503, 504, 505, 506, 507 for WO00/71141; and 485, 487, 488, 489, 492, 495, 501, 508 for U.S. Pat. No. 5,859,204. In particular, Alanine substitutions were made at positions: Arginine 484, Proline 485, Tyrosine 487, Serine 488, Arginine 489, Proline 492, Valine 495, Phenylalanine 501, and Isoleucine 508. These substitutions conferring decreased antigenicity might be of interest from a therapeutic standpoint.

Likewise, in U.S. Pat. No. 6,180,371, Arginine 484 is substituted by Serine, Proline 485 by Alanine, Arginine 489 by Glycine, Proline 492 by Leucine. With these variants, inhibition of the procoagulant function of FVIII by antibodies was alleviated or disappeared altogether. The therapeutic interest of a double or triple mutant at Arginine 484, Arginine 489 and Phenylalanine 501, where each codon is substituted with an Alanine, is suggested.

There are also patents disclosing FVIII variants in which the substitutions only affect the C2 domain.

US2004/249134; WO03/047507; WO02/24723; U.S. Pat. No. 6,770,744 describe substitutions at positions Methionine 2199, Phenylalanine 2200, Valine 2223, Lysine 2227, Leucine 2251 and Leucine 2252. Said substitutions were introduced into a FVIII lacking the B domain. Amino acids at positions 2215, 2220, 2320, 2195, 2196, 2290 and 2313 were substituted with an Alanine.

With regard to position 2223, Valine is replaced by an Alanine, by comparison between human and porcine FVIII. This mutation is mentioned in Pratt's article "Structure of the C2 domain of human FVIII" (Nature, 1999, 402:439-442) and in U.S. Pat. No. 6,770,744.

Combinations of certain mutated positions such as 2199, 2200, 2223 and 2227 have been described as reducing the antigenicity of FVIII with regard to some anti-C2 domain inhibitory antibodies, all while retaining the coagulant activity of FVIII.

In patents WO99/46274 and US2005/0079584, J. Lollar's group describes a region of potential interest for constituting a less immunogenic FVIII: 2181 to 2243. This region was defined very roughly by an antigenicity study of human/porcine hybrids. An alignment between human and porcine FVIII of the sequence 2181 to 2243 disclosed 17 differences at the following positions: 2181, 2182, 2195, 2196, 2197, 2199, 2207, 2216, 2222, 2224, 2225, 2226, 2227, 2228, 2234, 2238, 2243. J. Lollar's group speculate that a substitution at these 17 positions by an Alanine, a Methionine, a Serine, a Glycine, or else a Leucine might generate a FVIII protein that can avoid inhibitory antibodies. This hypothesis is not supported by any antigenicity studies of mutants of interest.

Lastly, patents such as U.S. Pat. No. 6,180,371; US2002/182670; US 2003/068785; US2005/079584; WO99/46274;

U.S. Pat. No. 7,012,132; WO2005/046583 provide human/ porcine hybrids harboring substitutions in both the A2 and C2 domains of FVIII with the aim of reducing inhibition by inhibitory antibodies that recognize both domains. In particular, WO2005/046583 describes amino acid substitutions in the A2 and C2 domains at positions 484, 489, 492, 2199, 2200, 2251 and 2252. The FVIII which was used lacks the B domain. Only position 484 has an Arginine substituted by an Alanine.

To summarize, while many studies make reference to novel FVIII variants, there is still a need for a novel, less immunogenic FVIII, because there are no modified FVIII variants capable of treating patients with inhibitors currently on the market. Moreover, variants with an improved specific activity or an improved capacity to be secreted are also of major interest to promote the production of recombinant FVIII or to improve the treatment of patients.

SUMMARY OF THE INVENTION

The present invention therefore provides novel improved FVIII variants. Said variants may have lost the epitopes recognized by inhibitory antibodies all while retaining the core of their procoagulant activity, or have an improved specific activity, or else have a improved secretion capacity. Said variants may also have a combination of these features. For example, the invention relates to variants which are less immunogenic and have an improved specific activity and/or an improved secretion capacity. Likewise, the invention relates to variants having an improved specific activity and/or an improved secretion capacity.

A first object of the present invention is an improved human FVIII variant or a biologically active derivative thereof comprising a substitution of at least one amino acid selected from the group consisting of the residues at positions 462, 409, 507, 629, 400, 562, 403, 518, 414, 496, 421, 493, 486, and 494 of the A2 domain and the residues at positions 2206, 2212, 2226, 2244, 2261, 2275, 2280, 2281, 2282, 2289, 2294, 2311, 2312, and 2316 of the C2 domain. In a particular embodiment, the human FVIII variant or biologically active derivative thereof consists of a single substitution. In another particular embodiment, the human FVIII variant or biologically active derivative thereof further comprises a substitution of at least one amino acid selected from the group consisting of the residue at position 2202 of the C2 domain and the residue at position 437 of the A2 domain. In a particular embodiment, the human FVIII variant or biologically active derivative thereof comprises the substitution of at least two, three, four, five six, seven, eight, nine, ten, eleven, twelve, thirteen, fourteen or fifteen amino acids, preferably selected from the aforementioned groups. Preferably, the amino acid is substituted by an amino acid selected from an Alanine, a Methionine, a Serine, a Glycine, and a Leucine. More preferably, the amino acid is substituted by an Alanine. Preferably, the biologically active FVIII derivative is a FVIII consisting in a partial or whole deletion of the B domain.

In a particular embodiment, the variant has decreased antigenicity towards inhibitory antibodies as compared to natural human FVIII and retains a procoagulant activity at least equal to 50% of that of natural human FVIII. In a preferred embodiment, the invention relates to an improved human FVIII variant or a biologically active derivative thereof comprising a substitution of at least one amino acid selected from the group consisting of the residues at positions 462, 409, 507 and 629 of the A2 domain and the residues at positions 2289, 2294, 2312, and 2316 of the C2 domain. Said variant can further comprise a substitution of at least one amino acid selected from the group consisting of the residue at position 2202 of the C2 domain and the residue at position 437 of the A2 domain. In a more preferred embodiment, the invention relates to an improved human FVIII variant or a biologically active derivative thereof comprising the substitution of at least one amino acid selected from the group consisting of the residues at positions 462, 409, 507 and 629 of the A2 domain. In another embodiment, the invention relates to an improved human FVIII variant or a biologically active derivative thereof comprising or consisting of the combination of two substitutions selected from the group consisting of 409+462, 409+507, 462+507, 409+629, 462+629, 507+629. In yet another embodiment, the invention relates to an improved human FVIII variant or a biologically active derivative thereof comprising or consisting of the combination of three substitutions selected from the group consisting of 409+462+ 507, 462+507+629, 409+462+629, 409+507+629. In another particular embodiment, the invention relates to an improved human FVIII variant or biologically active derivative thereof comprising or consisting of the combination of four substitutions at positions 409, 462, 507 and 629.

Furthermore, these mutations which confer abolition to inhibition by inhibitory antibodies may prove to be of great interest in combination with mutations conferring a higher specific activity, allowing compensating an optional relative loss of activity of these less antigenic mutants. In a particular embodiment, the variant has an improved specific activity as compared to that of natural human FVIII. In a preferred embodiment, the invention relates to an improved human FVIII variant or a biologically active derivative thereof further comprising the substitution of at least one amino acid selected from the group consisting of the residues at positions 2177, 2183, 2186, 2191, 2196, 2204, 2205, 2213, 2217, 2235, 2258, 2264, 2268 and 2269 of the C2 domain.

Said mutations which confer abolition to inhibition by inhibitory antibodies may also prove to be of great interest in combination with mutations conferring an improved capacity to be secreted, by allowing compensating an optional relative loss of secretion of these less antigenic mutants. In a particular embodiment, the invention relates to an improved human FVIII variant or a biologically active derivative thereof further comprising the substitution of at least one amino acid selected from the group consisting of the residues at positions 2175, 2199, 2200, 2215, 2251, 2252 and 2278 of the C2 domain. Massive production of mutants having retained at least 50% of FVIII activity also makes it possible to encompass their use in a context of analyzing additional functions of the protein. In addition to a modulation of its immunogenicity, secretion and specific activity, the following properties of FVIII might be improved by using the herein described mutated molecules: —binding to von Willebrand factor and therefore improved half-life of FVIII or circulating FVIIIa; —improved intrinsic stability of the molecule by stabilization of the A2 domain and therefore an increased efficiency period; —binding to phospholipids derived from blood platelets, cell surfaces or circulating microparticles and therefore improved formation of FXa; —binding to FIXa and FX and therefore improved formation of FXa; —decreased binding of FVIII or FVIIIa to the molecules responsible for its catabolism such as for example low density Lipoprotein Receptor-related Protein (LRP), Low density Lipoprotein Receptor (LDLR), Very Low Density Lipoprotein Receptor (VLDLR), megaline or any other receptor which might be identified and therefore improved half-life of circulating FVIII; —proteolysis decrease of FVIII or FVIIIa by vascular proteases such as for example activated protein C, FXa, FIXa, and therefore increase efficiency period.

A second object of the present invention relates to a nucleic acid coding for a human FVIII variant or a biologically active derivative thereof according to the invention, an expression cassette comprising said nucleic acid, a vector, preferably an expression vector, comprising said nucleic acid or said expression cassette, and a host cell comprising a nucleic acid, an expression cassette or a vector according to the present invention. Preferably, the vector can be selected from a plasmid and a viral vector. The present invention also relates to the use of a nucleic acid, an expression cassette, an expression vector or a host cell according to the invention for producing a human FVIII variant or a biologically active derivative thereof according to the present invention.

A third object of the present invention relates to a pharmaceutical composition comprising a human FVIII variant or a biologically active derivative thereof according to the invention. Thus, the present invention relates to a human FVIII variant or a biologically active derivative thereof according to the invention as medicament. The present invention further relates to a human FVIII variant or a biologically active derivative thereof according to the invention for the treatment of hemophilia A. The treatment can be curative or preventive. In a particular embodiment, the patient to be treated is a patient with inhibitors. In another embodiment, the patient to be treated is a hemophiliac patient before any development of inhibitors. The present invention equally relates to a method for treating hemophilia A comprising administering a human FVIII variant or a biologically active derivative thereof according to the present invention.

A fourth object of the present invention relates to the use of a human FVIII variant or a biologically active derivative thereof according to the invention for preparing a medicament for the treatment of hemophilia A. The treatment can be curative or preventive. In a particular embodiment, the patient to be treated is a patient with inhibitors. In another embodiment, the patient to be treated is a hemophiliac patient before development of any optional inhibitors. The present invention also relates to a method for treating hemophilia A comprising administering a human FVIII variant or a biologically active derivative thereof according to the present invention.

A fifth object of the present invention relates to the use of one or more human FVIII variants or a biologically active derivative thereof according to the present invention for the diagnosis of inhibitor type in a patient with hemophilia A.

BRIEF DESCRIPTION OF FIGURES AND TABLES

FIG. 1: Simplified scheme of the coagulation cascade. Ca: calcium-dependent step. PL: phospholipids of blood platelet membrane. TF: tissue factor. TFPI: tissue factor pathway inhibitor. The role of FVIIIa is to increase the catalytic efficiency of FIXa to activate FX. Assembly of FXa and FVa triggers a significant increase in thrombin formation.

FIG. 2A-2E: Primary screen results: Raw activities of 359 Alanine mutants over the 795 produced=functional mapping of FVIII activity of these 359 positions.

Figure 3:
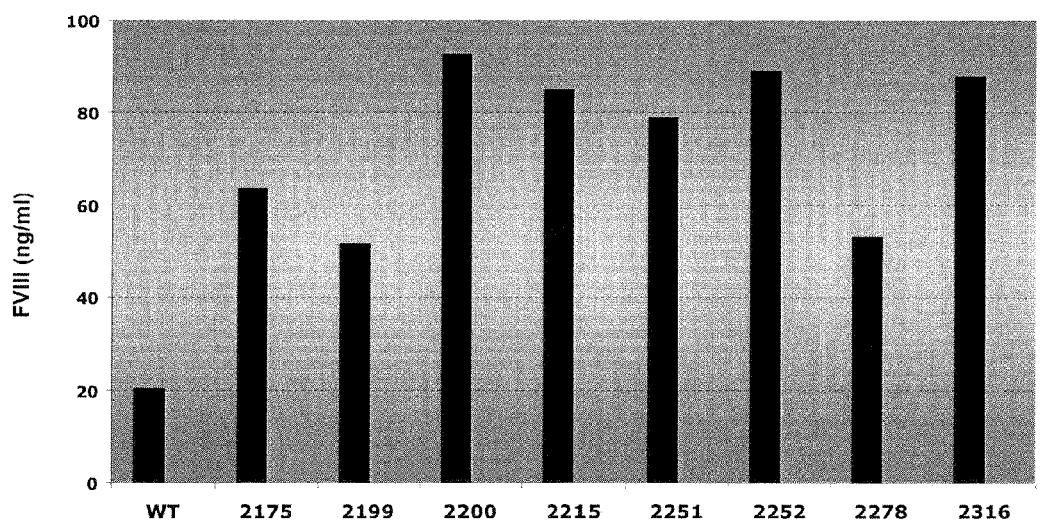

FIG. 3: Production of FVIII in culture medium; 8 mutants displayed a much higher production level than non-mutated FVIII in the same conditions.

FIG. 4: Highest specific activities of 15 mutants compared to non-mutated FVIII in the same conditions.

Figure 5:
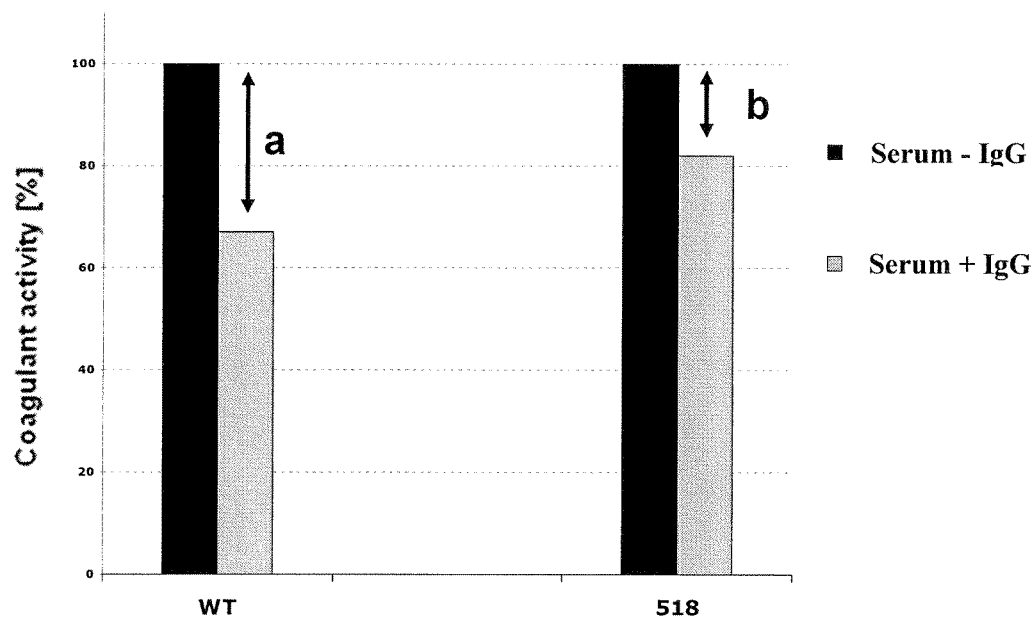

FIG. 5: Example of determining abolition of the serum TD to inhibition by FVIII mutant E518A. Abolition to inhibition is expressed as a percentage: [(b−a)/a]×100; where "a" represents residual activity percentage of the WT (serum+IgG/serum−IgG) and "b" is the residual activity percentage of the mutant (serum+IgG/serum−IgG).

FIG. 6A-6E: Abolition of FVIII-4A2 versus wild-type FVIII to inhibition by inhibitory antibodies from five patients (TD, GC, PR, SL and FS) measured by Bethesda assay.

Residual activity, determined after incubation with inhibitory antibodies, is divided by remained activity after incubation with a non-immune antibody; the residual activity percentage is thus determined.

FIG. 7A-7B: Determining the inhibition decrease of the FVIII-4A2 mutant by anti-A2 domain antibody (GMA012) and a rabbit polyclonal antibody.

FIG. 8A-8B: Comparative titration on a solid support of FVIII-4A2 versus wild-type FVIII by ELISA using anti-C2 domain antibody (ESH4) and anti-A2 domain antibody (GMA012).

FIG. 9: Comparative determination of FVIII-4A2 and wild-type FVIII activation by thrombin.

FIG. 10: Comparative determination of A2 domain dissociation and resultant loss of activity for FVIII-4A2 and wild-type FVIII after activation by thrombin (IIa).

FIG. 11A-11D: Abolition of FVIII-3A2 versus wild-type FVIII to inhibition by inhibitory antibodies from four patients (TD, GC, SL and FS) measured by Bethesda assay.

FIGS. 12-14: Primary screen results; list of 158 Alanine mutants selected for secondary screening, having retained at least 50% of raw activity relative to non-mutated FVIII activity.

FIGS. 15-18: Secondary screening: Bethesda assays on 30 mutants displaying modified antigenicity towards sera from five hemophiliac patients with inhibitors. Results are expressed as the abolition to inhibition percentage for each mutant as exemplified in FIG. 5.

FIG. 19: Comparison of specific activity and raw activity relative to non-mutated FVIII activity for the 30 mutants displaying modified antigenicity towards sera from five hemophiliac patients with inhibitors.

FIG. 20: List of all FVIII double mutants produced from the eight single mutants FVIII409A, FVII1462A, FVIII507A, FVIII629A, FVIII2289A, FVIII2294A, FVIII2312A and FVIII2316A.

FIG. 21: Chromogenic specific activities and abolition to inhibition percentages towards inhibitory antibodies of six double A2 mutants from sera of four hemophiliac patients TD, GC, SL and PR.

Description of the invention

The present invention provides a solution to resolve a serious complication that occurs in 30% of hemophilia A patients treated with recombinant FVIII: the development of an immune response induced by the treatment and directed against the exogenous recombinant FVIII. The solution provided consists in generating recombinant human FVIII molecules having decreased antigenicity of the epitopes usually recognized by inhibitory antibodies. The FVIII variants of the invention have lost one or more epitopes usually recognized by said antibodies.

The present invention provides other solutions consisting in generating human FVIII variants having an improved specific activity as compared to natural FVIII.

Lastly, the present invention provides with FVIII variants having a greater capacity to be secreted, which is interesting for the production of recombinant FVIII and in a potential gene therapy.

The different properties conferred by the mutations in these variants may be of major interest in combination. In a non-limiting example, mutations which confer a specific activity improvement of a variant could compensate an optional relative loss of activity in variants whose mutations confer a abolition to inhibition by inhibitory antibodies and being therefore less antigenic. In another non-limiting example, mutations which confer a higher capacity to be secreted may interesting in combination with mutations conferring an abolition to inhibition by inhibitory antibodies, by allowing, for example, to compensate a optional relative loss of secretion of said less antigenic mutants.

In the present document, the following terminology is used to designate a substitution: 5409A indicates the substitution of the serine residue at position 409 of SEQ ID No. 3 by an alanine. Substitution refers to the replacement of an amino acid residue by another one selected from the other 19 amino acids or by a non- naturally occuring amino acid. The terms "substitution" and "mutation" are interchangeable. The sign "+" indicates a combination of substitutions.

"Comprise" means that the variant or the fragment thereof has one or more substitutions such as indicated with reference to SEQ ID No. 3, but that the variant or the fragment thereof may have other modifications, particularly substitutions, deletions or insertions.

the chromogenic assay mentioned above. This assay was also performed on the robotic platform of the National Hemophilia Treatment Center (Hospices Civils de Lyon). The chromogenic activity of the 158 selected Alanine mutants was carried out with the Coamatic Factor VIII kit (Chromogenix, Instrumentation Laboratory, Milan, Italy) according to the supplier's instructions. Briefly, culture supernatants (50 μl) were diluted in the dilution buffer provided and preincubated at 37° C. for 4 min. The reaction medium (50 μl), preheated at 37° C., was then added for 4 min, after which 50 μl of development medium at 37° C. were added. The formation of product over time was measured immediately on a spectrophotometer at 405 nm after shaking the microtiter plate. Product formation is expressed as mUOD/min. When values were greater than 200 mUOD/min, the assay was repeated using a higher dilution.

FIGS. 12-14 show the activities of the 158 mutants which retained more than 50% of non-mutated FVIII activity. Said 158 mutants were selected for the secondary screening.

Example 4: Secondary screen: Evaluation of loss of antigenicity towards human FVIII inhibitory antibodies The secondary screen correlates to an assay similar to the Bethesda assay, carried out as described below on the 158 mutants selected following the primary screening; said assay comprises a step of contacting a inhibitory serum (or antibody) with a FVIII molecule to be tested or a reference standard and a step of measuring FVIII coagulant activity by chronometric assay.

Culture supernatants obtained after 48 h of contact with COS cells transfected by different FVIII constructs were used. Said supernatants were produced in complete medium [(IMDM, Invitrogen), 10% fetal calf serum, 2 mM L-glutamine, 100 U/ml penicillin, 100 mg/ml streptomycin]. Supernatants were diluted in fresh complete medium to obtain a final chronometric activity comprised in the range of about 10-20% (1 FVIII unit =100% activity =200 ng/ml). The culture supernatant diluted or not (140 μl) was added to 150 μl of FVIII-depleted human plasma (Stago, Asnieres, France). An antibody dilution (10 μl) was then added to the mix. These antibodies are IgG fractions purified on protein A- from hemophiliac patients with inhibitors. An IgG fraction from a non-hemophiliac control was similarly obtained. Bethesda inhibitor titers were identical to the inhibitory activity from the plasma. The purification protocol therefore did not affect the inhibitory activity of the antibodies. The antibodies were first diluted in fresh complete medium, the measurement being carried out either with a fixed antibody dilution or with serial dilutions. The fixed antibody concentration which was used was that which produced 50% inhibition of a recombinant FVIII standard solution with 12.5% activity. Samples were incubated in a 37° C. water-bath for 1h30. Coagulant activity was then determined on a MDA-II apparatus (BioMérieux, Marcy-l'Etoile) and compared to that of a standard curve established from an identical FVIII stably produced in the CHO cell line. Results are expressed as a percentage which represents the abolition to inhibition of coagulant activity of a given mutant by inhibitory antibodies from a patient's serum. Said percentage was calculated as shown in FIG. 5 for the FVIII mutant E518A. Abolition to inhibition expressed is a percentage $=-[(b-a)/a] \times 100$; where "a" is the percentage residual activity of the WT (serum + IgG / serum—IgG) and "b" is the percentage residual activity of the mutant (serum + IgG/serum −IgG).

FIGS. 15-18 show for 30 single mutants the percentages of abolition to inhibition for sera from five hemophiliac patients. Said mutants were selected in the secondary screen of the 158 mutants selected in the primary screen. Several mutants show a high percentage of abolition to inhibition with certain sera, such as mutant 2316 for sera TD and SL, mutant 2294 for serum GC, mutant 403 for serum FS and mutant 2275 for serum PR.

Patients' sera were selected for their high Bethesda titers (greater than 10 BU) and their different inhibitor profiles. These patients can no longer be treated with FVIII injections and need bypassing agents. Thus, obtaining FVIII Alanine mutants which abolish, even partially, the inhibition of FVIII activity by the inhibitory antibodies of one of these patients, is a major step forward to the future approaches of treating hemophiliac patients with inhibitors. The different data obtained on a large number of mutants as well as the different sera tested will make it possible to create combinations of mutations leading to an improved FVIII which can avoid a majority of inhibitory antibodies while retaining its procoagulant activity.

The reproducibility of FVIII expression level related to transfections was controlled by following the specific activity of wild-type FVIII. Indeed, specific activities calculated from antigen determinations (Stago commercial ELISA kit) were identical for wild-type FVIIIs produced in different transfections. Likewise, antigen concentrations were determined for mutants having retained at least 50% of wild-type FVIII activity and their specific activity was determinate throw. Specific activity corresponds to raw activity measured in the chromogenic assay (mUOD/min) relative to protein concentration (ng/ml) obtained with an ELISA kit (Stago FVIII kit). FIG. 19 shows comparative data of raw and specific activities of 30 mutants selected in the secondary screen.

The eight FVIII Alanine mutants 2175, 2199, 2200, 2215, 2251, 2252, 2278 and 2316 displayed a far above average capacity to be secreted in the COS cell production medium used in the scope of the present invention. FIG. 3 depicts the data obtained for these eight mutants. Raw coagulant activity of these mutants was determined by chromogenic assay. Their concentration was approximately two to four times higher than that of wild-type FVIII. This property is interesting for producing recombinant FVIII and might make it possible to lower production costs of a new generation FVIII. Also, it might be advantageous in a gene therapy for hemophiliac patients. Moreover, these mutations which confer a greater capacity to be secreted may be of major interest in combination with mutations conferring abolition to inhibition by inhibitory antibodies, by allowing, for example, to compensate an optional relative loss of secretion of said less antigenic mutants.

The 15 mutants 2177, 2183, 2186, 2191, 2196, 2204, 2205, 2206, 2213, 2217, 2235, 2258, 2264, 2268 and 2269 displayed far higher specific activity than wild-type FVIII, while maintaining a high production level, around to that of wild-type FVIII (concentration greater than 10 ng/ml). The specific activities of these 15mutants are given in FIG. 4. Raw coagulant activity of these mutants was determined by chromogenic assay. This property is interesting because it would allow smaller or less frequent doses of FVIII to be injected in patients. Moreover, these mutations which confer a higher specific activity might be of major interest in combination with mutations conferring abolition to inhibition by inhibitory antibodies, by allowing to compensate an optional relative loss of activity of said less antigenic mutants.

Example 5: Selection and combination of the best single mutants selected in the secondary screen Among the 30 single mutants selected in the secondary screen, eight were chosen in order to combine their respective mutations, to obtain a cumulative/additive effect of remarkable properties of each. The selection criteria for these mutants were complex and considered the following parameters:

- at least 25% abolition to inhibition for at least one of the test sera from hemophiliac patients with inhibitors;
- raw coagulant activity at least 100% relative to non-mutated FVIII; and
- reproducibly good level of expression.

The eight selected mutants were mutants 409, 462, 507 and 629 in the A2 domain and mutants 2289, 2294, 2312 and 2316 in the C2 domain. As noted earlier, the selection criterion considered of a high specific activity (coagulant activity relative to expression level), as shown in FIG. 19. This specific activity level had to be constant in the different experiments.

The 28 double mutants resulting from the combination of the eight single mutations 409, 462, 507, 629, 2289, 2294, 2312 and 2316 (six A2 double mutants +six C2 double mutants +sixteen A2-C2 double mutants presented in FIG. 20) were constructed by mutagenesis methods known to one skilled in the art. These mutants were transiently expressed in COS-7 mammalian cells as described in Example 2. Their expression level and their activity level were determined as described in the previous examples, respectively by ELISA and chromogenic assay (mUOD/min). These 28 mutants were then assessed for their abolition to inhibition by antibodies from hemophiliac patients. The A2 double mutants displayed a significant abolition to inhibition for one or all of the antibodies from the patients' sera, whereas the combinations containing C2 domain mutations (six C2 double mutants +sixteen A2-C2 double mutants) displayed an insignificant or null abolition to inhibition.

FIG. 21 shows the specific activities of the six A2 double mutants and their percentage of abolition to inhibition by sera from four hemophiliac patients TD, GC, SL and PR calculated as in Example 4. Especially preferred double mutants significantly abolished antibodies from a minimum of three over the four patients. This illustrates the cumulative effect of the four single mutations in the A2 domain. The choice was therefore based on the combination of the four mutations 409, 507, 462 and 629. Triple mutants and the quadruple mutant comprising these four mutations 409, 507, 462 and 629 were also constructed.

Residual activity, determined after incubation with inhibitory antibodies, is divided by remained activity after incubation with a non-immune antibody to give the residual activity percentage.

Table 1: Primary screen results; list of 158 Alanine mutants selected for secondary screening, having retained at least 50% of raw activity relative to non-mutated FVIII activity.

Table 2: Secondary screening: Bethesda assays on 30 mutants displaying modified antigenicity towards sera from five hemophiliac patients with inhibitors. Results are expressed as the abolition to inhibition percentage for each mutant as exemplified in FIG. 5.

Table 3: Comparison of specific activity and raw activity relative to non-mutated FVIII activity for the 30 mutants displaying modified antigenicity towards sera from five hemophiliac patients with inhibitors.

Table 4: List of all FVIII double mutants produced from the eight single mutants FVIII409A, FVIII462A, FVIII507A, FVIII629A, FVIII2289A, FVIII2294A, FVIII2312A and FVIII2316A.

Table 5: Chromogenic specific activities and abolition to inhibition percentages towards inhibitory antibodies of six double A2 mutants from sera of four hemophiliac patients TD, GC, SL and PR.

DESCRIPTION OF THE INVENTION

The present invention provides a solution to resolve a serious complication that occurs in 30% of hemophilia A patients treated with recombinant FVIII: the development of an immune response induced by the treatment and directed against the exogenous recombinant FVIII. The solution provided consists in generating recombinant human FVIII molecules having decreased antigenicity of the epitopes usually recognized by inhibitory antibodies. The FVIII variants of the invention have lost one or more epitopes usually recognized by said antibodies.

The present invention provides other solutions consisting in generating human FVIII variants having an improved specific activity as compared to natural FVIII.

Lastly, the present invention provides with FVIII variants having a greater capacity to be secreted, which is interesting for the production of recombinant FVIII and in a potential gene therapy.

The different properties conferred by the mutations in these variants may be of major interest in combination. In a non-limiting example, mutations which confer a specific activity improvement of a variant could compensate an optional relative loss of activity in variants whose mutations confer an abolition to inhibition by inhibitory antibodies and being therefore less antigenic. In another non-limiting example, mutations which confer a higher capacity to be secreted may be interesting in combination with mutations conferring an abolition to inhibition by inhibitory antibodies, by allowing, for example, to compensate an optional relative loss of secretion of said less antigenic mutants.

In the present document, the following terminology is used to designate a substitution: S409A indicates the substitution of the serine residue at position 409 of SEQ ID No. 3 by an alanine. Substitution refers to the replacement of an amino acid residue by another one selected from the other 19 amino acids or by a non-naturally occurring amino acid. The terms "substitution" and "mutation" are interchangeable. The sign "+" indicates a combination of substitutions.

"Comprise" means that the variant or the fragment thereof has one or more substitutions such as indicated with reference to SEQ ID No. 3, but that the variant or the fragment thereof may have other modifications, particularly substitutions, deletions or insertions.

"Consists of" means that the variant or the fragment thereof contains only the substitution(s) indicated with reference to SEQ ID No. 3.

"Variant" refers in particular to a polypeptide which differs from a polypeptide represented by sequence SEQ ID No. 3 by at least 1, 2, 3, 4, 5, 6, 7, 8, 9, 10, 11, 12, 13, 14 or 15 residue(s), preferably by 1, 2, 3, 4, 5, 6, 7, 8, 9 or 10 residues.

Amino acids of the A2, A3 or C2 domains of FVIII were systematically substituted by an Alanine. The production of these human FVIII mutants was carried out in mammalian cells. The primary screening of these variants was based on their procoagulant activity. The raw activity of each mutant was measured by chromogenic assay and compared with chromogenic assay of non-mutated human FVIII as reference. The activity of the FVIII variants can be determined by any method known to one skilled in the art, preferably according to method described in example 3 herein after. The FVIII variants selected as being the most active in the primary screen were then assessed for a second feature: loss of antigenicity towards sera from hemophiliac patients selected for their capacity to inhibit FVIII activity. Said secondary screening with said antibodies corresponds to a modified Bethesda assay. The antigenicity modification of the FVIII variants can be determined by any method known to one skilled in the art, preferably according to the method described in example 4 below.

Improved variants could be selected. Not only did some of these candidate medicaments retain a coagulant activity, but they also partially avoided inhibition by inhibitory antibodies from the sera of selected hemophiliac patients. These FVIIIs have lost one or more epitopes usually recognized by inhibitory antibodies from patients' sera. Furthermore, the candidate medicaments had a specific coagulant activity higher to that of wild-type FVIII. Another interesting feature is that the candidate medicaments displayed an improved secretion capacity.

In one embodiment, the invention therefore relates to recombinant human FVIII variants having lost at least one of the epitopes usually recognized by anti-FVIII antibodies known as "inhibitors", while retaining a coagulant activity, preferably higher, similar or close to that of non-mutated FVIII.

The present invention describes human FVIII variants comprising at least one substitution of an amino acid by an Alanine or any other amino acid in the C2 and A2 domains.

In particular the invention describes 158 Alanine mutants of human FVIII. "Alanine mutant", as used herein, denotes a mutant comprising the substitution of an amino acid by an Alanine residue. In particular, said mutants have an Alanine substitution at a residue located among the positions 2316, 2177, 2181, 2182, 2183, 2186, 2189, 2191, 2197, 2199, 2200, 2204, 2205, 2206, 2212, 2213, 2214, 2217, 2221, 2225, 2226, 2235, 2239, 2242, 2244, 2250, 2251, 2252, 2253, 2256, 2258, 2261, 2263, 2264, 2268, 2269, 2270, 2273, 2274, 2275, 2277, 2278, 2280, 2281, 2282, 2284, 2289, 2292, 2294, 2296, 2311, 2312, 2317, 2321 and 2324 of the C2 domain and the positions 378, 383, 391, 398, 399, 400, 403, 406, 407, 408, 409, 410, 413, 414, 415, 416, 417, 421, 429, 432, 440, 442, 444, 445, 449, 452, 454, 455, 462, 464, 468, 481, 486, 490, 491, 493, 494, 496, 497, 498, 499, 500, 507, 512, 517, 518, 519, 520, 523, 524, 526, 530, 532, 534, 539, 540, 543, 550, 552, 556, 559, 562, 567, 568, 573, 578, 588, 592, 596, 597, 600, 601, 602, 604, 607, 611, 621, 624, 628, 629, 632, 633, 640 and 642 of the A2 domain.

The positions of the residues are indicated with reference to the protein sequence of the 2332 amino-acid human FVIII, as illustrated in SEQ ID No. 3.

The invention relates to a human FVIII variant or a biologically active derivative thereof comprising a substitution of at least one amino acid of the C2 domain selected from the group consisting of the residues at positions 2316, 2177, 2181, 2182, 2183, 2186, 2189, 2191, 2197, 2199, 2200, 2204, 2205, 2206, 2212, 2213, 2214, 2217, 2221, 2225, 2226, 2235, 2239, 2242, 2244, 2250, 2251, 2252, 2253, 2256, 2258, 2261, 2263, 2264, 2268, 2269, 2270, 2273, 2274, 2275, 2277, 2278, 2280, 2281, 2282, 2284, 2289, 2292, 2294, 2296, 2311, 2312, 2317, 2321 and 2324. The variant can further comprise a substitution of at least one residue at position 2175, 2195, 2196, 2202, 2215 and 2222. The residue can be substituted by an amino acid selected from an Alanine, a Methionine, a Serine, a Glycine, and a Leucine, preferably an Alanine. Said amino acids, among the twenty naturally occurring amino acids, are known to decrease the antigenicity of a protein. The substitution or substitutions at these positions, in particular by an Alanine, result in an improved FVIII variant, in particular having lost one or more epitopes recognized by inhibitory antibodies and having retained its procoagulant activity. The present invention also relates to a FVIII light chain comprising a substitution of at least one amino acid of the C2 domain selected from the group consisting of the residues at positions 2316, 2177, 2181, 2182, 2183, 2186, 2189, 2191, 2197, 2199, 2200, 2204, 2205, 2206, 2212, 2213, 2214, 2217, 2221, 2225, 2226, 2235, 2239, 2242, 2244, 2250, 2251, 2252, 2253, 2256, 2258, 2261, 2263, 2264, 2268, 2269, 2270, 2273, 2274, 2275, 2277, 2278, 2280, 2281, 2282, 2284, 2289, 2292, 2294, 2296, 2311, 2312, 2317, 2321 and 2324. This light chain can further comprise a substitution of at least one residue at position 2175, 2195, 2196, 2202, 2215 and 2222.

The invention further relates to a human FVIII variant or a biologically active derivative thereof comprising or containing a substitution of at least one amino acid of the A2 domain, preferably selected from the group consisting of the residues at positions 378, 383, 391, 398, 399, 400, 403, 406, 407, 408, 409, 410, 413, 414, 415, 416, 417, 421, 429, 432, 440, 442, 444, 445, 449, 452, 454, 455, 462, 464, 468, 481, 486, 490, 491, 493, 494, 496, 497, 498, 499, 500, 507, 512, 517, 518, 519, 520, 523, 524, 526, 530, 532, 534, 539, 540, 543, 550, 552, 556, 559, 562, 567, 568, 573, 578, 588, 592, 596, 597, 600, 601, 602, 604, 607, 611, 621, 624, 628, 629, 632, 633, 640 and 642. The variant can further comprise a substitution of at least one residue at position 377, 379, 405, 434, 437, 485, 488, 489, 492, 495, 501, 508 and 623. The residue can be substituted by an amino acid selected from an Alanine, a Methionine, a Serine, a Glycine, and a Leucine, preferably an Alanine. The substitution or substitutions at these positions, in particular by an Alanine, result in an improved FVIII variant, in particular having lost one or more epitopes recognized by inhibitory antibodies and having retained its procoagulant activity. The present invention also relates to a FVIII heavy chain, optionally which totally or partially lacks the B domain, comprising a substitution of at least one amino acid of the A2 domain selected from the group consisting of the residues at positions 378, 383, 391, 398, 399, 400, 403, 406, 407, 408, 409, 410, 413, 414, 415, 416, 417, 421, 429, 432, 440, 442, 444, 445, 449, 452, 454, 455, 462, 464, 468, 481, 486, 490, 491, 493, 494, 496, 497, 498, 499, 500, 507, 512, 517, 518, 519, 520, 523, 524, 526, 530, 532, 534, 539, 540, 543, 550, 552, 556, 559, 562, 567, 568, 573, 578, 588, 592, 596, 597, 600, 601, 602, 604, 607, 611, 621, 624, 628, 629, 632, 633, 640 and 642. The variant can further comprise a substitution of at least one residue at position 377, 379, 405, 434, 437, 485, 488, 489, 492, 495, 501, 508 and 623.

The invention further relates to a human FVIII variant or a biologically active derivative thereof comprising a substitution of at least one amino acid comprising or containing a substitution of at least one amino acid selected from the group consisting of the residues at positions 2316, 2177, 2181, 2182, 2183, 2186, 2189, 2191, 2197, 2199, 2200, 2204, 2205, 2206, 2212, 2213, 2214, 2217, 2221, 2225, 2226, 2235, 2239, 2242, 2244, 2250, 2251, 2252, 2253, 2256, 2258, 2261, 2263, 2264, 2268, 2269, 2270, 2273, 2274, 2275, 2277, 2278, 2280, 2281, 2282, 2284, 2289, 2292, 2294, 2296, 2311, 2312, 2317, 2321 and 2324 of the C2 domain and the residues at positions 378, 383, 391, 398, 399, 400, 403, 406, 407, 408, 409, 410, 413, 414, 415, 416, 417, 421, 429, 432, 440, 442, 444, 445, 449, 452, 454, 455, 462, 464, 468, 481, 486, 490, 491, 493, 494, 496, 497, 498, 499, 500, 507, 512, 517, 518, 519, 520, 523, 524, 526, 530, 532, 534, 539, 540, 543, 550, 552, 556, 559, 562, 567, 568, 573, 578, 588, 592, 596, 597, 600, 601, 602, 604, 607, 611, 621, 624, 628, 629, 632, 633, 640 and 642 of the A2 domain. In a particular embodiment, the human FVIII variant or the biologically active derivative thereof further comprises a substitution of at least one amino acid selected from the group consisting of the residues at positions 2175, 2195, 2196, 2202, 2215 and 2222 of the C2 domain and the residues at positions 377, 379, 405, 434, 437, 485, 488, 489, 492, 495, 501, 508 and 623 of the A2 domain. In a particular embodiment, the human FVIII variant or the biologically active derivative thereof comprises the substitution of at least two, three, four, five, six, seven, eight, nine, ten, eleven, twelve, thirteen, fourteen or fifteen amino acids, preferably selected from the aforementioned groups.

In a preferred embodiment, the invention relates to an improved human FVIII variant or a biologically active derivative thereof having a decreased antigenicity and comprising the substitution of at least one amino acid selected from the group consisting of the residues at positions 2206, 2212, 2226, 2244, 2261, 2275, 2280, 2281, 2282, 2289, 2294, 2311, 2312, and 2316 of the C2 domain and the residues at positions 400, 403, 409, 414, 421, 462, 486, 493, 494, 496, 507, 518, 562, and 629 of the A2 domain. In another embodiment, said variant can further comprise a substitution of at least one amino acid selected from the group consisting of the residue at position 2202 of the C2 domain and the residue at position 437 of the A2 domain. The residue can be substituted by an amino acid selected from an Alanine, a Methionine, a Serine, a Glycine, and a Leucine, preferably an Alanine. In a particular embodiment, said human FVIII variant or biologically active derivative thereof has a single substitution. Said single substitution is preferably selected from the group consisting of the substitutions L400A, L400M, L400S, L400G, D403A, D403M, D403S, D403G, D403L, S409A, S409M, S409G, S409L, N414A, N414M, N414S, N414G, N414L, R421A, R421M, R421S, R421G, R421L, L462A, L462M, L462S, L462G, L486A, L486M, L486G, K493M, K493S, K493G, K493L, G494A, G494M, G494L, K496A, K496S, K496G, K496L, E507A, E507M, E507S, E507L, E518A, E518M, E518S, E518G, E518L, R562A, R562M, R562S, R562G, R562L, V629A, V629M, V629S, V629G and V629L in the A2 domain and the substitutions S2206A, S2206G, S2206M, S2206L, L2212A, L2212M, L2212S, L2212G, P2226A, P2226M, P2226S, P2226G, P2226L, T2244A, T2244M, T2244S, T2244G, T2244L, L2261A, L2261M, L2261S, L2261G, F2275A, F2275M, F2275S, F2275G, F2275L, V2280A, V2280M, V2280S, V2280G, V2280L, K2281A, K2281M, K2281S, K2281G, K2281L, V2282A, V2282M, V2282S, V2282G, V2282L, S2289A, S2289M, S2289G, S2289L, V2294A, V2294M, V2294S, V2294G, V2294L, Q2311A, Q2311M, Q2311S, Q2311G, Q2311L, S2312A, S2312M, S2312G, S2312L, Q2316A, Q2316M, Q2316S, Q2316G and Q2316L in the C2 domain. In another embodiment, the invention relates to a human FVIII variant or a biologically active derivative thereof comprising at least one substitution selected from the group consisting of the substitutions L400A, L400M, L400S, L400G, D403A, D403M, D403S, D403G, D403L, S409A, S409M, S409G, S409L, N414A, N414M, N414S, N414G, N414L, R421A, R421M, R421S, R421G, R421L, L462A, L462M, L462S, L462G, L486A, L486M, L486G, K493M, K493S, K493G, K493L, G494A, G494M, G494L, K496A, K496S, K496G, K496L, E507A, E507M, E507S, E507L, E518A, E518M, E518S, E518G, E518L, R562A, R562M, R562S, R562G, R562L, V629A, V629M, V629S, V629G and V629L in the A2 domain and the substitutions S2206A, S2206G, S2206M, S2206L, L2212A, L2212M, L2212S, L2212G, P2226A, P2226M, P2226S, P2226G, P2226L, T2244A, T2244M, T2244S, T2244G, T2244L, L2261A, L2261M, L2261S, L2261G, F2275A, F2275M, F2275S, F2275G, F2275L, V2280A, V2280M, V2280S, V2280G, V2280L, K2281A, K2281M, K2281S, K2281G, K2281L, V2282A, V2282M, V2282S, V2282G, V2282L, S2289A, S2289M, S2289G, S2289L, V2294A, V2294M, V2294S, V2294G, V2294L, Q2311A, Q2311M, Q2311S, Q2311G, Q2311L, S2312A, S2312M, S2312G, S2312L, Q2316A, Q2316M, Q2316S, Q2316G and Q2316L in the C2 domain. Said FVIII variants have lost one or more epitopes usually recognized by said antibodies and therefore have decreased antigenicity as compared to non-mutated human FVIII. Furthermore, they have retained at least 50%, preferably at least 60 or 75%, of raw activity relative to non-mutated human FVIII.

In a still more preferred embodiment, the invention relates to an improved human FVIII variant or a biologically active derivative thereof having a decreased antigenicity and having retained at least 100% of raw activity as compared to non-mutated human FVIII, and comprising the substitution of at least one amino acid selected from the group consisting of the residues at positions 409, 462, 507, and 629 of the A2 domain and the residues at positions 2289, 2294, 2312, and 2316 of the C2 domain. In another embodiment, said variant can further comprise a substitution of at least one amino acid selected from the group consisting of the residue at position 2202 of the C2 domain and the residue at position 437 of the A2 domain. The residue can be substituted by an amino acid selected from an Alanine, a Methionine, a Serine, a Glycine, and a Leucine, preferably an Alanine. In a particular embodiment, said human FVIII variant or biologically active derivative thereof has a single substitution. Said substitution is preferably selected from the group consisting of the substitutions S409A, S409M, S409G, S409L, L462A, L462M, L462S, L462G, E507A, E507M, E507S, E507L, V629A, V629M, V629S, V629G, V629L, S2289A, S2289M, S2289G, S2289L, V2294A, V2294M, V2294S, V2294G, V2294L, S2312A, S2312M, S2312G, S2312L, Q2316A, Q2316M, Q2316S, Q2316G and Q2316L. In another embodiment, the invention relates to a human FVIII variant or a biologically active derivative thereof comprising at least one substitution selected from the group consisting of the substitutions S409A, S409M, S409G, S409L, L462A, L462M, L462S, L462G, E507A, E507M, E507S, E507L, V629A, V629M, V629S, V629G, V629L, S2289A, S2289M, S2289G, S2289L, V2294A, V2294M, V2294S, V2294G, V2294L, S2312A, S2312M, S2312G, S2312L, Q2316A, Q2316M, Q2316S, Q2316G and Q2316L.

In a further embodiment, the invention relates to an improved human FVIII variant or a biologically active derivative thereof having a decreased antigenicity and comprising the combination of two substitutions selected from the group consisting of 409+462, 409+507, 462+507, 409+629, 462+629 and 507+629, preferably 409+462, 409+507 and 462+507. In a particular embodiment, said human FVIII variant or biologically active derivative thereof comprises the combination of two substitutions selected from the group consisting of S409A+L462A, S409A+L462M, S409A+L462S, S409A+L462G, S409A+E507A, S409A+E507M, S409A+E507S, S409A+E507G, S409A+E507L, S409A+V629A, S409A+V629M, S409A+V629S, S409A+V629G, S409A+V629L, S409M+L462A, S409M+L462M, S409M+L462S, S409M+L462G, S409M+E507A, S409M+E507M, S409M+E507S, S409M+E507G, S409M+E507L, S409M+V629A, S409M+V629M, S409M+V629S, S409M+V629G, S409M+V629L, S409G+L462A, S409G+L462M, S409G+L462S, S409G+L462G, S409G+E507A, S409G+E507M, S409G+E507S, S409G+E507G, S409G+E507L, S409G+V629A, S409G+V629M, S409G+V629S, S409G+V629G, S409G+V629L, S409L+L462A, S409L+L462M, S409L+L462S, S409L+L462G, S409L+E507A, S409L+E507M, S409L+E507S, S409L+E507G, S409L+E507L, S409L+V629A, S409L+V629M, S409L+V629S, S409L+V629G, S409L+V629L, L462A+E507A, L462A+E507M, L462A+E507S, L462A+E507G, L462A+E507L, L462A+V629A, L462A+V629M, L462A+V629S, L462A+V629G, L462A+V629L, L462M+E507A, L462M+E507M, L462M+E507S, L462M+E507G, L462M+E507L, L462M+V629A, L462M+V629M, L462M+V629S, L462M+V629G, L462M+V629L, L462S+E507A, L462S+E507M, L462S+E507S, L462S+E507G, L462S+E507L, L462S+V629A, L462S+V629M, L462S+V629S, L462S+V629G, L462S+V629L, L462G+E507A, L462G+E507M, L462G+E507S, L462G+E507G, L462G+E507L, L462G+V629A, L462G+V629M, L462G+V629S, L462G+V629G, L462G+V629L, E507A+V629A, E507A+V629M, E507A+V629S, E507A+V629G, E507A+V629L, E507M+V629A, E507M+V629M, E507M+V629S, E507M+V629G, E507M+V629L, E507S+V629A, E507S+V629M, E507S+V629S, E507S+V629G, E507S+V629L, E507G+V629A, E507G+V629M, E507G+V629S, E507G+V629G, E507G+V629L, E507L+V629A, E507L+V629M, E507L+V629S, E507L+V629G and E507L+V629L, preferably in the group consisting of S409A+L462A, S409A+L462M, S409A+L462S, S409A+L462G, S409A+E507A, S409A+E507M, S409A+E507S, S409A+E507G, S409A+E507L, S409M+L462A, S409M+L462M, S409M+L462S, S409M+L462G, S409M+E507A, S409M+E507M, S409M+E507S, S409M+E507G, S409M+E507L, S409G+L462A, S409G+L462M, S409G+L462S, S409G+L462G, S409G+E507A, S409G+E507M, S409G+E507S, S409G+E507G, S409G+E507L, S409L+L462A, S409L+L462M, S409L+L462S, S409L+L462G, S409L+E507A, S409L+E507M, S409L+E507S, S409L+E507G, S409L+E507L, L462A+E507A, L462A+E507M, L462A+E507S, L462A+E507G, L462A+E507L, L462M+E507A, L462M+E507M, L462M+E507S, L462M+E507G, L462M+E507L, L462S+E507A, L462S+E507M, L462S+E507S, L462S+E507G, L462S+E507L, L462G+E507A, L462G+E507M, L462G+E507S, L462G+E507G and L462G+E507L.

In yet another embodiment, the invention relates to an improved human FVIII variant or a biologically active derivative thereof comprising the combination of three substitutions selected from the group consisting of 409+462+507, 462+507+629, 409+462+629, 409+507+629, preferably 409+462+507. In a particular embodiment, said human FVIII variant or biologically active derivative thereof comprises the combination of three substitutions selected from the group consisting of S409A+L462A+E507A, S409A+L462A+E507M, S409A+L462A+E507S, S409A+L462A+E507G, S409A+L462A+E507L, S409A+L462M+E507A, S409A+L462M+E507M, S409A+L462M+E507S, S409A+L462M+E507G, S409A+L462M+E507L, S409A+L462S+E507A, S409A+L462S+E507M, S409A+L462S+E507S, S409A+L462S+E507G, S409A+L462S+E507L, S409A+L462G+E507A, S409A+L462G+E507M, S409A+L462G+E507S, S409A+L462G+E507G, S409A+L462G+E507L, S409M+L462A+E507A, S409M+L462A+E507M, S409M+L462A+E507S, S409M+L462A+E507G, S409M+L462A+E507L, S409M+L462M+E507A, S409M+L462M+E507M, S409M+L462M+E507S, S409M+L462M+E507G, S409M+L462M+E507L, S409M+L462S+E507A, S409M+L462S+E507M, S409M+L462S+E507S, S409M+L462S+E507G, S409M+L462S+E507L, S409M+L462G+E507A, S409M+L462G+E507M, S409M+L462G+E507S, S409M+L462G+E507G, S409M+L462G+E507L, S409G+L462A+E507A, S409G+L462A+E507M, S409G+L462A+E507S, S409G+L462A+E507G, S409G+L462A+E507L, S409G+L462M+E507A, S409G+L462M+E507M, S409G+L462M+E507S, S409G+L462M+E507G, S409G+L462M+E507L, S409G+L462S+E507A, S409G+L462S+E507M, S409G+L462S+E507S, S409G+L462S+E507G, S409G+L462S+E507L, S409G+L462G+E507A, S409G+L462G+E507M, S409G+L462G+E507S, S409G+L462G+E507G, S409G+L462G+E507L, S409L+L462A+E507A, S409L+L462A+E507M, S409L+L462A+E507S, S409L+L462A+E507G, S409L+L462A+E507L, S409L+L462M+E507A, S409L+L462M+E507M, S409L+L462M+E507S, S409L+L462M+E507G, S409L+L462M+E507L, S409L+L462S+E507A, S409L+L462S+E507M, S409L+L462S+E507S, S409L+L462S+E507G, S409L+L462S+E507L, S409L+L462G+E507A, S409L+L462G+E507M, S409L+L462G+E507S, S409L+L462G+E507G, S409L+L462G+E507L, S409A+L462A+V629A, S409A+L462A+V629M, S409A+L462A+V629S, S409A+L462A+V629G, S409A+L462A+V629L, S409A+L462M+V629A, S409A+L462M+V629M, S409A+L462M+V629S, S409A+L462M+V629G, S409A+L462M+V629L, S409A+L462S+V629A, S409A+L462S+V629M, S409A+L462S+V629S, S409A+L462S+V629G, S409A+L462S+V629L, S409A+L462G+V629A, S409A+L462G+V629M, S409A+L462G+V629S, S409A+L462G+V629G, S409A+L462G+V629L, S409M+L462A+V629A, S409M+L462A+V629M, S409M+L462A+V629S, S409M+L462A+V629G, S409M+L462A+V629L, S409M+L462M+V629A, S409M+L462M+V629M, S409M+L462M+V629S, S409M+L462M+V629G, S409M+L462M+V629L, S409M+L462S+V629A, S409M+L462S+V629M, S409M+L462S+V629S, S409M+L462S+V629G, S409M+L462S+V629L, S409M+L462G+V629A, S409M+L462G+V629M, S409M+L462G+V629S, S409M+L462G+V629G, S409M+L462G+V629L, S409G+L462A+V629A, S409G+L462A+V629M, S409G+L462A+V629S, S409G+L462A+V629G, S409G+L462A+V629L, S409G+L462M+V629A, S409G+L462M+V629M, S409G+L462M+V629S, S409G+L462M+V629G, S409G+L462M+V629L, S409G+L462S+V629A, S409G+L462S+V629M, S409G+L462S+V629S, S409G+L462S+V629G, S409G+L462S+V629L, S409G+L462G+V629A, S409G+L462G+V629M, S409G+L462G+V629S, S409G+L462G+V629G, S409G+L462G+V629L, S409L+L462A+V629A, S409L+L462A+V629M, S409L+L462A+V629S, S409L+L462A+V629G, S409L+L462A+V629L, S409L+L462M+V629A, S409L+L462M+V629M, S409L+L462M+V629S, S409L+L462M+V629G, S409L+L462M+

V629L, S409L+L462S+V629A, S409L+L462S+V629M, S409L+L462S+V629S, S409L+L462S+V629G, S409L+L462S+V629L, S409L+L462G+V629A, S409L+L462G+V629M, S409L+L462G+V629S, S409L+L462G+V629G, S409L+L462G+V629L, S409A+E507A+V629A, S409A+E507A+V629M, S409A+E507A+V629S, S409A+E507A+V629G, S409A+E507A+V629L, S409A+E507M+V629A, S409A+E507M+V629M, S409A+E507M+V629S, S409A+E507M+V629G, S409A+E507M+V629L, S409A+E507S+V629A, S409A+E507S+V629M, S409A+E507S+V629S, S409A+E507S+V629G, S409A+E507S+V629L, S409A+E507G+V629A, S409A+E507G+V629M, S409A+E507G+V629S, S409A+E507G+V629G, S409A+E507G+V629L, S409A+E507L+V629A, S409A+E507L+V629M, S409A+E507L+V629S, S409A+E507L+V629G, S409A+E507L+V629L, S409M+E507A+V629A, S409 M+E507A+V629M, S409M+E507A+V629S, S409M+E507A+V629G, S409M+E507A+V629L, S409M+E507M+V629A, S409M+E507M+V629M, S409M+E507M+V629S, S409M+E507M+V629G, S409M+E507M+V629L, S409M+E507S+V629A, S409M+E507S+V629M, S409M+E507S+V629S, S409M+E507S+V629G, S409M+E507S+V629L, S409M+E507G+V629A, S409M+E507G+V629M, S409M+E507G+V629S, S409M+E507G+V629G, S409M+E507G+V629L, S409M+E507L+V629A, S409M+E507L+V629M, S409M+E507L+V629S, S409M+E507L+V629G, S409M+E507L+V629L, S409G+E507A+V629A, S409G+E507A+V629M, S409G+E507A+V629S, S409G+E507A+V629G, S409G+E507A+V629L, S409G+E507M+V629A, S409G+E507M+V629M, S409G+E507M+V629S, S409G+E507M+V629G, S409G+E507M+V629L, S409G+E507S+V629A, S409G+E507S+V629M, S409G+E507S+V629S, S409G+E507S+V629G, S409G+E507S+V629L, S409G+E507G+V629A, S409G+E507G+V629M, S409G+E507G+V629S, S409G+E507G+V629G, S409G+E507G+V629L, S409G+E507L+V629A, S409G+E507L+V629M, S409G+E507L+V629S, S409G+E507L+V629G, S409G+E507L+V629L, S409L+E507A+V629A, S409L+E507A+V629M, S409L+E507A+V629S, S409L+E507A+V629G, S409L+E507A+V629L, S409L+E507M+V629A, S409L+E507M+V629M, S409L+E507M+V629S, S409L+E507M+V629G, S409L+E507M+V629L, S409L+E507S+V629A, S409L+E507S+V629M, S409L+E507S+V629S, S409L+E507S+V629G, S409L+E507S+V629L, S409L+E507G+V629A, S409L+E507G+V629M, S409L+E507G+V629S, S409L+E507G+V629G, S409L+E507G+V629L, S409L+E507L+V629A, S409L+E507L+V629M, S409L+E507L+V629S, S409L+E507L+V629G, S409L+E507L+V629L, L462A+E507A+V629A, L462A+E507A+V629M, L462A+E507A+V629S, L462A+E507A+V629G, L462A+E507A+V629L, L462A+E507M+V629A, L462A+E507M+V629M, L462A+E507M+V629S, L462A+E507M+V629G, L462A+E507M+V629L, L462A+E507S+V629A, L462A+E507S+V629M, L462A+E507S+V629S, L462A+E507S+V629G, L462A+E507S+V629L, L462A+E507G+V629A, L462A+E507G+V629M, L462A+E507G+V629S, L462A+E507G+V629G, L462A+E507G+V629L, L462A+E507L+V629A, L462A+E507L+V629M, L462A+E507L+V629S, L462A+E507L+V629G, L462A+E507L+V629L, L462M+E507A+V629A, L462M+E507A+V629M, L462M+E507A+V629S, L462M+E507A+V629G, L462M+E507A+V629L, L462M+E507M+V629A, L462M+E507M+V629M, L462M+E507M+V629S, L462M+E507M+V629G, L462M+E507M+V629L, L462M+E507S+V629A, L462M+E507S+V629M, L462M+E507S+V629S, L462M+E507S+V629G, L462M+E507S+V629L, L462M+E507G+V629A, L462M+E507G+V629M, L462M+E507G+V629S, L462M+E507G+V629G, L462M+E507G+V629L, L462M+E507L+V629A, L462M+E507L+V629M, L462M+E507L+V629S, L462M+E507L+V629G, L462M+E507L+V629L, L462S+E507A+V629A, L462S+E507A+V629M, L462S+E507A+V629S, L462S+E507A+V629G, L462S+E507A+V629L, L462S+E507M+V629A, L462S+E507M+V629M, L462S+E507M+V629S, L462S+E507M+V629G, L462S+E507M+V629L, L462S+E507S+V629A, L462S+E507S+V629M, L462S+E507S+V629S, L462S+E507S+V629G, L462S+E507S+V629L, L462S+E507G+V629A, L462S+E507G+V629M, L462S+E507G+V629S, L462S+E507G+V629G, L462S+E507G+V629L, L462S+E507L+V629A, L462S+E507L+V629M, L462S+E507L+V629S, L462S+E507L+V629G, L462S+E507L+V629L, L462G+E507A+V629A, L462G+E507A+V629M, L462G+E507A+V629S, L462G+E507A+V629G, L462G+E507A+V629L, L462G+E507M+V629A, L462G+E507M+V629M, L462G+E507M+V629S, L462G+E507M+V629G, L462G+E507M+V629L, L462G+E507S+V629A, L462G+E507S+V629M, L462G+E507S+V629S, L462G+E507S+V629G, L462G+E507S+V629L, L462G+E507G+V629A, L462G+E507G+V629M, L462G+E507G+V629S, L462G+E507G+V629G, L462G+E507G+V629L, L462G+E507L+V629A, L462G+E507L+V629M, L462G+E507L+V629S, L462G+E507L+V629G and L462G+E507L+V629L, preferably in the group consisting of S409A+L462A+E507A, S409A+L462A+E507M, S409A+L462A+E507S, S409A+L462A+E507G, S409A+L462A+E507L, S409A+L462M+E507A, S409A+L462M+E507M, S409A+L462M+E507S, S409A+L462M+E507G, S409A+L462M+E507L, S409A+L462S+E507A, S409A+L462S+E507M, S409A+L462S+E507S, S409A+L462S+E507G, S409A+L462S+E507L, S409A+L462G+E507A, S409A+L462G+E507M, S409A+L462G+E507S, S409A+L462G+E507G, S409A+L462G+E507L, S409M+L462A+E507A, S409M+L462A+E507M, S409M+L462A+E507S, S409M+L462A+E507G, S409M+L462A+E507L, S409M+L462M+E507A, S409M+L462M+E507M, S409M+L462M+E507S, S409M+L462M+E507G, S409M+L462M+E507L, S409M+L462S+E507A, S409M+L462S+E507M, S409M+L462S+E507S, S409M+L462S+E507G, S409M+L462S+E507L, S409M+L462G+E507A, S409M+L462G+E507M, S409M+L462G+E507S, S409M+L462G+E507G, S409M+L462G+E507L, S409G+L462A+E507A, S409G+L462A+E507M, S409G+L462A+E507S, S409G+L462A+E507G, S409G+L462A+E507L, S409G+L462M+E507A, S409G+L462M+E507M, S409G+L462M+E507S, S409G+L462M+E507G, S409G+L462M+E507L, S409G+L462S+E507A, S409G+L462S+E507M, S409G+L462S+E507S, S409G+L462S+E507G, S409G+L462S+E507L, S409G+L462G+E507A, S409G+L462G+E507M, S409G+L462G+E507S, S409G+L462G+E507G, S409G+L462G+E507L, S409L+L462A+E507A, S409L+L462A+E507M, S409L+L462A+E507S, S409L+L462A+E507G, S409L+L462A+E507L, S409L+L462M+E507A, S409L+L462M+E507M, S409L+L462M+E507S, S409L+L462M+E507G, S409L+L462M+E507L, S409L+L462S+E507A, S409L+L462S+E507M, S409L+L462S+E507S, S409L+L462S+E507G, S409L+L462S+E507L, S409L+L462G+E507A, S409L+L462G+E507M, S409L+L462G+E507S, S409L+L462G+E507G and S409L+L462G+E507L.

In another particular embodiment, the invention relates to an improved human FVIII variant or a biologically active derivative thereof comprising the combination of four substitutions at positions 409, 462, 507 and 629. In a particular embodiment, said human FVIII variant or biologically active derivative thereof comprises the combination of four substitutions selected from the group consisting of S409A+L462A+E507A+V629A, S409A+L462A+E507A+V629M, S409A+L462A+E507A+V629S, S409A+L462A+E507A+ V629G, S409A+L462A+E507A+V629L, S409A+L462A+ E507M+V629A, S409A+L462A+E507M+V629M, S409A+ L462A+E507M+V629S, S409A+L462A+E507M+V629G, S409A+L462A+E507M+V629L, S409A+L462A+E507S+ V629A, S409A+L462A+E507S+V629M, S409A+L462A+ E507S+V629S, S409A+L462A+E507S+V629G, S409A+ L462A+E507S+V629L, S409A+L462A+E507G+V629A, S409A+L462A+E507G+V629M, S409A+L462A+E507G+ V629S, S409A+L462A+E507G+V629G, S409A+L462A+ E507G+V629L, S409A+L462A+E507L+V629A, S409A+ L462A+E507L+V629M, S409A+L462A+E507L+V629S, S409A+L462A+E507L+V629G, S409A+L462A+E507L+ V629L, S409A+L462M+E507A+V629A, S409A+L462M+ E507A+V629M, S409A+L462M+E507A+V629S, S409A+ L462M+E507A+V629G, S409A+L462M+E507A+V629L, S409A+L462M+E507M+V629A, S409A+L462M+ E507M+V629M, S409A+L462M+E507M+V629S, S409A+ L462M+E507M+V629G, S409A+L462M+E507M+V629L, S409A+L462M+E507S+V629A, S409A+L462M+E507S+ V629M, S409A+L462M+E507S+V629S, S409A+L462M+ E507S+V629G, S409A+L462M+E507S+V629L, S409A+ L462M+E507G+V629A, S409A+L462M+E507G+V629M, S409A+L462M+E507G+V629S, S409A+L462M+E507G+ V629G, S409A+L462M+E507G+V629L, S409A+L462M+ E507L+V629A, S409A+L462M+E507L+V629M, S409A+ L462M+E507L+V629S, S409A+L462M+E507L+V629G, S409A+L462M+E507L+V629L, S409A+L462S+E507A+ V629A, S409A+L462S+E507A+V629M, S409A+L462S+ E507A+V629S, S409A+L462S+E507A+V629G, S409A+ L462S+E507A+V629L, S409A+L462S+E507M+V629A, S409A+L462S+E507M+V629M, S409A+L462S+E507M+ V629S, S409A+L462S+E507M+V629G, S409A+L462S+ E507M+V629L, S409A+L462S+E507S+V629A, S409A+ L462S+E507S+V629M, S409A+L462S+E507S+V629S, S409A+L462S+E507S+V629G, S409A+L462S+E507S+ V629L, S409A+L462S+E507G+V629A, S409A+L462S+ E507G+V629M, S409A+L462S+E507G+V629S, S409A+ L462S+E507G+V629G, S409A+L462S+E507G+V629L, S409A+L462S+E507L+V629A, S409A+L462S+E507L+ V629M, S409A+L462S+E507L+V629S, S409A+L462S+ E507L+V629G, S409A+L462S+E507L+V629L, S409A+ L462G+E507A+V629A, S409A+L462G+E507A+V629M, S409A+L462G+E507A+V629S, S409A+L462G+E507A+ V629G, S409A+L462G+E507A+V629L, S409A+L462G+ E507M+V629A, S409A+L462G+E507M+V629M, S409A+ L462G+E507M+V629S, S409A+L462G+E507M+V629G, S409A+L462G+E507M+V629L, S409A+L462G+E507S+ V629A, S409A+L462G+E507S+V629M, S409A+L462G+ E507S+V629S, S409A+L462G+E507S+V629G, S409A+ L462G+E507S+V629L, S409A+L462G+E507G+V629A, S409A+L462G+E507G+V629M, S409A+L462G+E507G+ V629S, S409A+L462G+E507G+V629G, S409A+L462G+ E507G+V629L, S409A+L462G+E507L+V629A, S409A+ L462G+E507L+V629M, S409A+L462G+E507L+V629S, S409A+L462G+E507L+V629G, S409A+L462G+E507L+ V629L, S409M+L462A+E507A+V629A, S409M+L462A+ E507A+V629M, S409M+L462A+E507A+V629S, S409M+ L462A+E507A+V629G, S409M+L462A+E507A+V629L, S409M+L462A+E507M+V629A, S409M+L462A+ E507M+V629M, S409M+L462A+E507M+V629S, S409M+L462A+E507M+V629G, S409M+L462A+ E507M+V629L, S409M+L462A+E507S+V629A, S409M+ L462A+E507S+V629M, S409M+L462A+E507S+V629S, S409M+L462A+E507S+V629G, S409M+L462A+E507S+ V629L, S409M+L462A+E507G+V629A, S409M+L462A+ E507G+V629M, S409M+L462A+E507G+V629S, S409M+ L462A+E507G+V629G, S409M+L462A+E507G+V629L, S409M+L462A+E507L+V629A, S409M+L462A+E507L+ V629M, S409M+L462A+E507L+V629S, S409M+L462A+ E507L+V629G, S409M+L462A+E507L+V629L, S409M+ L462M+E507A+V629A, S409M+L462M+E507A+ V629M, S409M+L462M+E507A+V629S, S409M+ L462M+E507A+V629G, S409M+L462M+E507A+V629L, S409M+L462M+E507M+V629A, S409M+L462M+ E507M+V629M, S409M+L462M+E507M+V629S, S409M+L462M+E507M+V629G, S409M+L462M+ E507M+V629L, S409M+L462M+E507S+V629A, S409M+ L462M+E507S+V629M, S409M+L462M+E507S+V629S, S409M+L462M+E507S+V629G, S409M+L462M+E507S+ V629L, S409M+L462M+E507G+V629A, S409M+ L462M+E507G+V629M, S409M+L462M+E507G+V629S, S409M+L462M+E507G+V629G, S409M+L462M+ E507G+V629L, S409M+L462M+E507L+V629A, S409M+ L462M+E507L+V629M, S409M+L462M+E507L+V629S, S409M+L462M+E507L+V629G, S409M+L462M+E507L+ V629L, S409M+L462S+E507A+V629A, S409 M+L462S+ E507A+V629M, S409M+L462S+E507A+V629S, S409M+ L462S+E507A+V629G, S409M+L462S+E507A+V629L, S409M+L462S+E507M+V629A, S409M+L462S+E507M+ V629M, S409M+L462S+E507M+V629S, S409M+L462S+ E507M+V629G, S409M+L462S+E507M+V629L, S409M+ L462S+E507S+V629A, S409M+L462S+E507S+V629M, S409M+L462S+E507S+V629S, S409M+L462S+E507S+ V629G, S409M+L462S+E507S+V629L, S409M+L462S+ E507G+V629A, S409M+L462S+E507G+V629M, S409M+ L462S+E507G+V629S, S409M+L462S+E507G+V629G, S409M+L462S+E507G+V629L, S409M+L462S+E507L+ V629A, S409M+L462S+E507L+V629M, S409M+L462S+ E507L+V629S, S409M+L462S+E507L+V629G, S409M+ L462S+E507L+V629L, S409M+L462G+E507A+V629A, S409M+L462G+E507A+V629M, S409M+L462G+ E507A+V629S, S409M+L462G+E507A+V629G, S409M+ L462G+E507A+V629L, S409M+L462G+E507M+V629A, S409M+L462G+E507M+V629M, S409M+L462G+ E507M+V629S, S409M+L462G+E507M+V629G, S409M+ L462G+E507M+V629L, S409M+L462G+E507S+V629A, S409M+L462G+E507S+V629M, S409M+L462G+E507S+ V629S, S409M+L462G+E507S+V629G, S409M+L462G+ E507S+V629L, S409M+L462G+E507G+V629A, S409M+ L462G+E507G+V629M, S409M+L462G+E507G+V629S, S409M+L462G+E507G+V629G, S409M+L462G+E507G+ V629L, S409M+L462G+E507L+V629A, S409M+L462G+ E507L+V629M, S409M+L462G+E507L+V629S, S409M+ L462G+E507L+V629G, S409M+L462G+E507L+V629L, S409G+L462A+E507A+V629A, S409G+L462A+E507A+ V629M, S409G+L462A+E507A+V629S, S409G+L462A+E507A+V629G, S409G+L462A+E507A+V629L, S409G+L462A+E507M+V629A, S409G+L462A+E507M+V629M, S409G+L462A+E507M+V629S, S409G+L462A+E507M+V629G, S409G+L462A+E507M+V629L, S409G+L462A+E507S+V629A, S409G+L462A+E507S+V629M, S409G+L462A+E507S+V629S, S409G+L462A+E507S+V629G, S409G+L462A+E507S+V629L, S409G+L462A+E507G+V629A, S409G+L462A+E507G+V629M, S409G+L462A+E507G+V629S, S409G+L462A+E507G+V629G, S409G+L462A+E507G+V629L, S409G+L462A+E507L+V629A, S409G+L462A+E507L+V629M, S409G+L462A+E507L+V629S, S409G+L462A+E507L+V629G, S409G+L462A+E507L+V629L, S409G+L462M+E507A+V629A, S409G+L462M+E507A+V629M, S409G+L462M+E507A+V629S, S409G+L462M+E507A+V629G, S409G+L462M+E507A+V629L, S409G+L462M+E507M+V629A, S409G+L462M+E507M+V629M, S409G+L462M+E507M+V629S, S409G+

L462M+E507M+V629G, S409G+L462M+E507M+V629L, S409G+L462M+E507S+V629A, S409G+L462M+E507S+V629M, S409G+L462M+E507S+V629S, S409G+L462M+E507S+V629G, S409G+L462M+E507S+V629L, S409G+L462M+E507G+V629A, S409G+L462M+E507G+V629M, S409G+L462M+E507G+V629S, S409G+L462M+E507G+V629G, S409G+L462M+E507G+V629L, S409G+L462M+E507L+V629A, S409G+L462M+E507L+V629M, S409G+L462M+E507L+V629S, S409G+L462M+E507L+V629G, S409G+L462M+E507L+V629L, S409G+L462S+E507A+V629A, S409G+L462S+E507A+V629M, S409G+L462S+E507A+V629S, S409G+L462S+E507A+V629G, S409G+L462S+E507A+V629L, S409G+L462S+E507M+V629A, S409G+L462S+E507M+V629M, S409G+L462S+E507M+V629S, S409G+L462S+E507M+V629G, S409G+L462S+E507M+V629L, S409G+L462S+E507S+V629A, S409G+L462S+E507S+V629M, S409G+L462S+E507S+V629S, S409G+L462S+E507S+V629G, S409G+L462S+E507S+V629L, S409G+L462S+E507G+V629A, S409G+L462S+E507G+V629M, S409G+L462S+E507G+V629S, S409G+L462S+E507G+V629G, S409G+L462S+E507G+V629L, S409G+L462S+E507L+V629A, S409G+L462S+E507L+V629M, S409G+L462S+E507L+V629S, S409G+L462S+E507L+V629G, S409G+L462S+E507L+V629L, S409G+L462G+E507A+V629A, S409G+L462G+E507A+V629M, S409G+L462G+E507A+V629S, S409G+L462G+E507A+V629G, S409G+L462G+E507A+V629L, S409G+L462G+E507M+V629A, S409G+L462G+E507M+V629M, S409G+L462G+E507M+V629S, S409G+L462G+E507M+V629G, S409G+L462G+E507M+V629L, S409G+L462G+E507S+V629A, S409G+L462G+E507S+V629M, S409G+L462G+E507S+V629S, S409G+L462G+E507S+V629G, S409G+L462G+E507S+V629L, S409G+L462G+E507G+V629A, S409G+L462G+E507G+V629M, S409G+L462G+E507G+V629S, S409G+L462G+E507G+V629G, S409G+L462G+E507G+V629L, S409G+L462G+E507L+V629A, S409G+L462G+E507L+V629M, S409G+L462G+E507L+V629S, S409G+L462G+E507L+V629G, S409G+L462G+E507L+V629L, S409L+L462A+E507A+V629A, S409L+L462A+E507A+V629M, S409L+L462A+E507A+V629S, S409L+L462A+E507A+V629G, S409L+L462A+E507A+V629L, S409L+L462A+E507M+V629A, S409L+L462A+E507M+V629M, S409L+L462A+E507M+V629S, S409L+L462A+E507M+V629G, S409L+L462A+E507M+V629L, S409L+L462A+E507S+V629A, S409L+L462A+E507S+V629M, S409L+L462A+E507S+V629S, S409L+L462A+E507S+V629G, S409L+L462A+E507S+V629L, S409L+L462A+E507G+V629A, S409L+L462A+E507G+V629M, S409L+L462A+E507G+V629S, S409L+L462A+E507G+V629G, S409L+L462A+E507G+V629L, S409L+L462A+E507L+V629A, S409L+L462A+E507L+V629M, S409L+L462A+E507L+V629S, S409L+L462A+E507L+V629G, S409L+L462A+E507L+V629L, S409L+L462M+E507A+V629A, S409L+L462M+E507A+V629M, S409L+L462M+E507A+V629S, S409L+L462M+E507A+V629G, S409L+L462M+E507A+V629L, S409L+L462M+E507M+V629A, S409L+L462M+E507M+V629M, S409L+L462M+E507M+V629S, S409L+L462M+E507M+V629G, S409L+L462M+E507M+V629L, S409L+L462M+E507S+V629A, S409L+L462M+E507S+V629M, S409L+L462M+E507S+V629S, S409L+L462M+E507S+V629G, S409L+L462M+E507S+V629L, S409L+L462M+E507G+V629A, S409L+L462M+E507G+V629M, S409L+L462M+E507G+V629S, S409L+L462M+E507G+V629G, S409L+L462M+E507G+V629L, S409L+L462M+E507L+V629A, S409L+L462M+E507L+V629M, S409L+L462M+E507L+V629S, S409L+L462M+E507L+V629G, S409L+L462M+E507L+V629L, S409L+L462S+E507A+V629A, S409L+L462S+E507A+V629M, S409L+L462S+E507A+V629S, S409L+L462S+E507A+V629G, S409L+L462S+E507A+V629L, S409L+L462S+E507M+V629A, S409L+L462S+E507M+V629M, S409L+L462S+E507M+V629S, S409L+L462S+E507M+V629G, S409L+L462S+E507M+V629L, S409L+L462S+E507S+V629A, S409L+L462S+E507S+V629M, S409L+L462S+E507S+V629S, S409L+L462S+E507S+V629G, S409L+L462S+E507S+V629L, S409L+L462S+E507G+V629A, S409L+L462S+E507G+V629M, S409L+L462S+E507G+V629S, S409L+L462S+E507G+V629G, S409L+L462S+E507G+V629L, S409L+L462S+E507L+V629A, S409L+L462S+E507L+V629M, S409L+L462S+E507L+V629S, S409L+L462S+E507L+V629G, S409L+L462S+E507L+V629L, S409L+L462G+E507A+V629A, S409L+L462G+E507A+V629M, S409L+L462G+E507A+V629S, S409L+L462G+E507A+V629G, S409L+L462G+E507A+V629L, S409L+L462G+E507M+V629A, S409L+L462G+E507M+V629M, S409L+L462G+E507M+V629S, S409L+L462G+E507M+V629G, S409L+L462G+E507M+V629L, S409L+L462G+E507S+V629A, S409L+L462G+E507S+V629M, S409L+L462G+E507S+V629S, S409L+L462G+E507S+V629G, S409L+L462G+E507S+V629L, S409L+L462G+E507G+V629A, S409L+L462G+E507G+V629M, S409L+L462G+E507G+V629S, S409L+L462G+E507G+V629G, S409L+L462G+E507G+V629L, S409L+L462G+E507L+V629A, S409L+L462G+E507L+V629M, S409L+L462G+E507L+V629S, S409L+L462G+E507L+V629G, S409L+L462G+E507L+V629L.

In a further preferred embodiment, the invention relates to an improved human FVIII variant or a biologically active derivative thereof having an improved specific activity and comprising the substitution of at least one amino acid selected from the group consisting of the residues at positions 2177, 2183, 2186, 2191, 2204, 2205, 2206, 2213, 2217, 2235, 2258, 2264, 2268 and 2269 of the C2 domain. Said variant can further comprise the substitution of the amino acid at position 2196 of the C2 domain. Moreover, said mutations which confer a higher specific activity may prove to be of great interest in combination with mutations conferring abolition to inhibition by inhibitory antibodies, by allowing, for example, to compensate an optional relative loss of activity of said less antigenic mutants. Thus, in a particular embodiment, the invention relates to an improved human FVIII variant or a biologically active derivative thereof comprising the substitution of at least one amino acid selected from the group consisting of the residues at positions 400, 403, 409, 414, 421, 462, 486, 493, 494, 496, 507, 518, 562, and 629 of the A2 domain and the residues at positions 2206, 2212, 2226, 2244, 2261, 2275, 2280, 2281, 2282, 2289, 2294, 2311, 2312, and 2316 of the C2 domain, and further comprising a substitution of at least one amino acid selected from the group consisting of the residues at positions 2177, 2183, 2186, 2191, 2204, 2205, 2213, 2217, 2235, 2258, 2264, 2268 and 2269 of the C2 domain. Preferably, said variant comprises the substitution of at least one amino acid selected from the group consisting of the residues at positions 409, 462, 507 and 629 of the A2 domain and the residues at positions 2289, 2294, 2312 and 2316 of the C2 domain, and further comprises a substitution of at least one amino acid selected from the group consisting of the residues at positions 2177, 2183, 2186, 2191, 2204, 2205, 2213, 2217, 2235, 2258, 2264, 2268 and 2269 of C2 the domain.

In an additional preferred embodiment, the invention relates to an improved human FVIII variant or a biologically active derivative thereof having an improved capacity to be secreted and comprising the substitution of at least one amino acid selected from the group consisting of the residues at positions 2199, 2200, 2215, 2251, 2252, 2278, and 2316 of the C2 domain. Said variant can further comprise the substitution of the amino acid at position 2175 of the C2 domain. Furthermore, said mutations which confer higher capacity to be secreted may prove to be of great interest in combination with mutations conferring abolition to inhibition by inhibitory antibodies, by allowing, for example, to compensate an optional relative loss of secretion of said less antigenic mutants. Thus, in a particular embodiment, the invention relates to an improved human FVIII variant or a biologically active derivative thereof comprising the substitution of at least one amino acid selected from the group consisting of the residues at positions 400, 403, 409, 414, 421, 462, 486, 493, 494, 496, 507, 518, 562, and 629 of the A2 domain and the residues at positions 2206, 2212, 2226, 2244, 2261, 2275, 2280, 2281, 2282, 2289, 2294, 2311, 2312, and 2316 of the C2 domain, and further comprising a substitution of at least one amino acid selected from the group consisting of the residues at positions 2175, 2199, 2200, 2215, 2251, 2252 and 2278 of the C2 domain. In a preferred manner, said variant comprises the substitution of at least one amino acid selected from the group consisting of the residues at positions 409, 462, 507 and 629 of the A2 domain and the residues at positions 2289, 2294, 2312 and 2316 of the C2 domain, and further comprises a substitution of at least one amino acid selected from the group consisting of the residues at positions 2175, 2199, 2200, 2215, 2251, 2252 and 2278 of the C2 domain.

The broad production of mutants having retained at least 50% of FVIII activity also makes it possible to encompass their use in the context of analyzing additional functions of the protein. In addition to a modulation of its immunogenicity, secretion and specific activity, the following FVIII properties might be improved by using the mutants molecules described: —binding to von Willebrand factor and therefore improved half-life of FVIII or circulating FVIIIa; —improved intrinsic stability of the molecule by stabilization of the A2 domain and therefore increase of its efficiency period; —binding to phospholipids derived from blood platelets, cell surfaces or circulating microparticles and therefore improved generation of FXa; —binding to FIXa and FX and therefore improved formation of FXa; —decreased binding of FVIII or FVIIIa to the molecules responsible of its catabolism such as for example low density Lipoprotein Receptor-related Protein (LRP), Low Density Lipoprotein Receptor (LDLR), Very Low Density Lipoprotein Receptor (VLDLR), megaline or any other receptor which might be identified and therefore improvement of the circulating FVIII half-life of; —decreased proteolysis of FVIII or FVIIIa by vascular proteases such as for example activated protein C, FXa, FIXa, and therefore increased of its efficiency period.

Preferably, the biologically active FVIII derivative is a FVIII consisting in a whole or partial deletion of the B domain. The human FVIII variant of the present invention is not a hybrid FVIII. It does not contain a substitution of the A2 or C2 domain or of a segment of at least 15 consecutive amino acids thereof by a FVIII domain of another species. In particular, segments of the A2 domain 373-540, 373-508, 445-508, 484-508, 404-508, 489-508 and/or 484-489 are not substituted by those of another species. In a particular embodiment, the polypeptide sequence of the variant differs from that of human FVIII such as described in SEQ ID No. 3 by 1, 2, 3, 4, 5, 6, 7, 8, 9, 10, 11, 12, 13, 14 or 15 substitutions, preferably by 1, 2, 3, 4, 5, 6, 7 or 8 substitutions, without including an optional deletion or truncation. In a particular embodiment, the variant comprises a single substitution. In another particular embodiment, the variant comprises a combination of 1 to 8 substitutions selected from a group according to the present invention.

"Inhibitory antibodies" or "inhibitors" refers to any antibody which recognizes or binds to FVIII and inhibits the biological activity thereof, in particular the procoagulant activity thereof. In particular, said antibodies can preferably recognize i) the C2 domain of the light chain (2181-2321); ii) the A2 domain of the heavy chain (484-509); or iii) the A3 domain (1694-2019). Examples of commercially available inhibitory antibodies comprise ESH-8 (strong inhibitor; recognized the region 2248/2285; 6300 BU/mg; anti-C2; America Diagnostica), GMA-8015 (anti-A2; Green Mountain), anti-C2 ESH-4 antibody (strong inhibitor; region 2303/2332; America Diagnostica), anti-C2 Bo2C11 antibody (Jacquemin et al., 1998, Blood, 92(2):496-506).

"Patients with inhibitors" are patients who have FVIII inhibitory antibodies in their serum. The recognition profile of said antibodies differs from a patient to another. An improved FVIII according to the present invention is a FVIII which at least partially avoids one or more types of inhibitory antibodies.

"Biologically active derivative of FVIII" refers to any protein or peptide derived from human FVIII which retains a procoagulant activity of FVIII. For example, such biologically active FVIII derivative may be a FVIII whose B domain (741-1648) has been partially or totally deleted (Toole et al., 1986, Proc. Natl. Acad. Sci. USA, 83 (16):5939-5942; Pittman, 1993, Blood, 81:2925-2935; Eaton et al., 1986, Biochemistry, 25 (26):8343-8347; Langer et al., 1988, Behring Inst. Mitt, 82:16-25; Meulien et al., 1988, Protein Eng, 2(4): 301-6; and U.S. Pat. No. 4,868,112). Moreover, this term also refers to FVIII mutants with a stabilized A2 domain (WO 97/40145), FVIII mutants allowing a higher expression (Swaroop et al., 1997, JBC, 272:24121-24124), FVIII mutants having decreased antigenicity (Lollar, 1999, Thromb. Haemost. 82:505-508), a FVIII reconstituted from separately expressed light and heavy chains (Oh et al., 1999, Exp. Mol. Med. 31:95-100), FVIII mutants displaying decreased binding to FVIII catabolic associated receptors such as HSPG (heparan sulfate proteoglycans) and LRP (low density lipoprotein receptor related protein) (Ananyeva et al., 2001, TCM, 11:251-257), FVIII mutants displaying an improved specific activity (US2004/0249134). Also considered are FVIII variants in which FVIII segments are replaced by the corresponding segments of factor V (Marquette et al., 1995, JBC, 270:10297-10303, Oertel et al., 1996, Thromb. Haemost., 75:36-44). Moreover, said term refers to any FVIII comprising one or more substitutions, deletions or insertions. For example, it comprises the variants described in the introduction of the present application, in particular those comprising point mutations. In particular, it comprises a FVIII less susceptible to cleavage by APC (activated protein C) comprising mutations of Arginines 336 and 562 and in the region comprised between the positions 2001-2020, as described in application WO 2006/027111. It further comprises a stabilized FVIII mutant in which one or more Cysteines have been introduced so as to create one or more disulfide bonds, for example between the A2 and A3 domains (WO02103024; Gale et Pellequer, 2003, J Thromb Haemost, 1(9):1966-71). Patents JP2005112855 and RU2244556/RU2253475 respectively provide biologically stable and albumin-free compositions, allowing the stabilization of FVIII alone or in association with vWF. This term also refers to any FVIII having been modified by conjugation of a functional group, for example PEGylation, glycosylation (for example US2005009148, US2003077752, etc.). Furthermore, the variant can comprise peptide bonds modified in order to resist to hydrolysis.

In particular, the variant has a decreased antigenicity towards inhibitory antibodies as compared to natural human FVIII and retains a procoagulant activity at least equal to 50% that of natural human FVIII. For example, one suitable assay is the one or two-stage clotting assay described in Rizza et al. (Rizza et al., 1982, Coagulation assay of Factor VIIIa and FIXa in Bloom ed. The Hemophilias. NY Churchchill Livingston 1992). In a preferred embodiment, the variant retains a procoagulant activity equal to that of natural human FVIII. In a more preferred embodiment, the variant has a procoagulant activity higher than that of natural human FVIII.

The procoagulant activity of FVIII is determined by any method known to one skilled in the art. Preferably, said procoagulant activity is determined by chronometric assay or by chromogenic assay. Even more preferably, FVIII activity is determined by chronometric assay, for example as described by Von Clauss (A. Acta Haematologica, 1957, 17:237) or by chronometric assay such as described by Rosen (Scand. J. Haematol. 1984, 33 (Suppl 40):139-145).

The present invention relates to a nucleic acid coding for a human FVIII variant according to the invention. The present invention also relates to an expression cassette of a nucleic acid according to the invention. It further relates to a vector comprising a nucleic acid or an expression cassette according to the invention. The vector can be selected from a plasmid and a viral vector.

The nucleic acid can be DNA (cDNA or gDNA), RNA, or a mixture of the two. It can be in single stranded form or in duplex form or a mixture of the two. It can comprise modified nucleotides, comprising for example a modified bond, a modified purine or pyrimidine base, or a modified sugar. It can be prepared by any method known to one skilled in the art, including chemical synthesis, recombination, mutagenesis etc.

The expression cassette comprises all elements required for expression of the human FVIII variant according to the invention, in particular the elements required for transcription and translation in the host cell. The host cell can be prokaryotic or eukaryotic. In particular, the expression cassette comprises a promoter and a terminator, optionally an enhancer. The promoter can be prokaryotic or eukaryotic. Examples of preferred prokaryotic promoters include: LacI, LacZ, pLacT, ptac, pARA, pBAD, the RNA polymerase promoters of bacteriophage T3 or T7, the polyhedrin promoter, the PR or PL promoter of lambda phage. Examples of preferred eukaryotic promoters include: CMV early promoter, HSV thymidine kinase promoter, SV40 early or late promoter, mouse metallothionein-L promoter, and the LTR regions of some retroviruses. In general, to select a suitable promoter, one skilled in the art may advantageously consult Sambrook et al. work (1989) or techniques described by Fuller et al. (1996; Immunology in Current Protocols in Molecular Biology).

The present invention relates to a vector containing a nucleic acid or an expression cassette coding for a human FVIII variant according to the invention. The vector is preferably an expression vector, that is to say, it comprises the elements required for the expression of the variant in the host cell. The host cell can be a prokaryote, for example E. coli, or a eukaryote. The eukaryote can be a lower eukaryote such as a yeast (for example, S. cerevisiae) or fungus (for example from the genus Aspergillus) or a higher eukaryote such as an insect, mammalian or plant cell. The cell can be a mammalian cell, for example COS, CHO (U.S. Pat. Nos. 4,889,803 ; 5,047,335). In a particular embodiment, the cell is non-human and non-embryonic. The vector can be a plasmid, phage, phagemid, cosmid, virus, YAC, BAC, pTi plasmid from Agrobacterium, etc. The vector can preferably comprise one or more elements selected from the group consisting of a replication origin, a multiple cloning site and a selection gene. In a preferred embodiment, the vector is a plasmid. Examples of prokaryotic vectors include, but are not limited to, the following: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pBR322, and pRIT5 (Pharmacia), pET (Novagen). Examples of eukaryotic vectors include, but are not limited to, the following: pWLNEO, pSV2CAT, pPICZ, pcDNA3.1 (+) Hyg (Invitrogen), pOG44, pXT1, pSG (Stratagene); pSVK3, pBPV, pCI-neo (Stratagene), pMSG, pSVL (Pharmacia); and pQE-30 (QLAexpress). Examples of viral vectors include, but are not limited to, adenoviruses, AAV, HSV, lentiviruses, etc. Preferably the expression vector is a plasmid or a viral vector.

The coding sequence for FVIII according to the present invention can comprise or not comprise the signal peptide. In the case where coding sequence does not comprise signal peptide, a methionine can optionally be added at the N-terminal end. Alternatively, a heterologous signal peptide can be introduced. Said heterologous signal peptide can be derived from a prokaryote such as E. coli or from a eukaryote, in particular from a mammalian, insect or yeast cell. Moreover, the nucleotide sequence can also comprise intron segments, particularly heterologous introns. Said intron segments can enable improved expression of the FVIII variant. Such constructs are described in application WO 2005/040213. For example, the nucleotide sequence can comprise modified sequence SEQ ID No. 5 so as to code for the FVIII variant comprising the substitution or substitutions according to the present invention.

The present invention relates to the use of a nucleic acid, an expression cassette or a vector according to the invention in order to transform or transfect a cell. The invention relates to a host cell comprising a nucleic acid, an expression cassette or a vector coding for a human FVIII variant and the use thereof to produce a recombinant human FVIII variant according to the invention. In a particular embodiment, the cell is non-human and non-embryonic. The invention also relates to a method for producing a recombinant human FVIII variant according to the invention comprising transforming or transfecting a cell by a nucleic acid, an expression cassette or a vector according to the invention; culturing the transformed/transfected cell; and collecting the human FVIII variant produced by the cell. In an alternative embodiment, the method for producing a recombinant human FVIII variant according to the invention comprises providing a cell comprising a nucleic acid, an expression cassette or a vector according to the invention; culturing the transfected/transformed cell; and collecting the human FVIII variant produced by the cell. In particular, the cell can be transformed/transfected in a transient or stable manner by the nucleic acid coding for the variant. Said nucleic acid can be contained in the cell in an episome form of or in chromosomal form. Method for producing recombinant proteins are well known to one skilled in the art. For example, one can mention the specific method described in WO01/70968 for a production in an immortalized human cell line, WO2005/123928 for production in a plant, US2005/229261 for production in the milk of a transgenic animal, etc.

The present invention relates to pharmaceutical compositions comprising human FVIII variants according to the invention, and to the use of said FVIII variants for preparing a medicament for the treatment of hemophilia A. Preferably, the hemophilia A is severe and moderate. Said treatment can be curative or preventive. In a particular embodiment, the treated patients are patients with inhibitors.

Thus, the FVIII variants according to the invention can be used in two major categories of hemophiliac patients: those who have developed FVIII inhibitory antibodies, thanks to their capacity to avoid said inhibitory antibodies, and those who have not yet developed such inhibitors, thanks to their lower risk of inducing the development of inhibitory antibodies as compared to the molecules currently used. Said FVIII variants will be usable by all patients with hemophilia A.

The present invention therefore relates to a pharmaceutical composition comprising a FVIII variant according to the invention. The pharmaceutical composition can further comprise compounds for stabilizing the mutant FVIII, for example serum albumin, vWF (von Willebrand factor) or a fragment thereof comprising the FVIII binding site, vitamin K-dependent coagulation factors, and polysaccharides such as sucrose. The present invention can also relate to a pharmaceutical composition comprising a nucleic acid coding for a FVIII mutant according to the invention, a vector or a host cell according to the invention. Such composition might be useful in the context of a gene therapy. The pharmaceutical composition can further comprise a pharmaceutically acceptable excipient or carrier. Such excipients and carriers are well known to one skilled in the art [Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)] and comprise physiological saline solutions and phosphate buffers. The FVIII variant according to the invention can also be formulated in a pharmaceutical composition with phospholipids or equivalents, for example in the form of liposomes, nanoparticles, etc. (WO2004/071420; WO2004/091723). The pharmaceutical composition can further comprise one or more other active ingredients.

The present invention also relates to a FVIII variant according to the invention as medicament. It further relates to a nucleic acid coding for a FVIII mutant, an expression cassette, a vector or a host cell according to the invention, as medicament.

The human FVIII variants of the invention can be used as replacement therapy in case of severe and moderate hemophilia A. The possibility of a continuously use with a lower risk of developing inhibitory antibodies is a major advantage over the different existing recombinant human or hybrid FVIIIs.

Said improved human FVIII variants are preferably intended for treating patients who have already developed inhibitors, but also for preventive treatment.

In addition, systematic administration of said FVIII might be encompass for a prophylactic treatment in any patient with hemophilia A. One might therefore imagine decreasing the risks of bleeding, for example during surgical procedures, or else preventing the development of inhibitors. The administration of said FVIII might also be considered in the case of an emergency treatment, for example during an accidental, pathological hemorrhage or caused by a surgical procedure.

The pharmaceutical compositions of the invention are suitable for oral, sublingual, subcutaneous, intramuscular, intravenous, topical, local, intratracheal, intranasal, transdermal, rectal, intraocular, intra-auricular administration, said active ingredient being able to be administered as a unit dose. Preferably, the pharmaceutical compositions are suitable for intravenous, subcutaneous or intramuscular administration.

The dosages of the treatment can differ according to the severity of FVIII deficiency. Usually, the dosage is adjusted for frequency, period and units related to the severity and length of the bleeding episodes of the considered patient. FVIII is dosed so as to arrest bleeding, for example with standard clotting assays. An efficient dose of FVIII variant according to the invention can comprise, but is not limited to, between about 5 to 50 units per kg of body weight, preferably between 10 to 50, even more preferably between 20 to 40. The dosing frequency can be for example every 8 to 24 hours. The treatment duration can be for example from 1 to 10 days, or until bleeding stops. [See for example: Roberts, H. R., and M. R. Jones, "Hemophilia and Related Conditions—Congenital Deficiencies of Prothrombin (Factor II, Factor V, and Factors VII to XII), "Ch. 153, 1453-1474,1460, in Hematology, Williams, W. J. et al., ed. (1990)].

The treatment can be in the form of a single intravenous injection or periodic or continuous administration over an extended period of time, as necessary. The treatment can also be administered by the subcutaneous or oral route with liposomes in one or more doses at different time intervals.

The present invention relates to the use of a human FVIII variant or a biologically active derivative thereof according to the invention for preparing a medicament for the treatment of coagulation disorders, in particular hemophilia A. The treatment can be curative or preventive. In a particular embodiment, the patient to be treated is a patient with inhibitors. The present invention also relates to a method for treating hemophilia A comprising administering a human FVIII variant or a biologically active derivative thereof according to the invention.

The present invention further relates to the use of a nucleic acid coding for a FVIII variant according to the invention for preparing a medicament for the treatment of coagulation disorders, in particular hemophilia A.

The FVIII variant of the invention can also be combined with another active compound. For example, the present invention also relates to the use of a FVIII variant according to the invention in combination with factor IXa for treating coagulation disorders, and in particular hemophilia A or B. Said combination is described in WO2004/103397.

The present invention further relates to the use of one or more human FVIII variants or a biologically active derivative thereof according to the invention for the diagnosis of inhibitor type in a patient with hemophilia A. In particular, the presence of inhibitory antibodies is assayed in serum samples or biological fluids (lymph, urine, etc.). Detection of inhibitory antibodies can be carried out by ELISA, immunodetection by electrophoretic blotting, radioimmunoassay, and FVIII activity assays (for example, clotting assay).

In fact, inventors have identified in wild-type human FVIII the positions specifically recognized by the inhibitors. Said positions can be used individually, combined within a same domain, or combined between the A2 and C2 domains, so as to reveal the type(s) of inhibitory antibodies present in a hemophiliac. In fact, the need to diagnose inhibitory antibodies is crucial. The titration of said inhibitors is a prerequisite prior to any replacement therapy. The inventors therefore propose to use of the present findings to diagnose inhibitory antibodies. A Bethesda assay (assay of inhibitor titer) in a hemophiliac patient can be carried out before and after passage on ELISA where the capture antigen corresponds to the FVIII variants of the present invention taken separately or combined. The inhibitor titer will significantly decrease for the control carried out with wild-type FVIII. The variant or variants combination for which the inhibitor titer remains unchanged is used as treatment for the hemophiliac patient with inhibitors. This diagnosis therefore renders possible to control and target the delivery of the human FVIII variant according to the invention.

Thus, the present invention relates to a method for treatment comprising:

a recognition test of inhibitory antibodies contained in a serum sample of patient on one or more FVIII variants according to the invention;

selection of the FVIII mutant or mutants which are not recognized by said inhibitory antibodies; and administration of one or more FVIII mutants selected from b).

In a preferred manner, the recognition test between the patient's sample and the FVIII variant(s) according to the invention is carried out by a Bethesda assay. As a control, a recognition test is preferably carried out on wild-type FVIII.

The present invention relates to a diagnostic kit comprising one or more FVIII variants according to the invention.

The present invention also relates to the use of one or more human FVIII variants or a biologically active derivative thereof according to the invention for preparing a medicament for the treatment of hemophilia A in patients with inhibitors whose serum does not contain antibodies recognizing said human FVIII variant(s) or a biologically active derivative thereof.

All references cited herein are included by reference in the present application. Other features and advantages of the invention will become apparent in the following examples which are provided for purposes of illustration and not by way of limitation.

EXAMPLES

Example 1

Molecular Biology

FVIII complementary DNA containing two truncated introns of factor IX at position 1 and 13 (5012 bp) (SEQ ID No. 4) was cloned between the NotI and Xho1 restriction sites in a vector (pcDNA3.1 GS, Invitrogen) allowing expression of the protein in mammalian cells. The pcDNA/FVIII construct corresponded to a 10,439 bp plasmid. This gene comprises the five functional domains A1, A2, A3, C1 and C2 essential for FVIII activity. As it has previously been shown that the B domain does not play any predominant role in the procoagulant function of FVIII, the inventors chose to produce FVIII with a deletion of this domain. The regions coding for the A1 and A2 domains each contain an intron. Insertion of these two intron regions among the coding exons significantly improves the expression of human FVIII. The protein sequence encoded by this gene is given in SEQ ID No. 5.

The mutagenesis strategy consisted in systematically generating all the single Alanine mutants in the targeted domains of FVIII, i.e., A2, A3 and C2. Said mutants were generated by the Massive Mutagenesis® method described in US2004/0048268.

As mentioned earlier, it has been shown that domains A2, C2 and A3 are the preferential targets of FVIII recognition by inhibitory antibodies. Each amino acid in these functional domains was substituted by an Alanine, apart from the intron segment of the A2 domain. A series of 795 oligonucleotides (32-mers) was designed and produced so as to introduce an Alanine mutation at positions i) 376 to 719 [A2]; ii) 2173 to 2325 [C2]; iii) 1691 to 2025 [A3]. The numbering system for the mutations of human FVIII used in the invention is that defined by Wood et al. (Nature, 1984, 312:330-337). After site-directed mutagenesis, the inventors performed two successive sequencings to check that each mutant of the library contained the Alanine mutation at the considered position. This collection of Alanine mutants in the C2, A2 and A3 domains of FVIII is the first comprehensive site-directed mutants library ever carried out for this molecule.

Example 2

Expression of Human FVIII Alanine Mutants in COS-7 Mammalian Cells

FVIII is usually expressed in mammalian cells (Toole et al., 1984, Nature, 312:342-347; Gitschier et al., 1984, Nature, 312:326-330; Wood et al., 1984, Nature, 312:330-337; Vehar et al., 1984, Nature, 312:337-342; WO8704187; WO 8808035; WO8803558; U.S. Pat. No. 4,757,006).

In order to transfect COS-7 cells with the native or mutated pcDNA/FVIII constructs, said cells were trypsinized when they reached 90% confluence. The COS-7 cells were reseeded at a 1/4 ratio (that is, in order to obtain approximately 25% confluence once they adhered to the surface). Transient transfection of COS-7 cells was carried out in 90 mm culture plates (6 ml per well) when cells reached 70-80% confluence. Transfection was carried out with approximately 6 μg DNA for a volume of 18 μl FuGENE-6 (Roche, Meylan, France).

Prior to transfection, FuGENE-6 was diluted in serum-free IMDM medium and incubated at room temperature for 5 min. The FuGENE-6/DNA mixture was left at room temperature for 15 min then deposited dropwise on the cells in complete medium. A first supernatant containing FVIII was collected 24 h after transfection; 6 ml of fresh medium were then placed on the cells. The culture supernatant was collected 48 h later (6 ml), aliquoted and stored at −20° C. pending the clotting assay (chromogenic). The mean level of expression of wild-type FVIII was estimated by ELISA (Stago commercial ELISA kit) and was comprised between 20 and 60 ng/ml.

All cell culture reagents were from Invitrogen. COS-7 cells (African green monkey SV40 transformed kidney cells) were grown in standard culture conditions (37° C. in a humid 5% $CO_2$ atmosphere) using Iscove's Modified Dulbecco's Medium (IMDM). IMDM was supplemented with an L-glutamine analog (glutamax), decomplemented fetal calf serum (10% final concentration) and antibiotics (penicillin 40 U/ml and streptomycin 0.1 mg/ml).

Example 3

Primary Screen: Functional Analysis of Human FVIII Alanine Mutants

The primary screen correlates to raw coagulant activity determination (FIG. 1) obtained in a same volume of COS-7 cell culture supernatant. Two different assays of clotting activity determination were used in the primary screen, the chronometric assay and the chromogenic assay.

Chronometric activity was measured following incubation of a dilution of the FVIII molecules to be tested in imidazole buffer in the presence of FVIII-deficient plasma (Stago). Clotting was initiated by addition of calcium and the time to clot formation was determined on a MDA-II apparatus (BioMérieux, Marcy-l'Etoile). The coagulant activity of the 795 Alanine mutants was measured by chronometric assay on a robotic platform of the National Hemophilia Treatment Center (Hospices Civils de Lyon). The chronometric activity of all the Alanine mutants was compared to the activity of a wild-type FVIII used as internal standard for each transfection. Results of these determinations of raw activity relative to that of non-mutated FVIII distinguished two categories of mutants: I) mutants having retained at least 50% of wild-type FVIII activity; ii) mutants having less than 50% of wild-type FVIII activity. FIG. 2 shows the coagulant activity of 359 over 795 Alanine mutants analyzed. These data represent a functional mapping of each of these FVIII residues for coagulant activity; a coagulant activity suppressed by an Alanine mutation indicates that the considered residue is essential for FVIII coagulant activity.

158 mutants having retained more than 50% of raw non-mutated FVIII activity were selected by this chronometric assay for secondary screen. Their activities were first confirmed by the second clotting assay, the chromogenic assay mentioned above. This assay was also performed on the robotic platform of the National Hemophilia Treatment Center (Hospices Civils de Lyon). The chromogenic activity of the 158 selected Alanine mutants was carried out with the Coamatic Factor VIII kit (Chromogenix, Instrumentation Laboratory, Milan, Italy) according to the supplier's instructions. Briefly, culture supernatants (50 µl) were diluted in the dilution buffer provided and preincubated at 37° C. for 4 min. The reaction medium (50 µl), preheated at 37° C., was then added for 4 min, after which 50 µl of development medium at 37° C. were added. The formation of product over time was measured immediately on a spectrophotometer at 405 nm after shaking the microtiter plate. Product formation is expressed as mUOD/min. When values were greater than 200 mUOD/min, the assay was repeated using a higher dilution.

Table 1 shows the activities of the 158 mutants which retained more than 50% of non-mutated FVIII activity. Said 158 mutants were selected for the secondary screening.

Example 4

Secondary Screen: Evaluation of Loss of Antigenicity Towards Human FVIII Inhibitory Antibodies The secondary screen correlates to an assay similar to the Bethesda assay, carried out as described below on the 158 mutants selected following the primary screening; said assay comprises a step of contacting a inhibitory serum (or antibody) with a FVIII molecule to be tested or a reference standard and a step of measuring FVIII coagulant activity by chronometric assay.

Culture supernatants obtained after 48 h of contact with COS cells transfected by different FVIII constructs were used. Said supernatants were produced in complete medium [(IMDM, Invitrogen), 10% fetal calf serum, 2 mM L-glutamine, 100 U/ml penicillin, 100 mg/ml streptomycin]. Supernatants were diluted in fresh complete medium to obtain a final chronometric activity comprised in the range of about 10-20% (1 FVIII unit=100% activity=200 ng/ml). The culture supernatant diluted or not (140 μl) was added to 150 μl of FVIII-depleted human plasma (Stago, Asnières, France). An antibody dilution (10 μl) was then added to the mix. These antibodies are IgG fractions purified on protein A—from hemophiliac patients with inhibitors. An IgG fraction from a non-hemophiliac control was similarly obtained. Bethesda inhibitor titers were identical to the inhibitory activity from the plasma. The purification protocol therefore did not affect the inhibitory activity of the antibodies. The antibodies were first diluted in fresh complete medium, the measurement being carried out either with a fixed antibody dilution or with serial dilutions. The fixed antibody concentration which was used was that which produced 50% inhibition of a recombinant FVIII standard solution with 12.5% activity. Samples were incubated in a 37° C. water-bath for 1 h 30. Coagulant activity was then determined on a MDA-II apparatus (BioMérieux, Marcy-I'Etoile) and compared to that of a standard curve established from an identical FVIII stably produced in the CHO cell line. Results are expressed as a percentage which represents the abolition to inhibition of coagulant activity of a given mutant by inhibitory antibodies from a patient's serum. Said percentage was calculated as shown in FIG. 5 for the FVIII mutant E518A. Abolition to inhibition expressed is a percentage=−[(b−a)/a]×100; where "a" is the percentage residual activity of the WT (serum+IgG/serum−IgG) and "b" is the percentage residual activity of the mutant (serum+IgG/serum−IgG).

Table 2 shows for 30 single mutants the percentages of abolition to inhibition for sera from five hemophiliac patients. Said mutants were selected in the secondary screen of the 158 mutants selected in the primary screen. Several mutants show a high percentage of abolition to inhibition with certain sera, such as mutant 2316 for sera TD and SL, mutant 2294 for serum GC, mutant 403 for serum FS and mutant 2275 for serum PR.

Patients' sera were selected for their high Bethesda titers (greater than 10 BU) and their different inhibitor profiles. These patients can no longer be treated with FVIII injections and need bypassing agents. Thus, obtaining FVIII Alanine mutants which abolish, even partially, the inhibition of FVIII activity by the inhibitory antibodies of one of these patients, is a major step forward to the future approaches of treating hemophiliac patients with inhibitors. The different data obtained on a large number of mutants as well as the different sera tested will make it possible to create combinations of mutations leading to an improved FVIII which can avoid a majority of inhibitory antibodies while retaining its procoagulant activity.

The reproducibility of FVIII expression level related to transfections was controlled by following the specific activity of wild-type FVIII. Indeed, specific activities calculated from antigen determinations (Stago commercial ELISA kit) were identical for wild-type FVIIIs produced in different transfections. Likewise, antigen concentrations were determined for mutants having retained at least 50% of wild-type FVIII activity and their specific activity was determinate throw. Specific activity corresponds to raw activity measured in the chromogenic assay (mUOD/min) relative to protein concentration (ng/ml) obtained with an ELISA kit (Stago FVIII kit). Table 3 shows comparative data of raw and specific activities of 30 mutants selected in the secondary screen.

The eight FVIII Alanine mutants 2175, 2199, 2200, 2215, 2251, 2252, 2278 and 2316 displayed a far above average capacity to be secreted in the COS cell production medium used in the scope of the present invention. FIG. 3 depicts the data obtained for these eight mutants. Raw coagulant activity of these mutants was determined by chromogenic assay. Their concentration was approximately two to four times higher than that of wild-type FVIII. This property is interesting for producing recombinant FVIII and might make it possible to lower production costs of a new generation FVIII. Also, it might be advantageous in a gene therapy for hemophiliac patients. Moreover, these mutations which confer a greater capacity to be secreted may be of major interest in combination with mutations conferring abolition to inhibition by inhibitory antibodies, by allowing, for example, to compensate an optional relative loss of secretion of said less antigenic mutants.

Figure 8A:
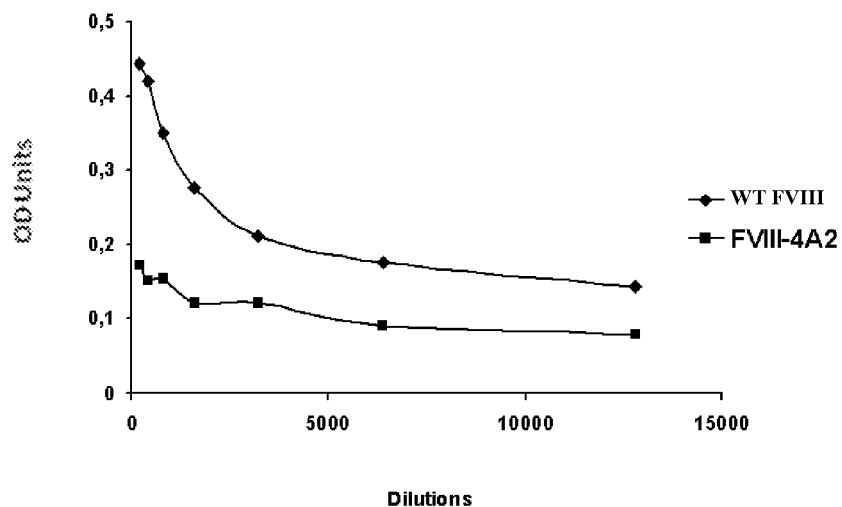
Figure 8B:
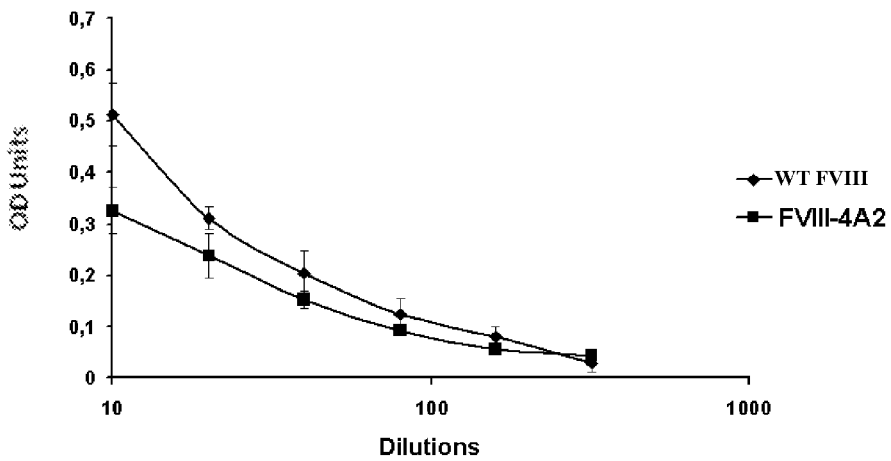

The 15 mutants 2177, 2183, 2186, 2191, 2196, 2204, 2205, 2206, 2213, 2217, 2235, 2258, 2264, 2268 and 2269 displayed far higher specific activity than wild-type FVIII, while maintaining a high production level, around to that of wild-type FVIII (concentration greater than 10 ng/ml). The specific activities of these 15 mutants are given in FIG. 4. Raw coagulant activity of these mutants was determined by chromogenic assay. This property is interesting because it would allow smaller or less frequent doses of FVIII to be injected in patients. Moreover, these mutations which confer a higher specific activity might be of major interest in combination with mutations conferring abolition to inhibition by inhibitory antibodies, by allowing to compensate an optional relative loss of activity of said less antigenic mutants.

Example 5

Selection and Combination of the Best Single Mutants Selected in the Secondary Screen Among the 30 single mutants selected in the secondary screen, eight were chosen in order to combine their respective mutations, to obtain a cumulative/additive effect of remarkable properties of each. The selection criteria for these mutants were complex and considered the following parameters:

- at least 25% abolition to inhibition for at least one of the test sera from hemophiliac patients with inhibitors;
- raw coagulant activity at least 100% relative to non-mutated FVIII; and
- reproducibly good level of expression.

The eight selected mutants were mutants 409, 462, 507 and 629 in the A2 domain and mutants 2289, 2294, 2312 and 2316 in the C2 domain. As noted earlier, the selection criterion considered of a high specific activity (coagulant activity relative to expression level), as shown in Table 3. This specific activity level had to be constant in the different experiments.

The 28 double mutants resulting from the combination of the eight single mutations 409, 462, 507, 629, 2289, 2294, 2312 and 2316 (six A2 double mutants+six C2 double mutants+sixteen A2-C2 double mutants presented in Table 4) were constructed by mutagenesis methods known to one skilled in the art. These mutants were transiently expressed in COS-7 mammalian cells as described in Example 2. Their expression level and their activity level were determined as described in the previous examples, respectively by ELISA and chromogenic assay (mUOD/min). These 28 mutants were then assessed for their abolition to inhibition by antibodies from hemophiliac patients. The A2 double mutants displayed a significant abolition to inhibition for one or all of the antibodies from the patients' sera, whereas the combinations containing C2 domain mutations (six C2 double mutants+sixteen A2-C2 double mutants) displayed an insignificant or null abolition to inhibition.

Table 5 shows the specific activities of the six A2 double mutants and their percentage of abolition to inhibition by sera from four hemophiliac patients TD, GC, SL and PR calculated as in Example 4. Especially preferred double mutants significantly abolished antibodies from a minimum of three over the four patients. This illustrates the cumulative effect of the four single mutations in the A2 domain. The choice was therefore based on the combination of the four mutations 409, 507, 462 and 629. Triple mutants and the quadruple mutant comprising these four mutations 409, 507, 462 and 629 were also constructed.

Example 6

Construction and Characterization of a Quadruple Mutant (FVIII-4A2)

The quadruple mutant derived from the combination of the four selected A2 mutations 409, 462, 507, 629 was constructed by a classical mutagenesis method known to one skilled in the art. The quadruple mutant was produced in a CHO cell line obtained as described in Example 9. This mutant was also characterized for its abolition to inhibition by antibodies from five hemophiliac patients FS, TD, GC, PR and SL. Residual activity determined after incubation with an inhibitory antibody is divided by residual activity remaining after incubation with a non-immune antibody. The percentage of residual activity was thus determined and is presented in the graphs of FIG. 6. These graphs illustrate the residual activity of FVIII-4A2 after contact with different dilutions of antibodies from the different patients with inhibitors. It clearly appears that the FVIII-4A2 mutant retained a much higher chronometric activity after incubation with the inhibitory antibodies. Accordingly, the increases in residual activity for the highest inhibitory antibodies concentrations ranged from 230 to 450%, said percentage of residual activity depending on both the source of the inhibitory antibody and the concentration used.

To determine whether direct binding of the antibodies to FVIII-4A2 was modified, three additional antibodies were used instead of the patients' sera according to the same protocol as above: an anti-A2 domain antibody (GMA012, Green Mountain Antibodies), an anti-C2 domain antibody (ESH4, American Diagnostica) and a rabbit polyclonal antibody, purified from the same protocol used for the patients' antibodies. The results of these controls are shown in FIG. 7 for the two anti-A2 domain antibodies, the rabbit polyclonal antibody and GMA012. Clearly, the mutations in the A2 domain of FVIII-4A2 allowed FVIII-4A2 to avoid the anti-A2 domain antibody, GMA012 and the rabbit polyclonal antibody (shown). On the other hand, no significant differences in inhibition of FVIII-4A2 versus wild-type FVIII were seen for ESH4 (data not shown). These findings correlate the abolition to inhibition data, showing on one hand that introduction of mutations in the A2 domain allow to avoid patients' antibodies and on the other hand that the C2 domain of FVIII-4A2 is undamaged since recognition is similar to that of wild-type FVIII. This latter point is important for FVIII-4A2 activity because it is the C2 domain which is responsible for interactions with von Willebrand factor and with the cofactors required for full FVIII activity (calcium and phospholipid binding).

Example 7

Characterization of the FVIII 4A2 Mutant a) ELISA

FVIII-4A2 was produced in the same CHO cell line as wild-type FVIII according to the protocol described in Example 9. It was purified by the same protocol (also described in Example 9) and was therefore compared to FVIII in functional analyses. FVIII-4A2 concentrations were determined with an ELISA kit (see protocol below). Additional controls were performed using a panel of monoclonal antibodies to check that the introduced mutations did not alter the quantification of mutant FVIII with this kit. Thereby, it was shown that similar concentrations of wild-type FVIII and FVIII-4A2 were identically recognized by antibody ESH-4 directed against the light chain C2 domain. In agreement with the abolition to inhibition data, there was a large decrease in recognition of FVIII-4A2 by the GMA012 antibody in comparison with wild-type FVIII. These data are presented in FIG. 8.

The protocol of the ELISA assays for these experiments is described below:

Reagent was diluted at least five-fold in 50 mM CAPS pH 9.0 and incubated overnight at 4° C. to coat the interest product on the support of the ELISA plate (Nunc Maxisorb). Wells were then washed twice with TBS-T buffer (50 mM Tris-HCl pH 8.0, 100 mM NaCl, 5 mM $MgCl_2$, 0.01% Tween 20, 0.05% BSA), then blocked for 1 h with TBS-3% BSA (50 mM Tris-HCl pH 8.0, 100 mM NaCl, 5 mM $MgCl_2$, 0.01% Tween-20, 3% BSA). Reagent binding with the one coated on the plate was then diluted in TBS-3% BSA, incubated at room temperature for 1 h 30, then washed three times in TBS-T. Primary and secondary antibodies conjugated to horse radish peroxidase (HRP) were diluted in TBS-3% and respectively added for 1 h 30 at room temperature. Secondary antibodies were diluted 2000-fold. Between two antibody incubations, plates were washed three times with TBS-T, then washed again before addition of the substrate, a mixture of OPD/urea (Sigma). The enzymatic reaction was stopped by adding 2.5M $H_2SO_4$. Optical density was read at 490 nm.

b) Measurement of Specific Activity

Specific activity of the FVIII-4A2 mutant was determined by dividing chromogenic activity by concentration. These specific activities were compared with those of the wild-type. The chromogenic activity of wild-type FVIII was about 15±1 ODU/min·µg and that of FVIII-4A2 was about 27±1 ODU/min·µg, that is, a higher activity.

c) Activation by Thrombin

Wild-type FVIII and FVIII-4A2 (0.125 U or 25 ng) were diluted in 40 mM HEPES buffer, 100 mM NaCl, 5 mM $CaCl_2$ containing 10 µM of an 80:20 mixture of Phosphatidylcholine:Phosphatidylserine and 0.1 mg/ml BSA, then incubated at 37° C. for 5 min. Thrombin (0.05 U) was added and its action determined at different time. At each time, an aliquot was removed and incubated with a mixture of hirudin (0.5 U), factor IXa (50 nM) and factor X (200 nM) diluted in the same buffer, in order to generate FXa. The FXa substrate pNAPEP-25 was immediately added and formation of the chromogenic product was measured at 405 nm. The initial rate was determined and the amount of FXa formed per minute was calculated.

Figure 9:
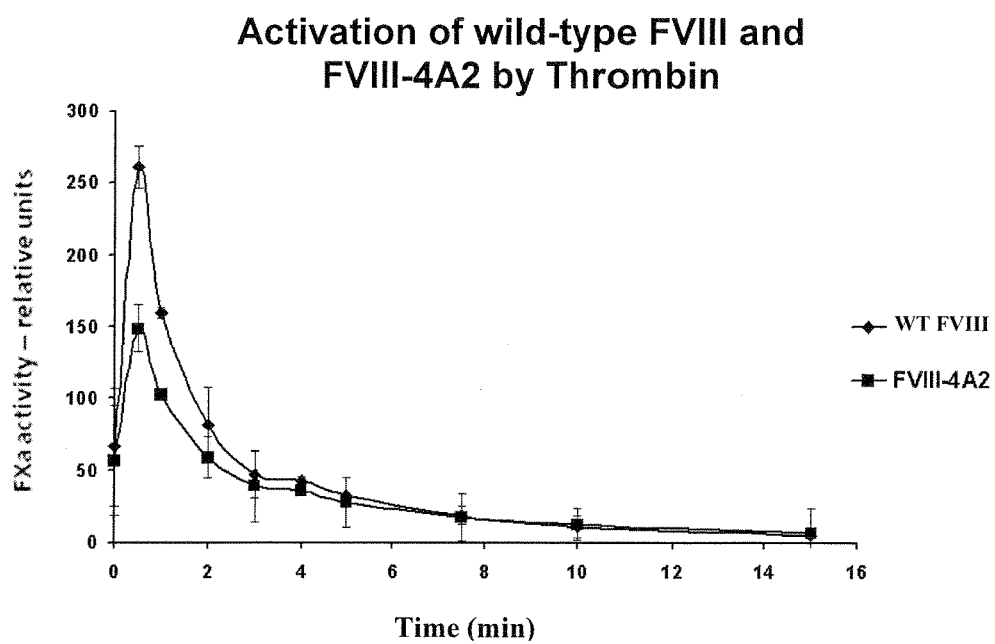

Wild-type FVIII and FVIII-4A2 displayed an identical thrombin response profile, with a rapid increase in FVIII activity, reaching the peak at 1-2 min after addition of thrombin, followed by a rapid decrease of said activity with a half-life of approximately 2-3 min. The results shown in FIG. 9 indicate that FVIII-4A2 is identically recognized by thrombin as wild-type FVIII with a relative decrease of activity which might be caused by one of the four mutations.

d) Dissociation of the A2 Domain

Wild-type FVIII and FVIII-4A2 were activated as described above for 1 min. Hirudin was then added and FVIIIa was left at 37° C. for different time periods. Aliquots were removed at said time and incubated with a mixture of phospholipids, FIXa and FX. FXa was allowed to form for 5 min, then Stop buffer was added (Tris 50 mM pH 8.8, 475 mM NaCl, 9 mM EDTA). The amount of FXa formed was determined as above.

Figure 10:
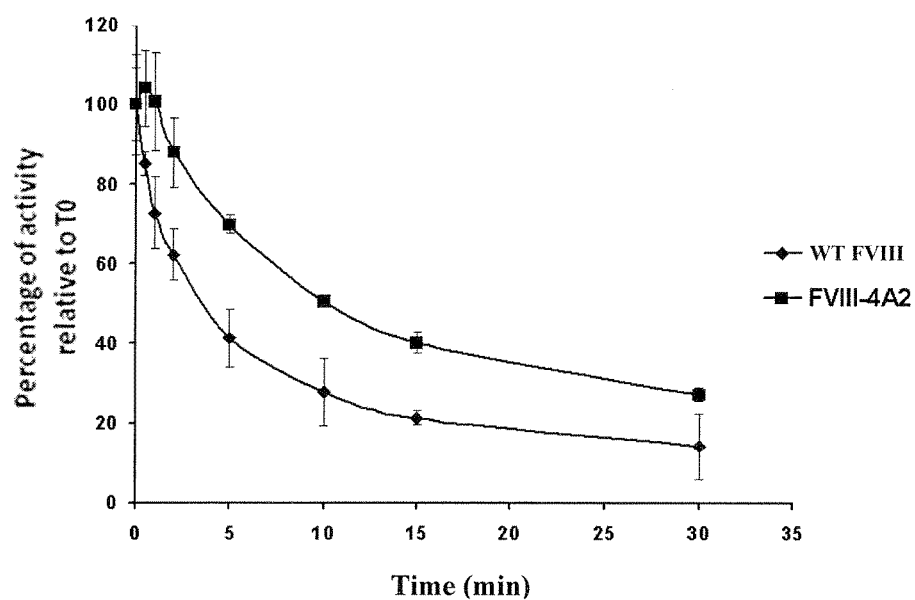
Figure 11A:
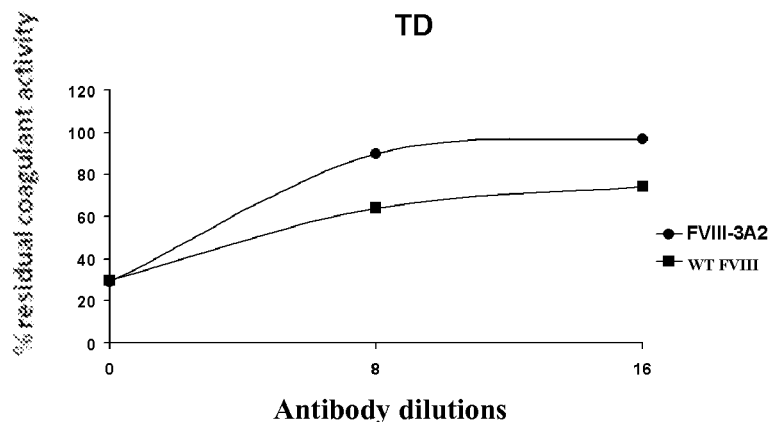
Figure 11B:
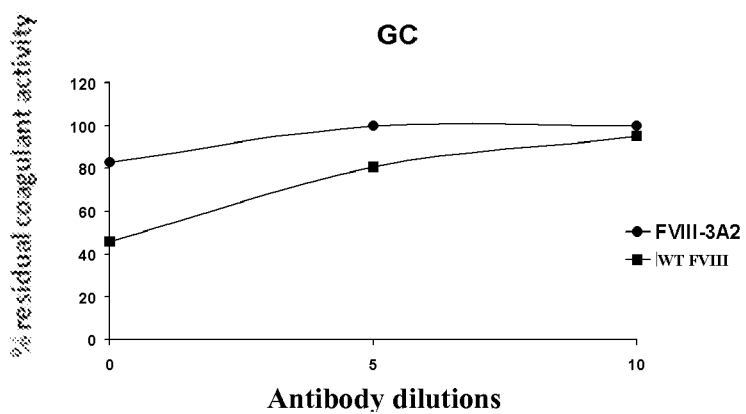
Figure 11C:
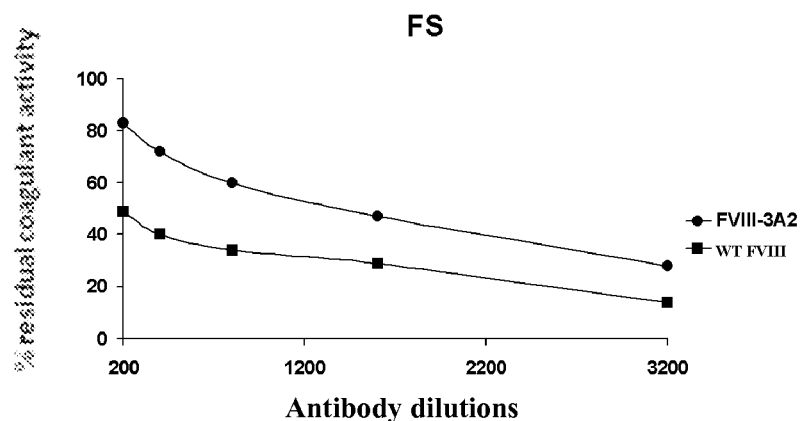
Figure 11D:
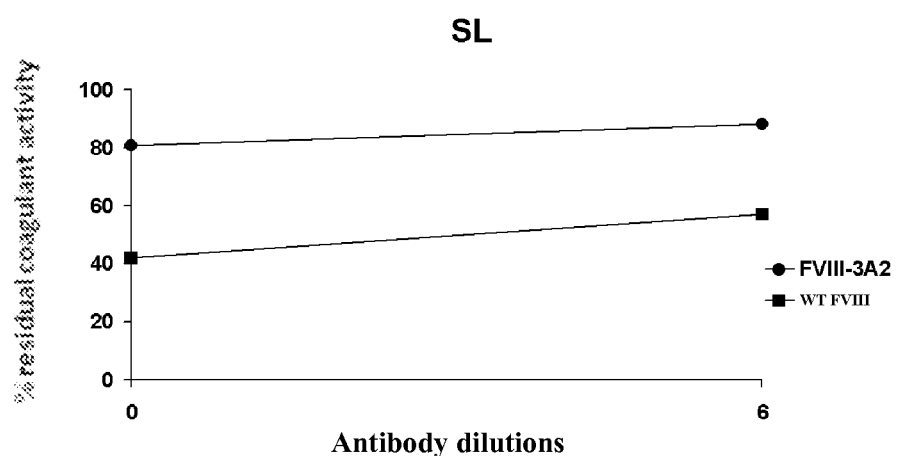

FVIIIa was incubated for different times before determining its residual activity. The loss of activity over time corresponds to dissociation of the A2 domain. The loss of activity profile of wild-type FVIII and FVIII-4A2 was similar but the respective kinetics differed. Indeed, wild-type FVIII had a half-life of 3 min while that of FVIII-4A2 was 11 min. This increased stability may explain the higher specific activity observed in the chromogenic assay. In this test, FVIIIa was incubated for 4 min before adding the substrate. Wild-type FVIII thus lost its activity faster than FVIII-4A2 during this test. The results are shown in FIG. 10.

Example 8

Construction and Characterization of FVIII-3A2 Mutants

Four triple FVIII-3A2 mutants were constructed: FVIII-3A2 (409-462-507), FVIII-3A2 (462-507-629), FVIII-3A2 (409-462-629), FVIII-3A2 (409-507-629).

FVIII-3A2 (409-462-507) Specific Activity Determination

The specific activity of the FVIII-3A2 mutant (409-462-507) was determined by dividing chromogenic or chromogenic activity by concentration. These specific activities were compared with that of wild-type FVIII. The chromogenic activity of FVIII-3A2 (409-462-507) was 98% of the chromogenic activity of wild-type FVIII. These results indicate that the absence of mutation at position 629 in FVIII-3A2 yielded a higher coagulant activity than for FVIII-4A2.

FVIII-3A2 (409-462-507) Abolition to Inhibition

This mutant was also analyzed for its abolition to inhibition by antibodies from the four hemophiliac patients FS, TD, GC and SL. Residual activity determined after incubation with an inhibitory antibody was divided by the activity remaining after incubation with a non-immune antibody. The percentage of residual activity was thus determined and is presented in FIG. 11 curves. These curves illustrate the residual activity of FVIII-3A2 (409-462-507) after contact with different dilutions of antibodies from the different patients with inhibitors. It clearly appears that the use of the FVIII-3A2 mutant (409-462-507) enable to retain a much higher chronometric activity after incubation with inhibitory antibodies. The combination of mutations 409-462-507 therefore yields a greater abolition to inhibition resulting in an increase in residual activity. This percentage of residual activity depends on both the source of inhibitory antibody and the concentration used.

Example 9

Production of a CHO Cell Line Expressing FVIII-4A2 and Purification/ Production of FVIII Production of the CHO Cell Line A CHO cell line (ECACC 85050302) expressing FVIII was generated as described in Plantier et al. (Thrombosis and Haemostasis 2001; 86 p. 596). Briefly, cells were maintained at 37° C. in a humid 5% $CO_2$ atmosphere. Cells were grown in IMDM medium supplemented with 10% fetal calf serum and 1% penicillin-streptomycin. Cells ($7 \times 10^6$) were trypsinized and resuspended in PBS, then subjected to electroporation in presence of a cDNA of interest (7 µg). Cells were then reseeded in the presence of geneticin (0.6 mg/ml). Individual clones were selected, subcultured and amplified. Cells' ability to synthesize FVIII was determined by measuring the chromogenic activity of the culture medium. The best producer clones were amplified and grown in triple flasks. Production took place over 5 days during which cells were incubated in complete medium during the day, washed three times, then incubated overnight in IMDM medium containing 1% BSA instead of serum. The BSA-containing medium was collected, centrifuged at 2500 rpm for 10 min at 4° C. and stored at −30° C. Cells were put back into complete medium during the day.

Purification and Production of FVIII Mutants (FVIII-3A2 and FVIII-4A2)

The purification protocol was based on the technique described by Jenkins et al. (Blood, 2004). The culture medium was thawed and 40% (m/V) $(NH_4)_2SO_4$ was added. The medium was shaken overnight at 4° C., then centrifuged at 14,000 rpm for 30 min at 4° C. The pellet was resuspended 1 in 10 by volume in 20 mM MES pH 6.0, 100 mM NaCl, 5 mM $CaCl_2$, 0.01% Tween-20 buffer and dialyzed overnight against a similar buffer but containing 200 mM NaCl. Dialysate was centrifuged at 13,000 rpm for 10 min at room temperature, then loaded at 2 ml/min on a FLPC Sepharose FF column. The column was previously equilibrated with the same buffer. FVIII was eluted in a 0.2 to 1 M NaCl gradient. Fractions containing the highest chromogenic activity were pooled and dialyzed against 50 mM HEPES pH 7.4, 100 mM NaCl, 5 mM NaCl and 0.01% Tween-20 buffer. Dialysate was aliquoted and stored at −80° C. The quality of the protein was assessed after migration on SDS-PAGE 10% acrylamide by silver nitrate staining and by immunoblot. FVIII concentration was determined by the Asserachrom FVIII:Ag kit (Stago, Asnieres, France).

The invention claimed is:

1. An isolated human coagulation factor VIII (FVIII) variant comprising a substitution of the amino acid at position 462 of SEQ ID NO: 3, wherein said variant has decreased antigenicity towards inhibitory antibodies as compared to natural human FVIII, retains procoagulant activity and, optionally, totally or partially lacks the domain B, and wherein the polypeptide sequence of the variant differs from SEQ ID NO: 3 by 1, 2, 3, 4, 5, 6, 7, 8, 9, 10, 11, 12, 13, 14 or 15 substitutions, without including the optional total or partial deletion of the domain B.

2. The isolated human coagulation FVIII variant according to claim 1, wherein said variant comprises a single amino acid substitution.

3. The isolated human coagulation FVIII variant according to claim 1, wherein said variant further comprises a substitution of at least one amino acid selected from the group consisting of the amino acids at position 2202 and 437 of SEQ ID NO: 3.

4. The isolated human coagulation FVIII variant according to claim 1, wherein said variant contains a combination of two substitutions selected from the group consisting of the amino acids at positions 409+462, 462+507 and, 462+629 of SEQ ID NO: 3.

5. The isolated human coagulation FVIII variant according to claim 1, wherein said variant contains a combination of three substitutions selected from the group consisting of the amino acids at positions 409+462+507, 462+507+629, and 409+462+629 of SEQ ID NO: 3.

6. The isolated human coagulation FVIII variant according to claim 1, wherein said variant contains a combination of four substitutions of the amino acids at positions 409, 462, 507 and 629 of SEQ ID NO: 3.

7. The isolated human coagulation FVIII variant according to claim 1, wherein said variant further comprises a substitution of at least one amino acid selected from the group consisting of the amino acids at positions 2177, 2183, 2186, 2191, 2196, 2204, 2205, 2213, 2217, 2235, 2258, 2264, 2268 and 2269 of SEQ ID NO: 3.

8. The isolated human coagulation FVIII variant according to claim 1, wherein said variant further comprises a substitution of at least one amino acid selected from the group consisting of the amino acids at positions 2175, 2199, 2200, 2215, 2251, 2252 and 2278 of SEQ ID NO: 3.

9. The isolated human coagulation FVIII variant according to claim 1, wherein the amino acid is substituted by an amino acid selected from an Alanine, a Methionine, a Serine, or a Glycine.

10. The isolated human coagulation FVIII variant according to claim 9, wherein the substituted amino acid is an Alanine.

11. The isolated human coagulation FVIII variant according to claim 1, said human coagulation FVIII variant comprising a substitution of the amino acid at position 462 of SEQ ID NO: 3 and said substitution of 1 to 15 amino acids at a position in SEQ ID NO: 3 is selected from the group consisting of 400, 403, 409, 414, 421, 437, 486, 493, 494, 496, 507, 518, 562, 629, 2175, 2177, 2183, 2186, 2191, 2196, 2199, 2200, 2202, 2204, 2205, 2206, 2212, 2213, 2215, 2217, 2226, 2235, 2244, 2251, 2252, 2258, 2261, 2264, 2268, 2269, 2275, 2278, 2280, 2281, 2282, 2289, 2294, 2311, 2312 and 2316, wherein said variant has decreased antigenicity towards inhibitory antibodies as compared to natural human FVIII, retains procoagulant activity and, optionally, totally or partially lacks the domain B.

12. A pharmaceutical composition comprising the isolated human coagulation FVIII variant according to claim 1 and a pharmaceutically acceptable carrier or excipient.

13. A method for treating hemophilia A in a patient, comprising administering the isolated human coagulation FVIII variant according to claim 1 to said patient.

14. The method according to claim 13, wherein the patient to be treated is a hemophiliac patient with inhibitors.

15. The method according to claim 13, wherein the patient to be treated is a hemophiliac patient before the development of inhibitors.

16. A method for determining an inhibitor type in a patient with hemophilia A comprising performing a recognition test of inhibitory antibodies contained in a serum sample from the patient on one or more isolated human coagulation FVIII variants according to claim 1.

* * * * *

UNITED STATES PATENT AND TRADEMARK OFFICE
CERTIFICATE OF CORRECTION

PATENT NO.         : 8,623,824 B2
APPLICATION NO.    : 12/528379
DATED              : January 7, 2014
INVENTOR(S)        : Didier Saboulard et al.

Page 1 of 6

It is certified that error appears in the above-identified patent and that said Letters Patent is hereby corrected as shown below:

In the Specification

Column 3,
Line 2, "FVIIII variants" should read --FVIII variants--.
Line 8, "US20021165177;" should read --US2002/165177;--.

Column 4,
Line 60, "FVIIII activity" should read --FVIII activity--.

Column 5,
Line 10, "antibodies not" should read --antibodies do not--.

Column 6,
Line 61, "group speculate" should read --group speculates--.

Column 7,
Line 49, "five six," should read --five, six,--.

Figure 6A:
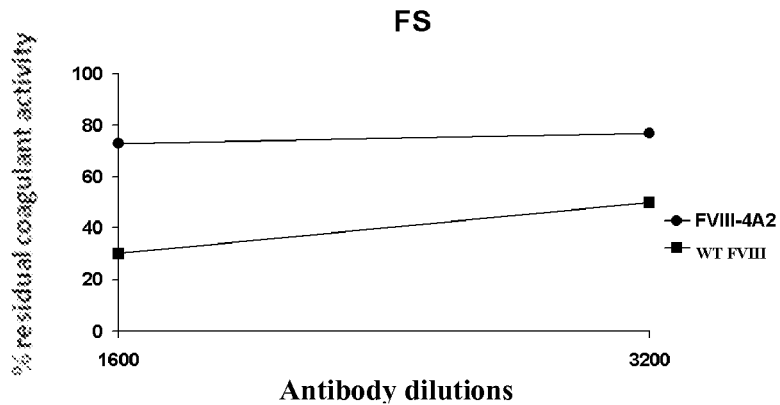
Figure 6B:
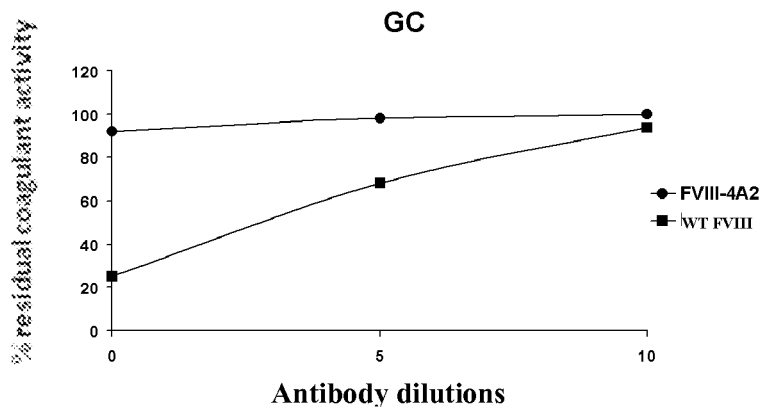
Figure 6C:
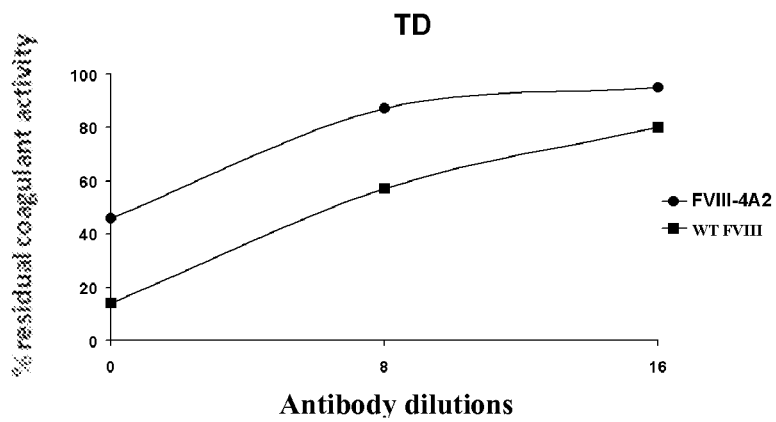
Figure 6D:
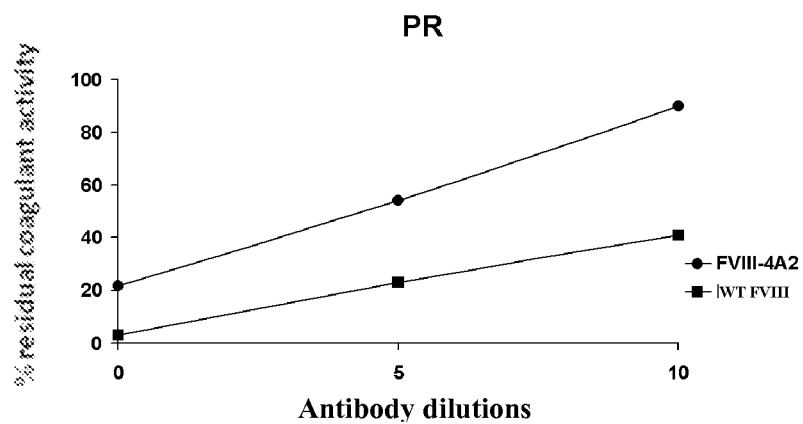
Figure 6E:
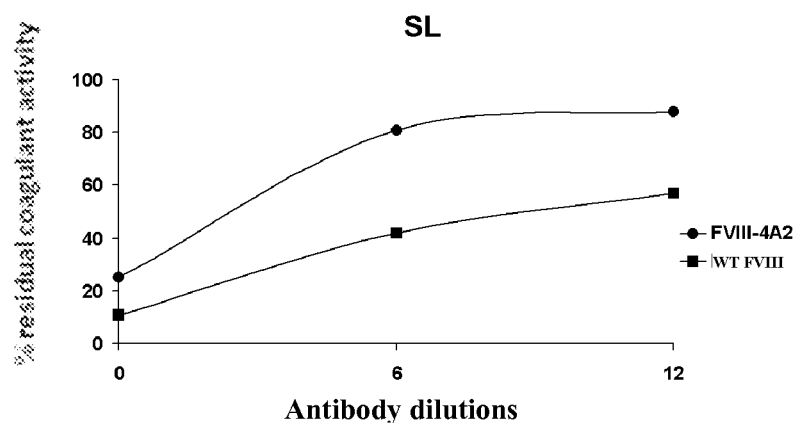
Figure 7A:
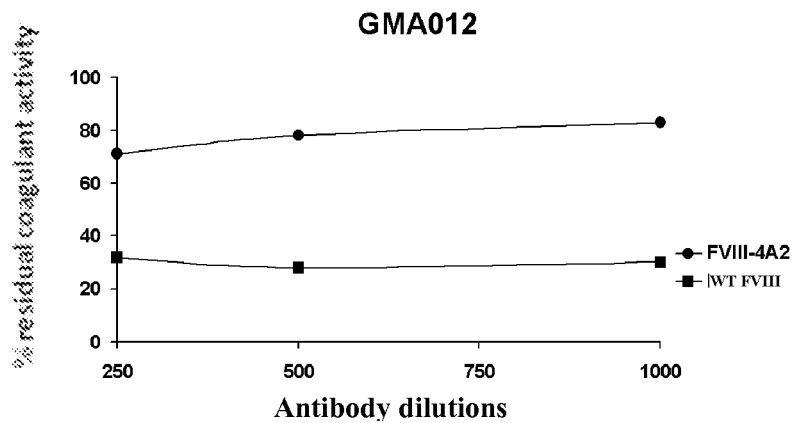
Figure 7B:
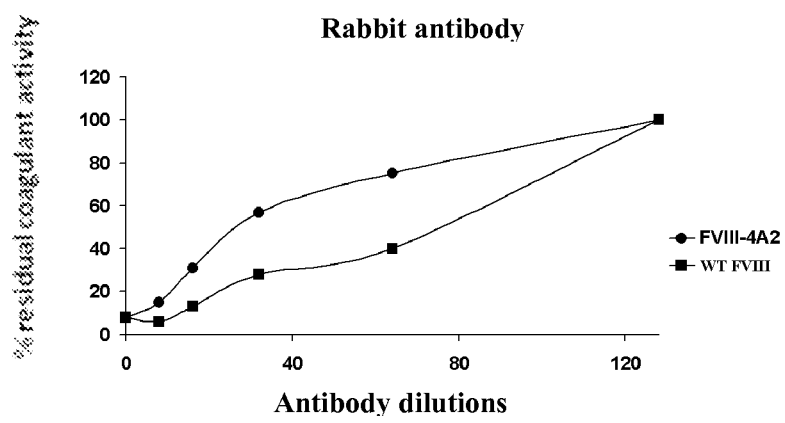

Column 10,
Line 5, "(TD, GC, PR, SL and FS)" should read --(TD (Figure 6C), GC (Figure 6B), PR
     (Figure 6D), SL (Figure 6E) and FS (Figure 6A))--.
Lines 11-12, "(GMA012) and a rabbit polyclonal antibody." should read --(GMA012,
     Figure 7A) and a rabbit polyclonal antibody (Figure 7B).--.
Lines 15-16, "(ESH4) and anti-A2 domain antibody (GMA012)." should read
     --(ESH4, Figure 8B) and anti-A2 domain antibody (GMA012, Figure 8A).--.
Lines 24-25, "(TD, GC, SL and FS measured by Bethesda assay.
     FIGS. 12-14: Primary screen results; list of 158 Alanine"

should read

Signed and Sealed this
Fifteenth Day of September, 2015

Michelle K. Lee
*Director of the United States Patent and Trademark Office*

CERTIFICATE OF CORRECTION (continued)
U.S. Pat. No. 8,623,824 B2

--(TD (Figure 11A), GC (Figure 11B), SL (Figure 11D) and FS (Figure 11C)) measured by Bethesda assay.

Residual activity, determined after incubation with inhibitory antibodies, is divided by remained activity after incubation with a non-immune antibody to give the residual activity percentage.

FIGS. 12-14: Primary screen results; list of 158 Alanine--.

Column 10, Line 42 through Column 14, Line 47,

"FIG. 21: Chromogenic specific activities and abolition to inhibition percentages towards inhibitory antibodies of six double A2 mutants from sera of four hemophiliac patients TD, GC, SL and PR.

Description of the invention

The present invention provides a solution to resolve a serious complication that occurs in 30% of hemophilia A patients treated with recombinant FVIII: the development of an immune response induced by the treatment and directed against the exogenous recombinant FVIII. The solution provided consists in generating recombinant human FVIII molecules having decreased antigenicity of the epitopes usually recognized by inhibitory antibodies. The FVIII variants of the invention have lost one or more epitopes usually recognized by said antibodies.

The present invention provides other solutions consisting in generating human FVIII variants having an improved specific activity as compared to natural FVIII.

Lastly, the present invention provides with FVIII variants having a greater capacity to be secreted, which is interesting for the production of recombinant FVIII and in a potential gene therapy.

The different properties conferred by the mutations in these variants may be of major interest in combination. In a non-limiting example, mutations which confer a specific activity improvement of a variant could compensate an optional relative loss of activity in variants whose mutations confer a abolition to inhibition by inhibitory antibodies and being therefore less antigenic. In another non-limiting example, mutations which confer a higher capacity to be secreted may interesting in combination with mutations conferring an abolition to inhibition by inhibitory antibodies, by allowing, for example, to compensate a optional relative loss of secretion of said less antigenic mutants.

In the present document, the following terminology is used to designate a substitution: 5409A indicates the substitution of the serine residue at position 409 of SEQ ID No. 3 by an alanine. Substitution refers to the replacement of an amino acid residue by another one selected from the other 19 amino acids or by a non-naturally occuring amino acid. The terms "substitution" and "mutation" are interchangeable. The sign "+" indicates a combination of substitutions.

"Comprise" means that the variant or the fragment thereof has one or more substitutions such as indicated with reference to SEQ ID No. 3, but that the variant or the fragment thereof may have other modifications, particularly substitutions, deletions or insertions.

the chromogenic assay mentioned above. This assay was also performed on the robotic platform of the National Hemophilia Treatment Center (Hospices Civils de Lyon). The chromogenic activity of the 158 selected Alanine mutants was carried out with the Coamatic Factor VIII kit (Chromogenix, Instrumentation Laboratory, Milan, Italy) according to the supplier's instructions. Briefly, culture supernatants (50 µl) were diluted in the dilution buffer provided and preincubated at 37° C. for 4 min. The reaction medium (50 µl), preheated at 37° C., was then added for 4 min, after which 50 µl of development medium at 37° C. were added. The formation of product over time was Column 10, Line 42 through Column 14, Line 47 cont'd.

measured immediately on a spectrophotometer at 405 nm after shaking the microtiter plate. Product formation is expressed as mUOD/min. When values were greater than 200 mUOD/min, the assay was repeated using a higher dilution.

FIGS. 12-14 show the activities of the 158 mutants which retained more than 50% of non-mutated FVIII activity. Said 158 mutants were selected for the secondary screening.

Example 4: Secondary screen: Evaluation of loss of antigenicity towards human FVIII inhibitory antibodies The secondary screen correlates to an assay similar to the Bethesda assay, carried out as described below on the 158 mutants selected following the primary screening; said assay comprises a step of contacting a inhibitory serum (or antibody) with a FVIII molecule to be tested or a reference standard and a step of measuring FVIII coagulant activity by chronometric assay.

Culture supernatants obtained after 48 h of contact with COS cells transfected by different FVIII constructs were used. Said supernatants were produced in complete medium [(IMDM, Invitrogen), 10% fetal calf serum, 2 mM L-glutamine, 100 U/ml penicillin, 100 mg/ml streptomycin]. Supernatants were diluted in fresh complete medium to obtain a final chronometric activity comprised in the range of about 10-20% (1 FVIII unit = 100% activity = 200 ng/ml). The culture supernatant diluted or not (140 μ1) was added to 150 μl of FVIII-depleted human plasma (Stago, Asnieres, France). An antibody dilution (10 μl) was then added to the mix. These antibodies are IgG fractions purified on protein A- from hemophiliac patients with inhibitors. An IgG fraction from a non-hemophiliac control was similarly obtained.

Bethesda inhibitor titers were identical to the inhibitory activity from the plasma. The purification protocol therefore did not affect the inhibitory activity of the antibodies. The antibodies were first diluted in fresh complete medium, the measurement being carried out either with a fixed antibody dilution or with serial dilutions. The fixed antibody concentration which was used was that which produced 50% inhibition of a recombinant FVIII standard solution with 12.5% activity. Samples were incubated in a 37° C. water-bath for 1h30. Coagulant activity was then determined on a MDA-II apparatus (BioMérieux, Marcy-l'Etoile) and compared to that of a standard curve established from an identical FVIII stably produced in the CHO cell line. Results are expressed as a percentage which represents the abolition to inhibition of coagulant activity of a given mutant by inhibitory antibodies from a patient's serum. Said percentage was calculated as shown in Figure 5 for the FVIII mutant E518A. Abolition to inhibition expressed is a percentage =-[(b-a)/a] × 100; where "a" is the percentage residual activity of the WT (serum + IgG / serum—IgG) and "b" is the percentage residual activity of the mutant (serum + IgG / serum -IgG).

FIGS. 15-18 show for 30 single mutants the percentages of abolition to inhibition for sera from five hemophiliac patients. Said mutants were selected in the secondary screen of the 158 mutants selected in the primary screen. Several mutants show a high percentage of abolition to inhibition with certain sera, such as mutant 2316 for sera TD and SL, mutant 2294 for serum GC, mutant 403 for serum FS and mutant 2275 for serum PR.

Patients' sera were selected for their high Bethesda titers (greater than 10 BU) and their different inhibitor profiles. These patients can no longer be treated with FVIII injections and need bypassing agents. Thus, obtaining FVIII Alanine mutants which abolish, even partially, the inhibition of FVIII activity by the inhibitory antibodies of one of these patients, is a major step forward to the future approaches of treating hemophiliac patients with inhibitors. The different data obtained on a large number of mutants as well as the different sera tested will make it possible to create Column 10, Line 42 through Column 14, Line 47 cont'd.

combinations of mutations leading to an improved FVIII which can avoid a majority of inhibitory antibodies while retaining its procoagulant activity.

The reproducibility of FVIII expression level related to transfections was controlled by following the specific activity of wild-type FVIII. Indeed, specific activities calculated from antigen determinations (Stago commercial ELISA kit) were identical for wild-type FVIIIs produced in different transfections. Likewise, antigen concentrations were determined for mutants having retained at least 50% of wild-type FVIII activity and their specific activity was determinate throw. Specific activity corresponds to raw activity measured in the chromogenic assay (mUOD/min) relative to protein concentration (ng/ml) obtained with an ELISA kit (Stago FVIII kit). Figure 19 shows comparative data of raw and specific activities of 30 mutants selected in the secondary screen.

The eight FVIII Alanine mutants 2175, 2199, 2200, 2215, 2251, 2252, 2278 and 2316 displayed a far above average capacity to be secreted in the COS cell production medium used in the scope of the present invention. FIG. 3 depicts the data obtained for these eight mutants. Raw coagulant activity of these mutants was determined by chromogenic assay. Their concentration was approximately two to four times higher than that of wild-type FVIII. This property is interesting for producing recombinant FVIII and might make it possible to lower production costs of a new generation FVIII. Also, it might be advantageous in a gene therapy for hemophiliac patients. Moreover, these mutations which confer a greater capacity to be secreted may be of major interest in combination with mutations conferring abolition to inhibition by inhibitory antibodies, by allowing, for example, to compensate an optional relative loss of secretion of said less antigenic mutants.

The 15 mutants 2177, 2183, 2186, 2191, 2196, 2204, 2205, 2206, 2213, 2217, 2235, 2258, 2264, 2268 and 2269 displayed far higher specific activity than wild-type FVIII, while maintaining a high production level, around to that of wild-type FVIII (concentration greater than 10 ng/ml). The specific activities of these 15mutants are given in FIG. 4. Raw coagulant activity of these mutants was determined by chromogenic assay. This property is interesting because it would allow smaller or less frequent doses of FVIII to be injected in patients. Moreover, these mutations which confer a higher specific activity might be of major interest in combination with mutations conferring abolition to inhibition by inhibitory antibodies, by allowing to compensate an optional relative loss of activity of said less antigenic mutants.

Example 5: Selection and combination of the best single mutants selected in the secondary screen Among the 30 single mutants selected in the secondary screen, eight were chosen in order to combine their respective mutations, to obtain a cumulative/additive effect of remarkable properties of each. The selection criteria for these mutants were complex and considered the following parameters:

- at least 25% abolition to inhibition for at least one of the test sera from hemophiliac patients with inhibitors;
- raw coagulant activity at least 100% relative to non-mutated FVIII; and
- reproducibly good level of expression.

The eight selected mutants were mutants 409, 462, 507 and 629 in the A2 domain and mutants 2289, 2294, 2312 and 2316 in the C2 domain. As noted earlier, the selection criterion considered of a high specific activity (coagulant activity relative to expression level), as shown in FIG. 19. This specific activity level had to be constant in the different experiments.

The 28 double mutants resulting from the combination of the eight single mutations 409, 462, 507, 629, 2289, 2294, 2312 and 2316 (six A2 double mutants +six C2 double mutants +sixteen A2-C2

Column 10, Line 42 through Column 14, Line 47 cont'd.

CERTIFICATE OF CORRECTION (continued)
U.S. Pat. No. 8,623,824 B2 double mutants presented in FIG. 20) were constructed by mutagenesis methods known to one skilled in the art. These mutants were transiently expressed in COS-7 mammalian cells as described in Example 2. Their expression level and their activity level were determined as described in the previous examples, respectively by ELISA and chromogenic assay (mUOD/min). These 28 mutants were then assessed for their abolition to inhibition by antibodies from hemophiliac patients. The A2 double mutants displayed a significant abolition to inhibition for one or all of the antibodies from the patients' sera, whereas the combinations containing C2 domain mutations (six C2 double mutants +sixteen A2-C2 double mutants) displayed an insignificant or null abolition to inhibition.

FIG. 21 shows the specific activities of the six A2 double mutants and their percentage of abolition to inhibition by sera from four hemophiliac patients TD, GC, SL and PR calculated as in Example 4. Especially preferred double mutants significantly abolished antibodies from a minimum of three over the four patients. This illustrates the cumulative effect of the four single mutations in the A2 domain. The choice was therefore based on the combination of the four mutations 409, 507, 462 and 629. Triple mutants and the quadruple mutant comprising these four mutations 409, 507, 462 and 629 were also constructed.

Residual activity, determined after incubation with inhibitory antibodies, is divided by remained activity after incubation with a non-immune antibody to give the residual activity percentage.

Table 1: Primary screen results; list of 158 Alanine mutants selected for secondary screening, having retained at least 50% of raw activity relative to non-mutated FVIII activity.

Table 2: Secondary screening: Bethesda assays on 30 mutants displaying modified antigenicity towards sera from five hemophiliac patients with inhibitors. Results are expressed as the abolition to inhibition percentage for each mutant as exemplified in FIG. 5.

Table 3: Comparison of specific activity and raw activity relative to non-mutated FVIII activity for the 30 mutants displaying modified antigenicity towards sera from five hemophiliac patients with inhibitors.

Table 4: List of all FVIII double mutants produced from the eight single mutants FVIII409A, FVIII462A, FVIII507A, FVIII629A, FVIII2289A, FVIII2294A, FVIII2312A and FVIII2316A.

Table 5: Chromogenic specific activities and abolition to inhibition percentages towards inhibitory antibodies of six double A2 mutants from sera of four hemophiliac patients TD, GC, SL and PR.

DESCRIPTION OF THE INVENTION"

should read

--FIG. 21: Chromogenic specific activities and abolition to inhibition percentages towards inhibitory antibodies of six double A2 mutants from sera of four hemophiliac patients TD, GC, SL and PR.

DESCRIPTION OF THE INVENTION--.

Column 27,
Line 44, "responsible of its" should read --responsible for its--.
Column 28,

CERTIFICATE OF CORRECTION (continued)
U.S. Pat. No. 8,623,824 B2

Line 20, "from a patient" should read --from one patient--.

Column 31,
Line 48, "of a continuously use" should read --of a continuous use--.
Lines 55-56, "might be encompass for a" should read --might encompass a--.

Column 32,
Line 61, "propose to use of the" should read --propose to use the--.
Lines 66-67, "decrease for the control" should read --decrease the control--.

Column 33,
Line 55, "consisted in" should read --consisted of--.

Column 35,
Line 33, "Table 1 shows" should read --Figures 12-14 show--.

Column 36,
Line 19, "Table 2 shows" should read --Figures 15-18 show--.
Line 52, "Table 3 shows" should read --Figure 19 shows--.

Column 37,
Line 41, "shown in Table 3." should read --shown in Figure 19.--.
Line 46, "in Table 4)" should read --in Figure 20)--.
Line 60, "Table 5 shows" should read --Figure 21 shows--.

Column 39,
Line 35, "about 27±1" should read --about 27 ± 11--.
Line 65, "added (Iris" should read --added (Tris--.